US006979425B1

(12) United States Patent
Ganz et al.

(10) Patent No.: US 6,979,425 B1
(45) Date of Patent: *Dec. 27, 2005

(54) HIGH CAPACITY MICROARRAY DISPENSING

(75) Inventors: Brian L. Ganz, Carlsbad, CA (US); Mandel W. Mickley, Oceanside, CA (US); John Andrew Moulds, Encinitas, CA (US); Chritopher T. Brovold, Carlsbad, CA (US)

(73) Assignee: RoboDesign International, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/699,818

(22) Filed: Oct. 30, 2000

Related U.S. Application Data

(63) Continuation-in-part of application No. 09/411,943, filed on Oct. 4, 1999, now Pat. No. 6,148,878, and a continuation-in-part of application No. 09/611,256, filed on Jul. 6, 2000.
(51) Int. Cl.$^7$ .......................... B01L 3/02; G01N 15/06; G01N 21/00; G01N 21/29; G01N 35/00
(52) U.S. Cl. ....................... 422/100; 422/68.1; 422/66; 422/67; 422/82.05; 436/180; 436/46; 436/49; 73/863.01; 73/864.11; 141/129
(58) Field of Search ........................... 422/99, 100, 103, 422/105, 68.1, 58, 82.05, 66, 67; 141/1, 119, 141/129, 130, 57, 61; 436/174, 180, 46, 49; 73/863.01, 864.2, 864.11

(56) References Cited

U.S. PATENT DOCUMENTS 3,650,306 A * 3/1972 Lancaster .................... 141/238

(Continued)

Primary Examiner—Yelena Gakh
Assistant Examiner—Brian R Gordon

(74) Attorney, Agent, or Firm—John R. Ross; John R. Ross, III

(57) ABSTRACT

A high capacity microarrayer for spotting solution onto slides in an automated microarray dispensing device. A microplate indexing device automatically moves, in sequence, a plurality of microplates to a solution removal area. A dispense head accesses each microplate at the solution removal area to remove solution from the microplate. The dispense head then moves to a slide positioning station to spot slides at the slide positioning station. In a preferred embodiment of the present invention, the microplate indexing station has at least one input stacking chamber for stacking microplates, and at least one output stacking chamber for stacking microplates. A walking beam indexer is disposed between the at least one input stacking chamber and the at least one output stacking chamber. The walking beam indexer is for moving microplates from said at least one input stacking chamber to said at least one output stacking chamber. While at the solution removal area, a lid lifter lifts the lid off each microplate to permit the microplate to be accessed by the dispense head for solution removal. After the solution is removed, the lid lifter replaces the lid. In another preferred embodiment, there is at least one light source capable of illuminating the slides, and at least one camera operating in conjunction with the at least one light source. The at least one camera is capable of acquiring and transmitting slide image data to a computer. The computer is programmed to receive the slide image and analyze it. The computer will then generate post analysis data based on the analysis of the slide image data. The post analysis data is available for improving the spotting of the solution onto the slides. In a preferred embodiment, the slide image data includes information relating to slide alignment, information relating to spot quality, and slide identification information. In a preferred embodiment, the analysis of the information relating to slide alignment enables the computer to make automatic adjustments to the relative positions of the at least one dispense head and the slides to increase the accuracy of the spotting. In a preferred embodiment, the analysis of the information relating to spot quality identifies a spot as pass or fail. An operator is then able to rework the spot. In a preferred embodiment, the analysis of the slide identification information enables the computer to track each slide.

1 Claim, 62 Drawing Sheets

U.S. PATENT DOCUMENTS

| | | | | |
|---|---|---|---|---|
| 4,106,911 | A * | 8/1978 | Marcelli | 141/237 |
| 4,221,032 | A * | 9/1980 | Cousino et al. | 29/2 |
| 4,478,094 | A * | 10/1984 | Salomaa et al. | 73/863.32 |
| 4,554,839 | A * | 11/1985 | Hewett et al. | 422/100 |
| 4,586,546 | A * | 5/1986 | Mezei et al. | 141/2 |
| 5,061,639 | A * | 10/1991 | Lung et al. | 436/164 |
| 5,104,621 | A * | 4/1992 | Pfost et al. | 422/100 |
| 5,306,510 | A * | 4/1994 | Meltzer | 422/65 |
| 5,415,060 | A * | 5/1995 | DeStefano, Jr. | 74/529 |
| 5,439,649 | A * | 8/1995 | Tseung et al. | 422/99 |
| 5,772,966 | A * | 6/1998 | Maracas et al. | 222/136 |
| 5,865,224 | A * | 2/1999 | Ally et al. | 141/130 |
| 5,871,696 | A * | 2/1999 | Roberts et al. | 422/65 |
| 5,879,628 | A * | 3/1999 | Ridgeway et al. | 235/462.01 |
| 5,906,795 | A * | 5/1999 | Nakashima et al. | 422/100 |
| 5,948,359 | A * | 9/1999 | Kalra et al. | 422/100 |
| 5,988,236 | A * | 11/1999 | Fawcett | 141/130 |
| 6,006,800 | A * | 12/1999 | Nakano | 141/130 |
| 6,024,925 | A * | 2/2000 | Little et al. | 222/394 |
| 6,026,174 | A * | 2/2000 | Palcic et al. | 382/128 |
| 6,159,425 | A * | 12/2000 | Edwards et al. | 422/63 |
| 6,182,719 | B1 * | 2/2001 | Yahiro | 141/1 |
| 6,215,892 | B1 * | 4/2001 | Douglass et al. | 382/128 |
| 6,219,442 | B1 * | 4/2001 | Harper et al. | 348/153 |
| 6,246,785 | B1 * | 6/2001 | Molnar et al. | 382/133 |
| 6,252,979 | B1 * | 6/2001 | Lee et al. | 359/382 |
| 6,255,116 | B1 * | 7/2001 | Leber et al. | 422/100 |
| 6,263,095 | B1 * | 7/2001 | Rushbrooke et al. | 382/128 |
| 6,269,846 | B1 * | 8/2001 | Overbeck et al. | 118/243 |
| 6,271,022 | B1 * | 8/2001 | Bochner | 356/388 |
| 6,275,777 | B1 * | 8/2001 | Shimizu | 382/133 |
| 6,309,362 | B1 * | 10/2001 | Guirguis | 600/573 |
| 6,330,349 | B1 * | 12/2001 | Hays et al. | 382/128 |
| 6,355,487 | B2 * | 3/2002 | Kowallis | 422/100 |
| 6,358,470 | B1 * | 3/2002 | Higuchi | 422/100 |
| 6,372,185 | B1 * | 4/2002 | Shumate et al. | 422/100 |
| 6,395,231 | B1 * | 5/2002 | Kraemer et al. | 141/130 |
| 6,402,837 | B1 * | 6/2002 | Shtrahman et al. | 117/200 |
| 6,472,218 | B1 * | 10/2002 | Stylli et al. | 436/48 |
| 6,485,690 | B1 * | 11/2002 | Pfost et al. | 422/102 |
| 6,576,476 | B1 * | 6/2003 | Taylor et al. | 436/172 |
| 6,685,884 | B2 * | 2/2004 | Stylli et al. | 422/63 |
| 2001/0048899 | A1 * | 12/2001 | Marouiss et al. | 422/100 |
| 2002/0012611 | A1 * | 1/2002 | Stylli et al. | 422/65 |
| 2002/0019003 | A1 * | 2/2002 | Haas et al. | 435/6 |
| 2002/0064482 | A1 * | 5/2002 | Tisone et al. | 422/100 |
| 2002/0176803 | A1 * | 11/2002 | Hamel et al. | 422/100 |
| 2003/0161761 | A1 * | 8/2003 | Williams et al. | 422/63 |
| 2003/0180189 | A1 * | 9/2003 | Velghe et al. | 422/100 |

* cited by examiner

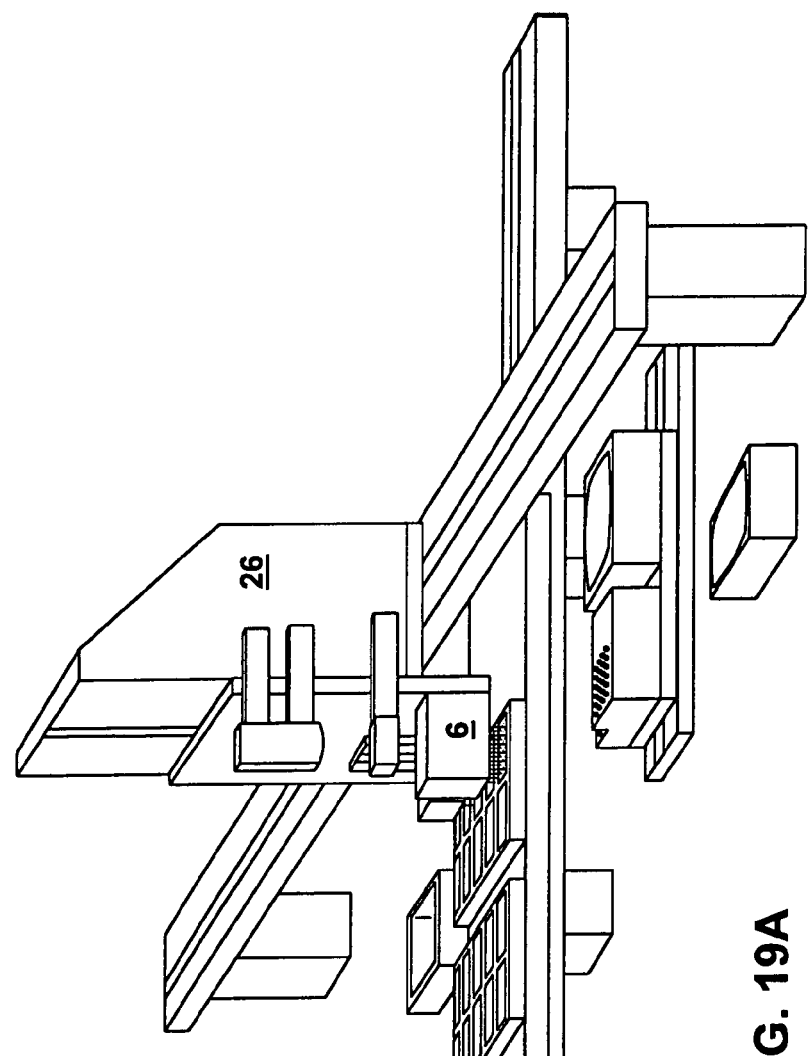
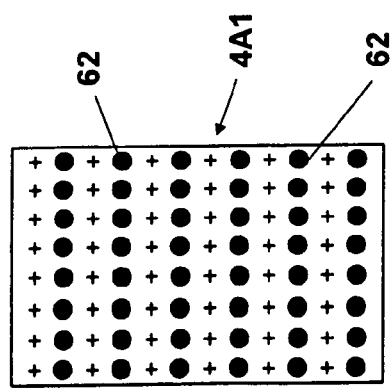
FIG. 19A
FIG. 19B

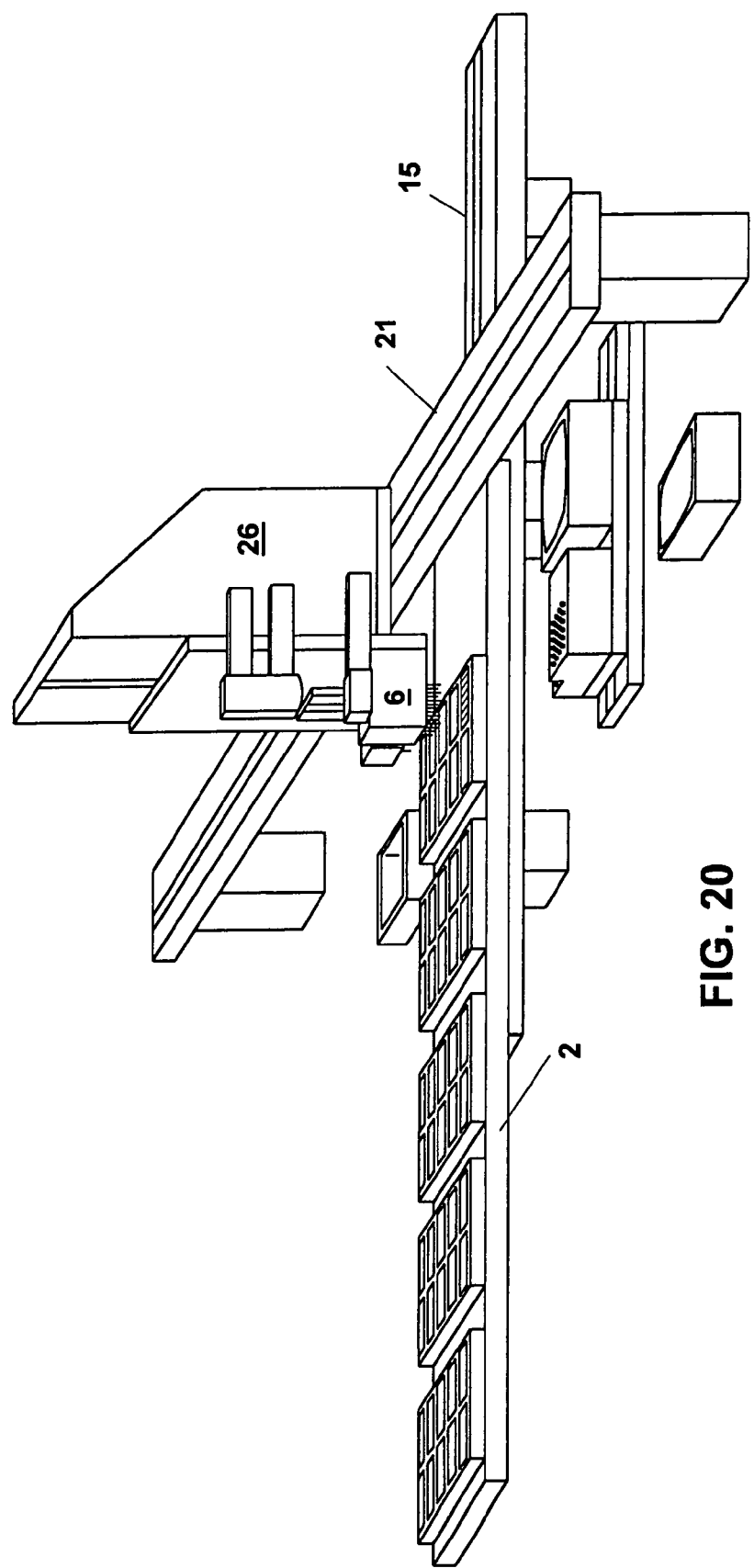

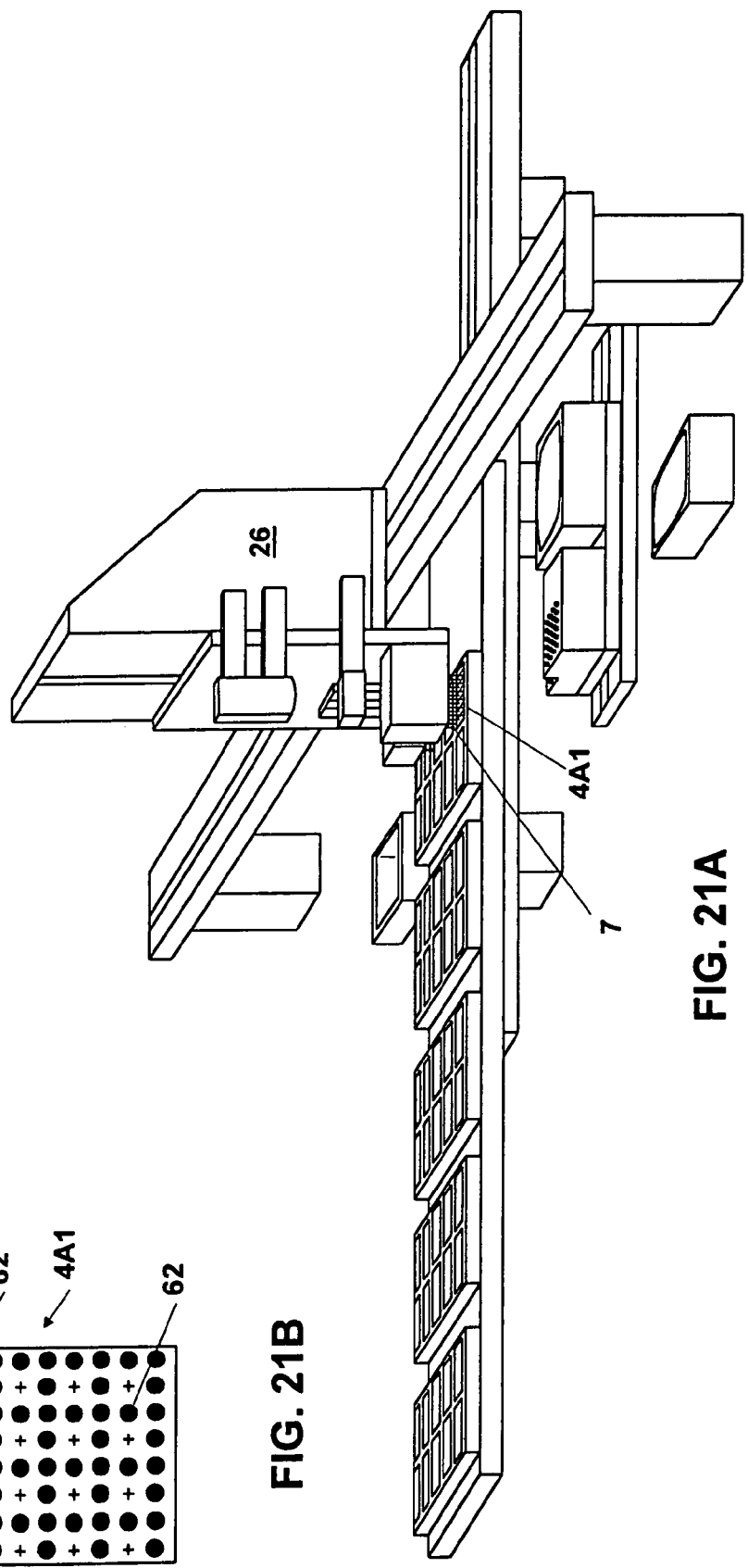

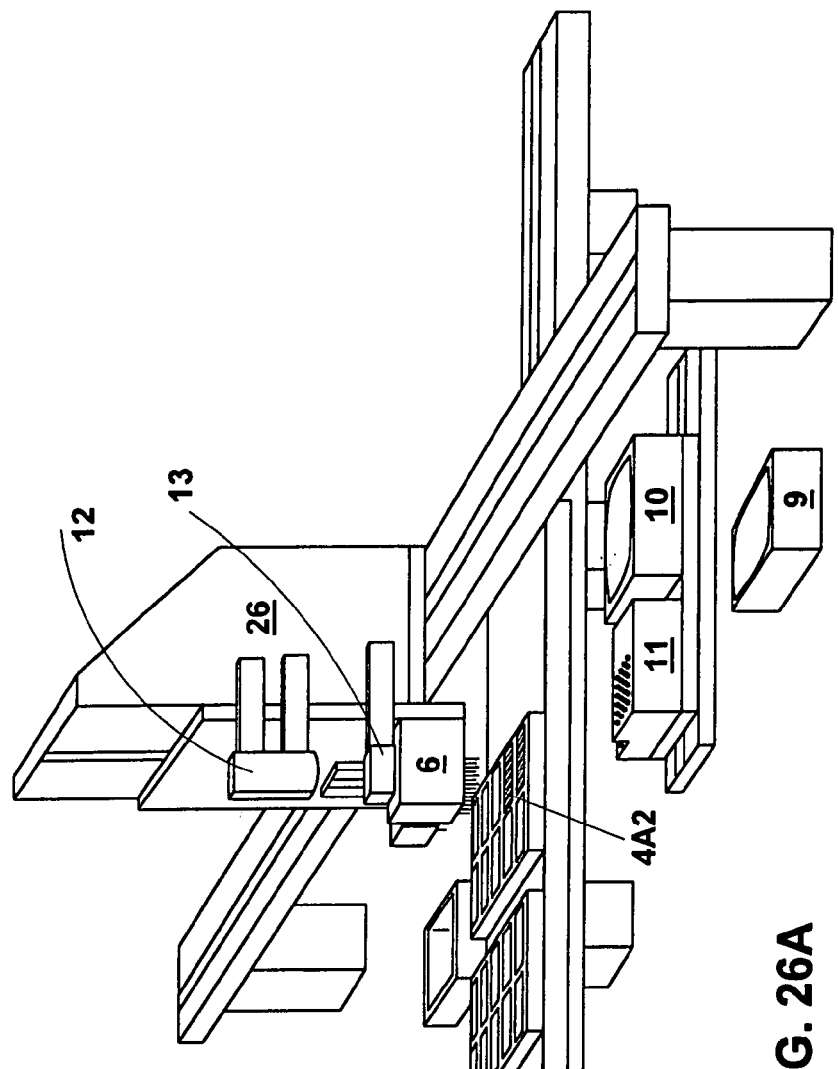
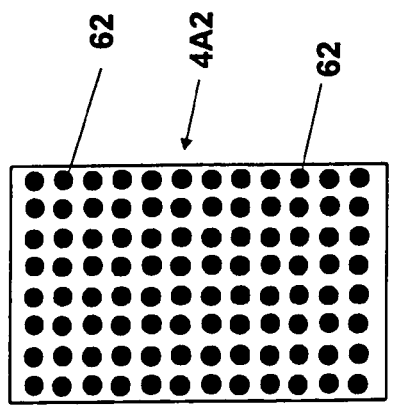
FIG. 26A
FIG. 26B

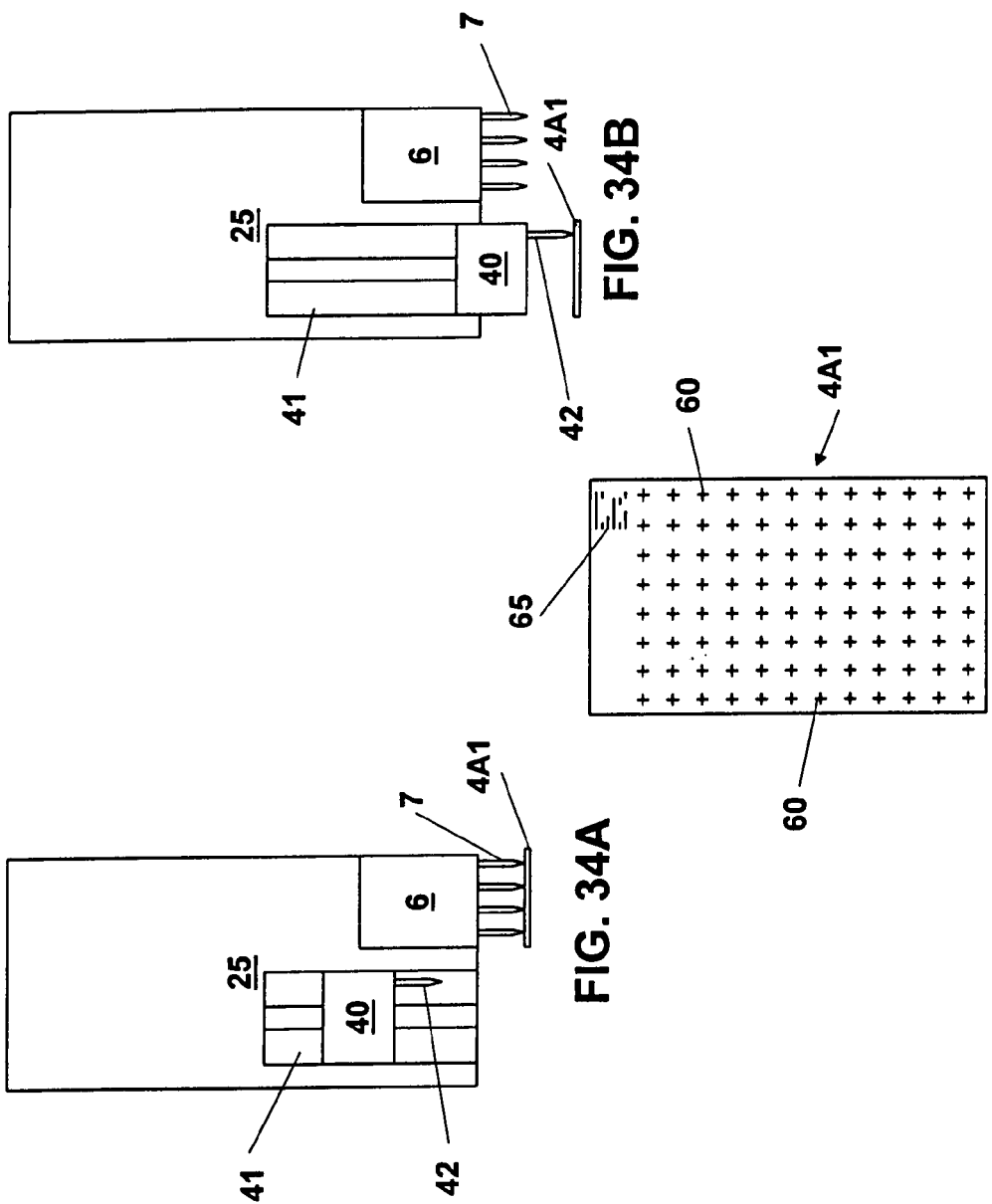

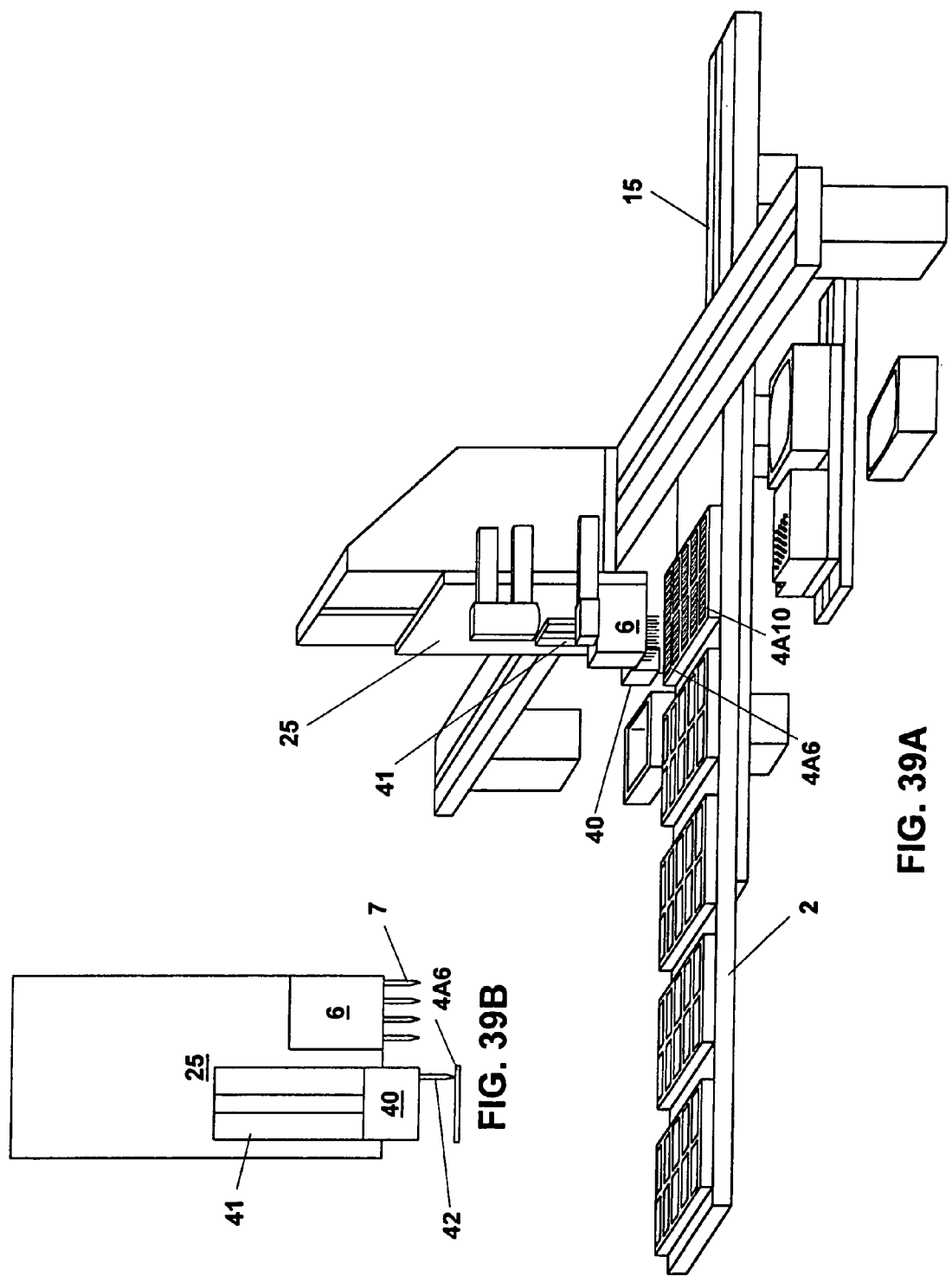

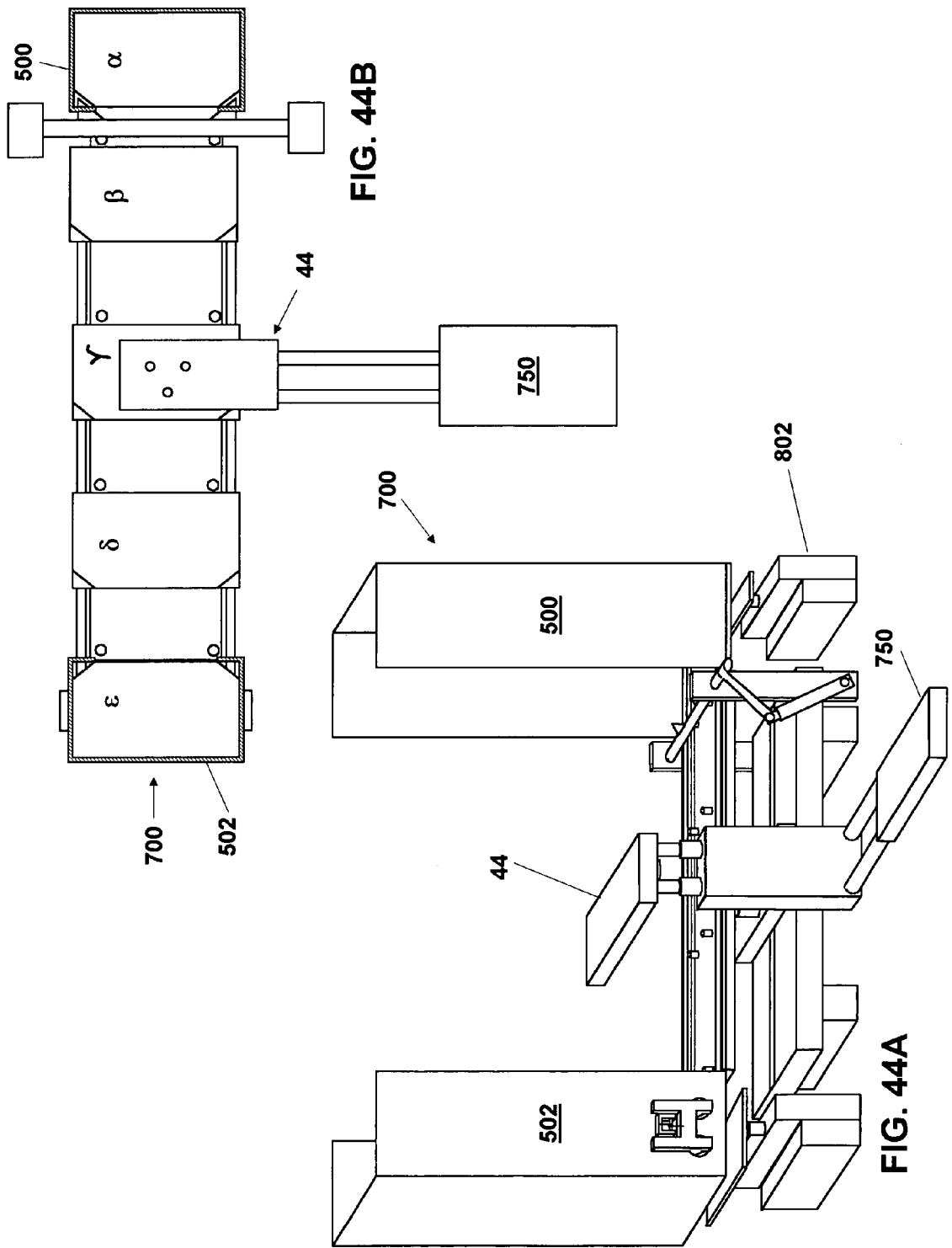

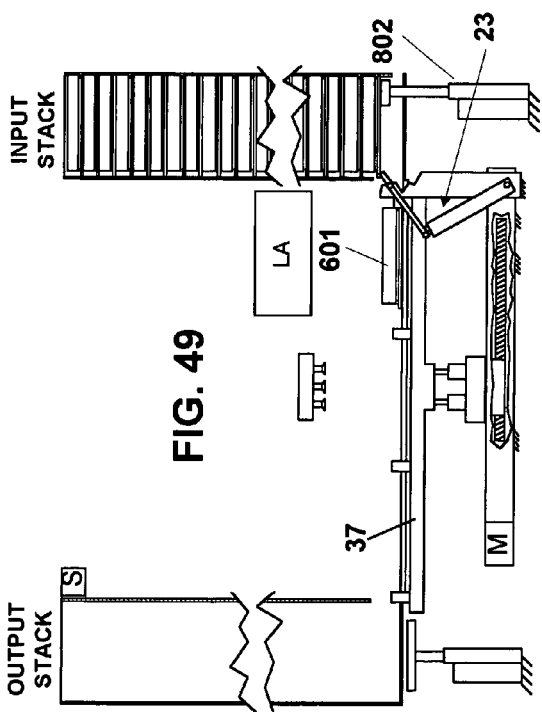
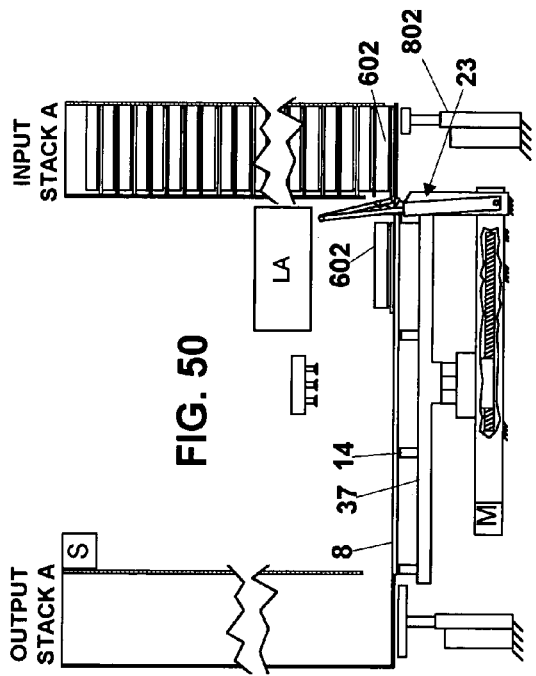
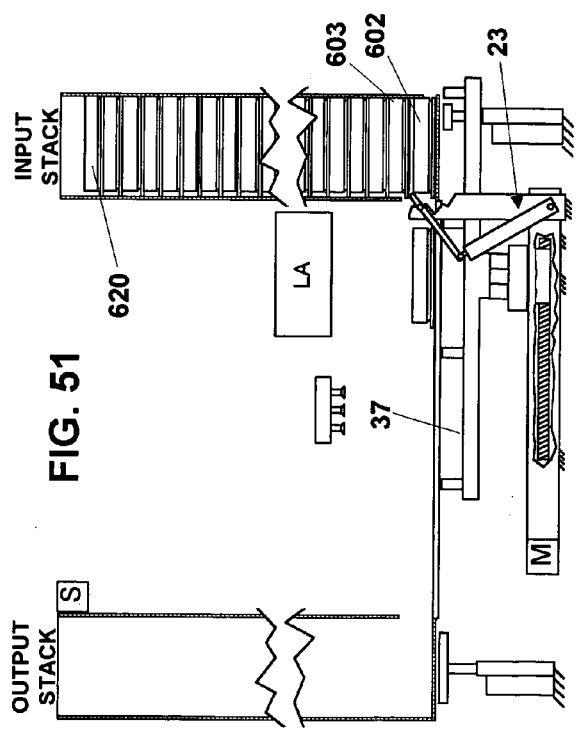
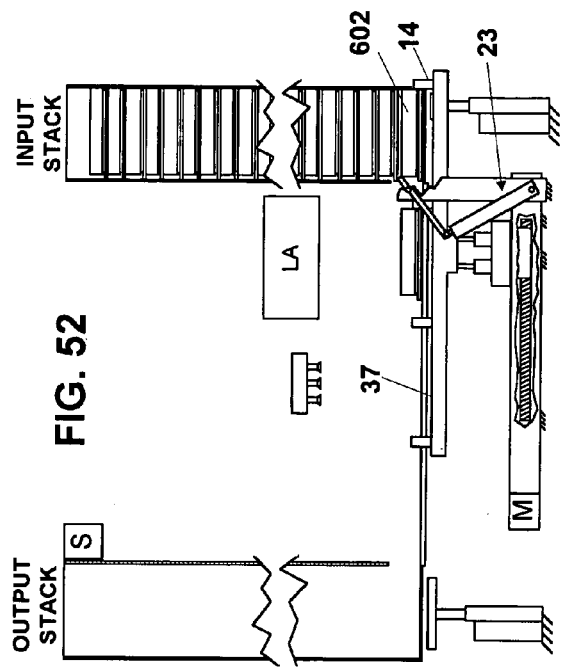

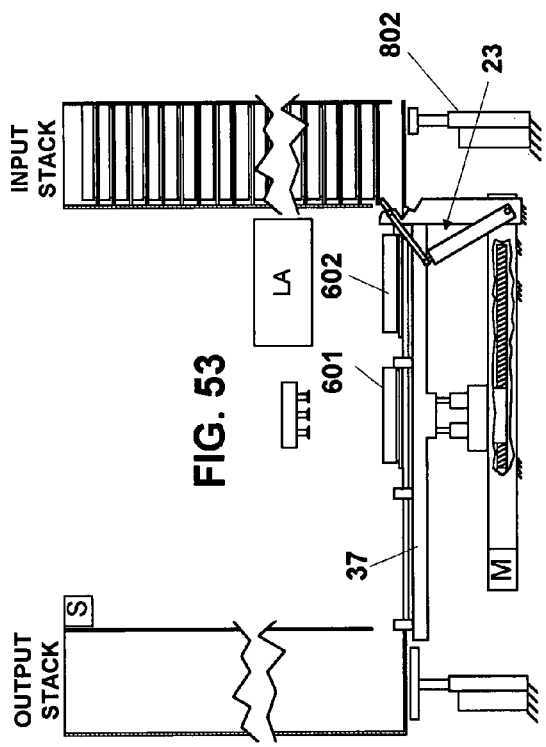
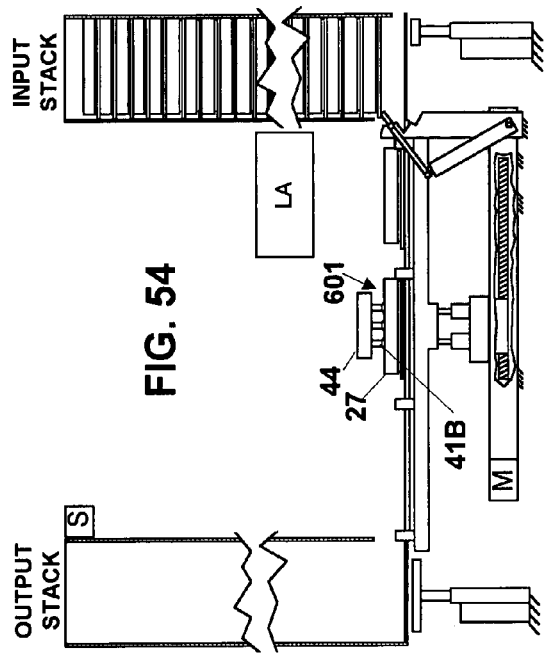
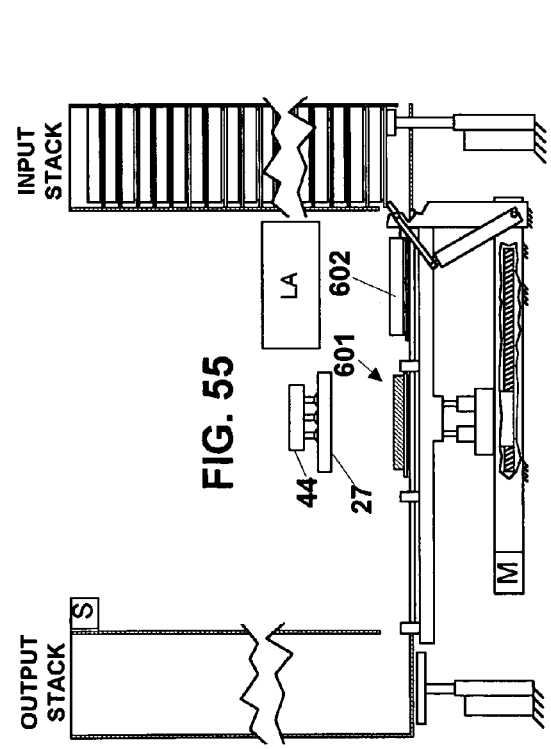
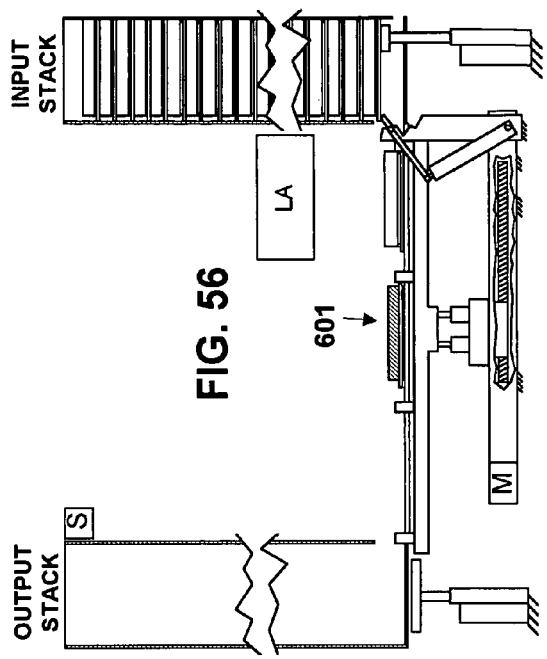

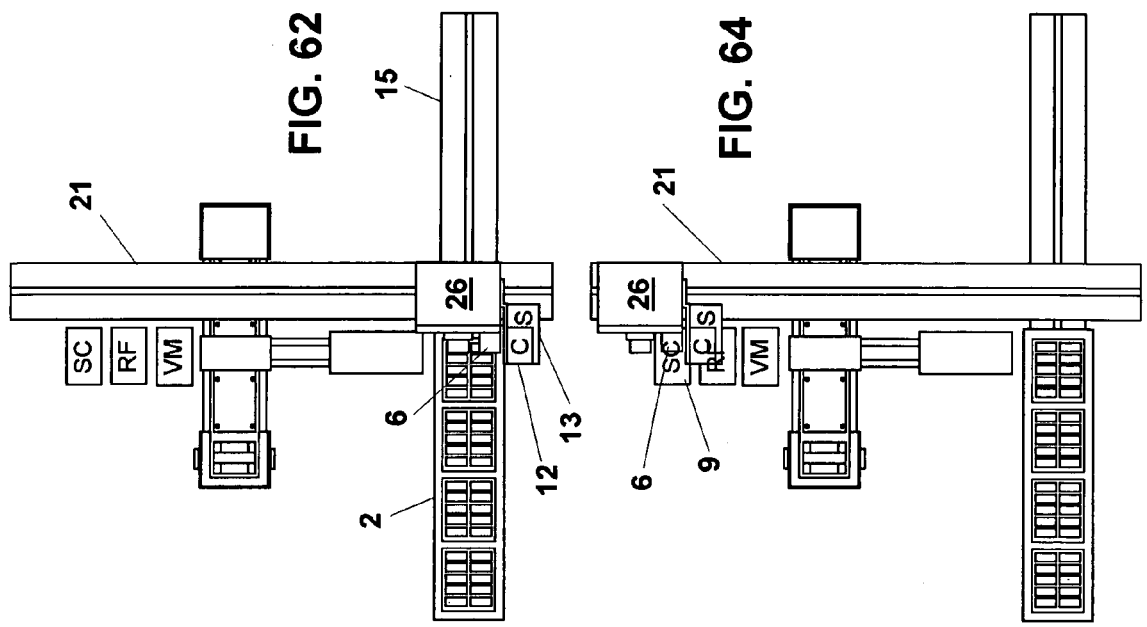
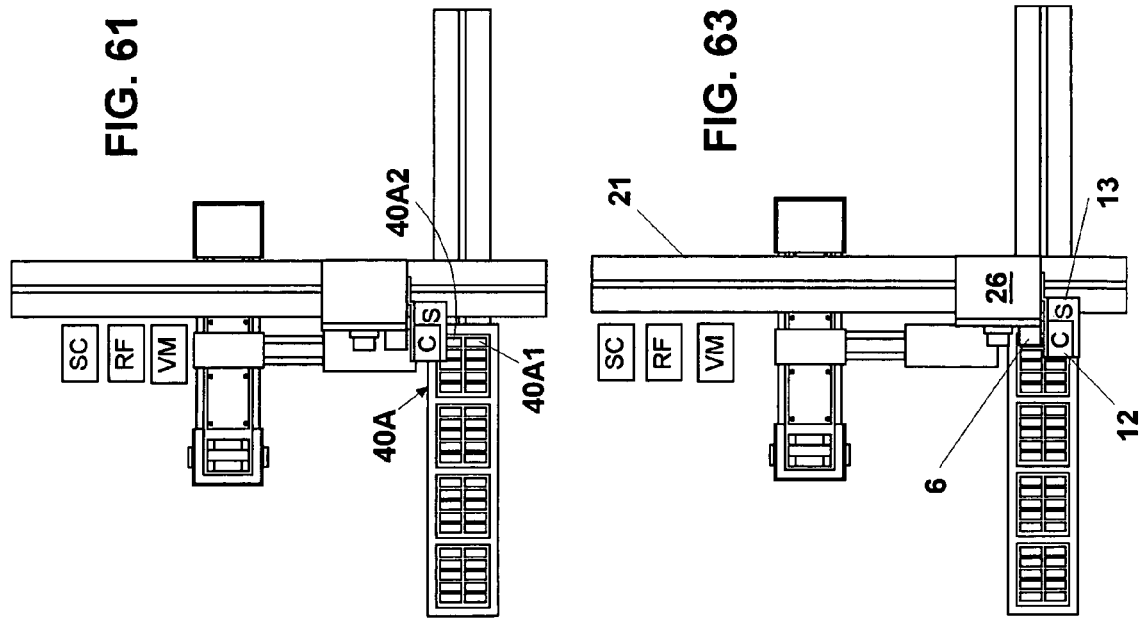

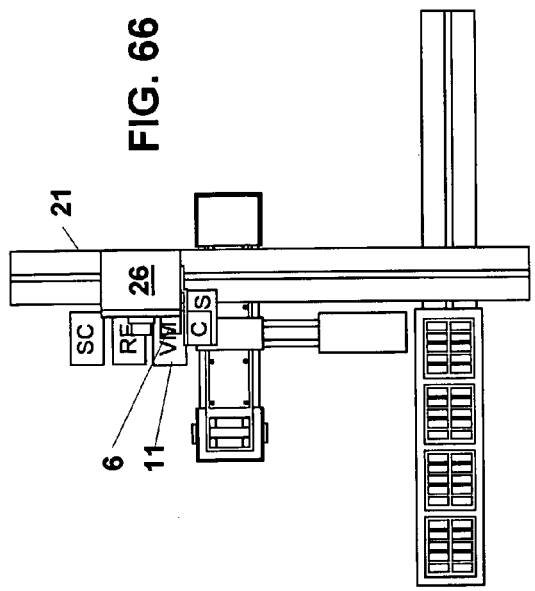
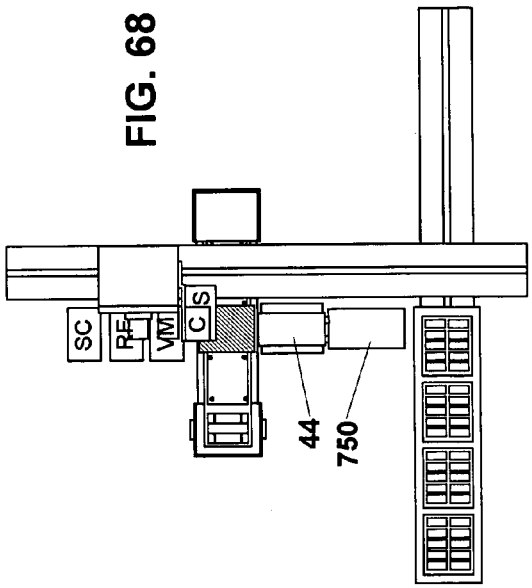
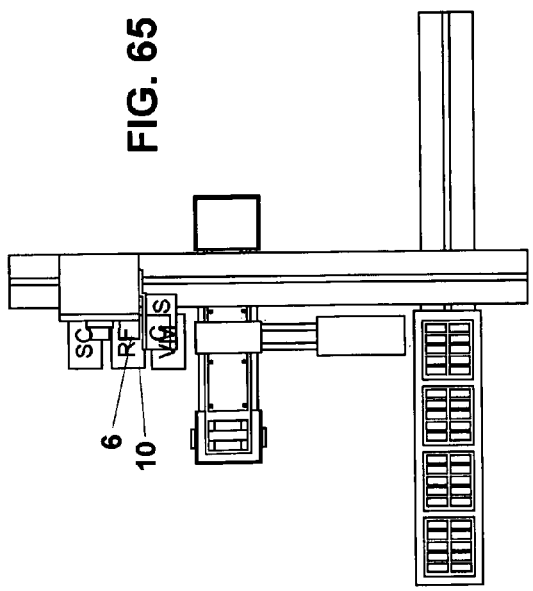
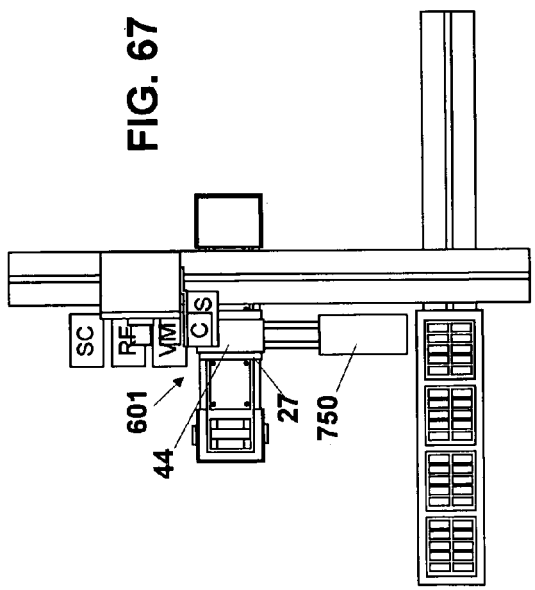

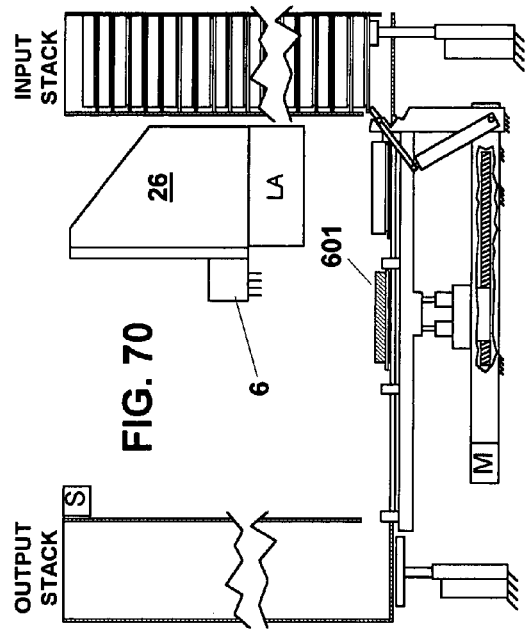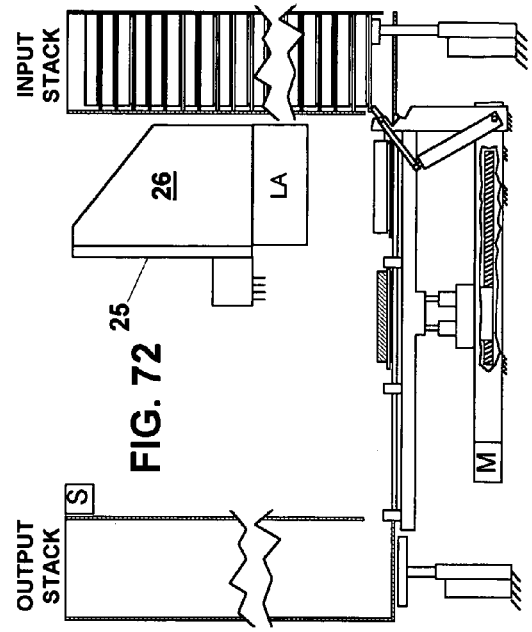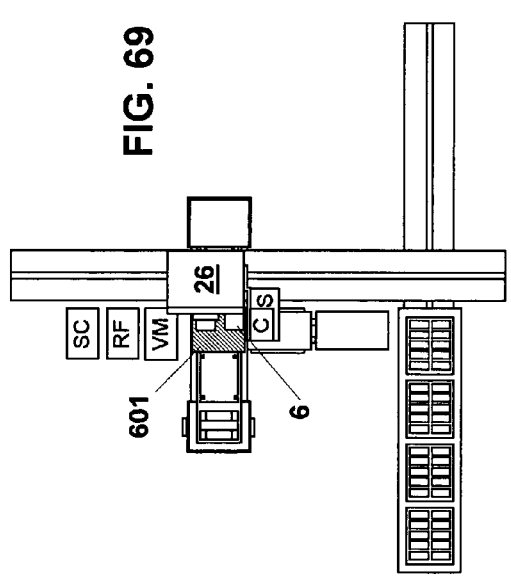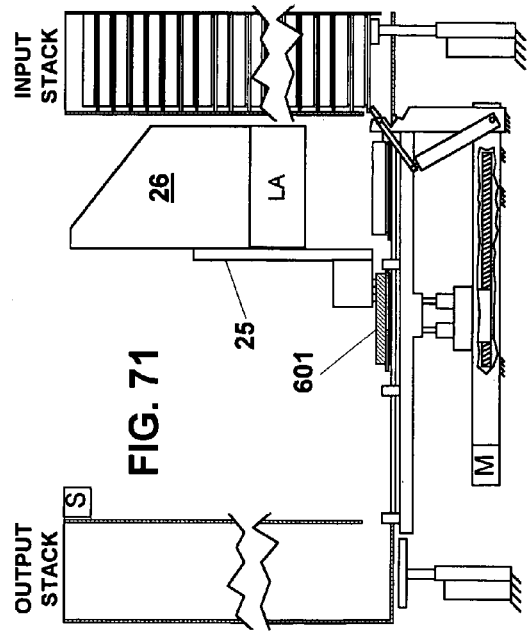

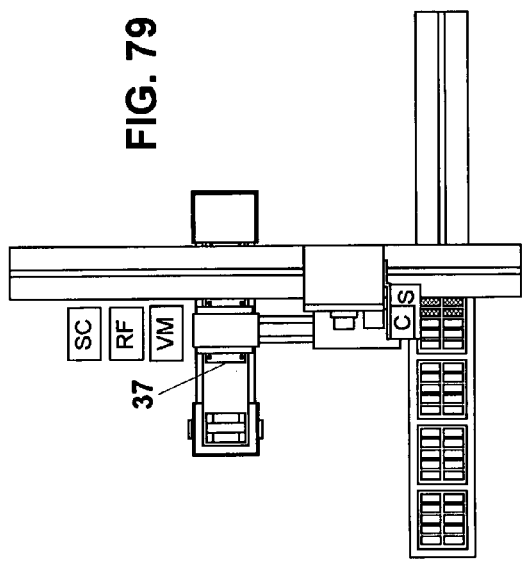
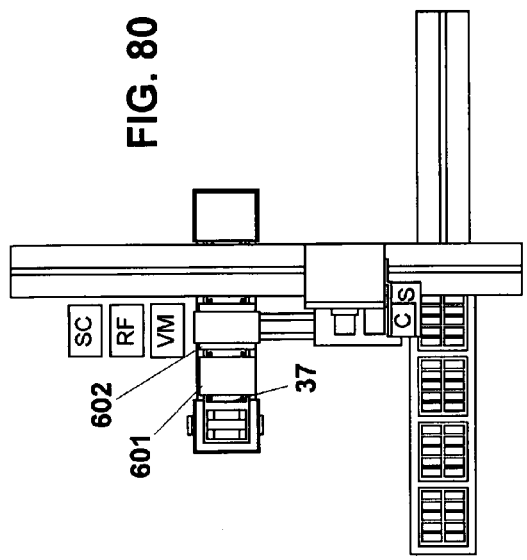
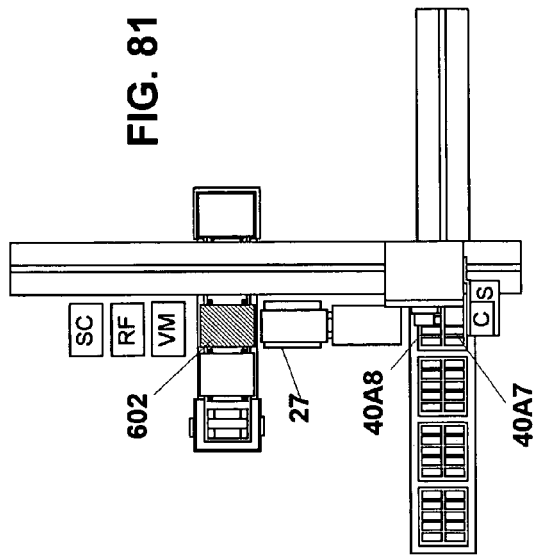
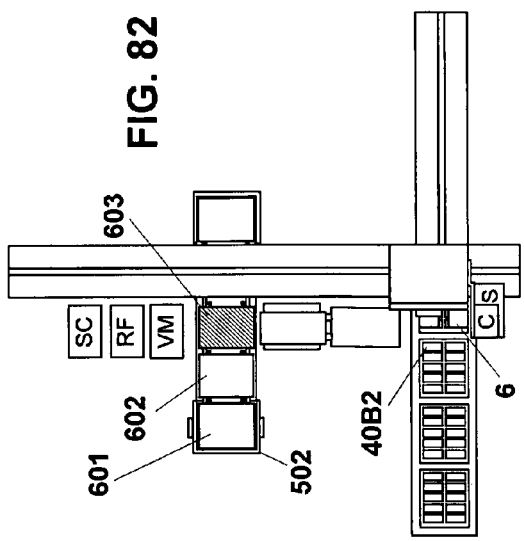

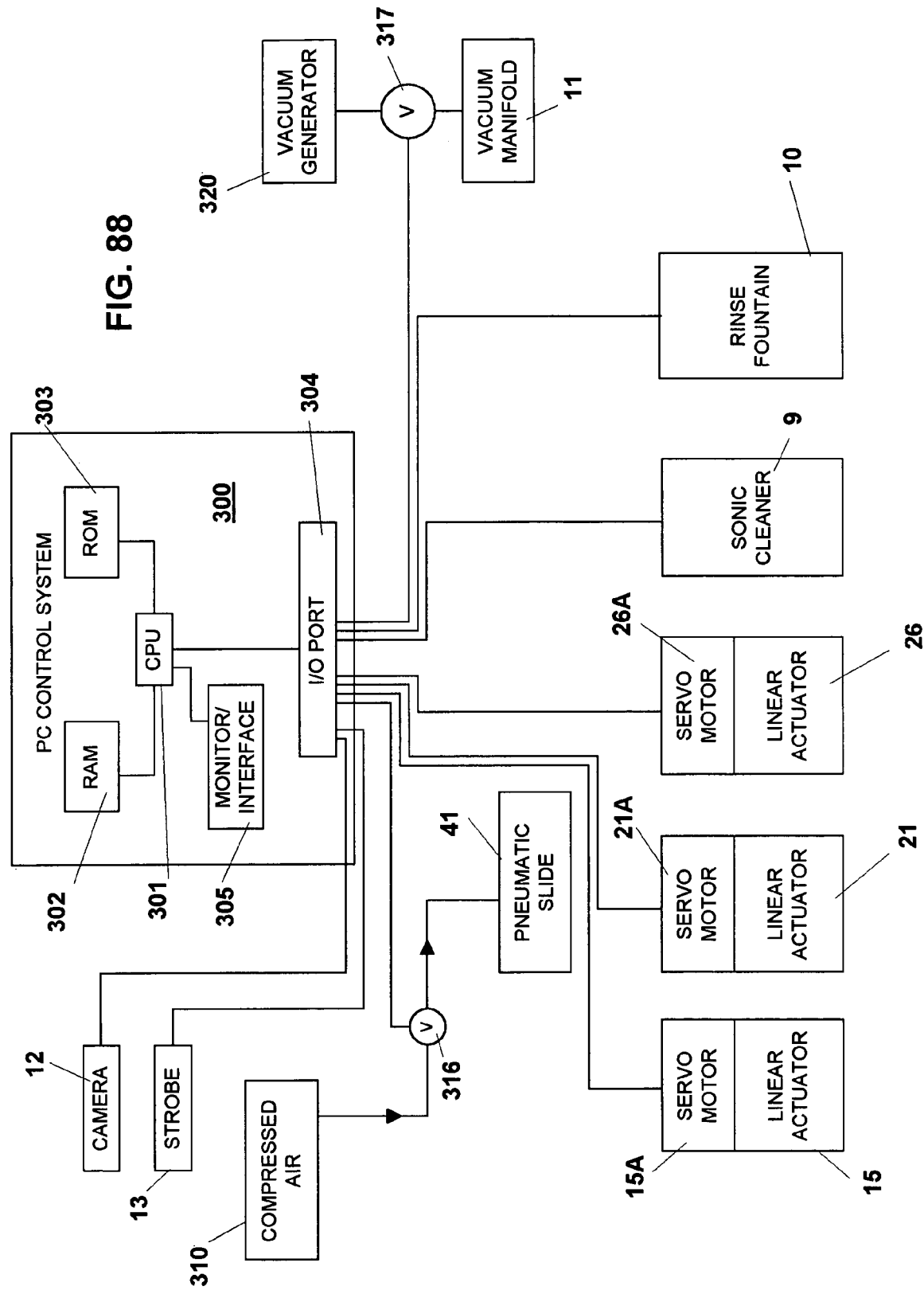

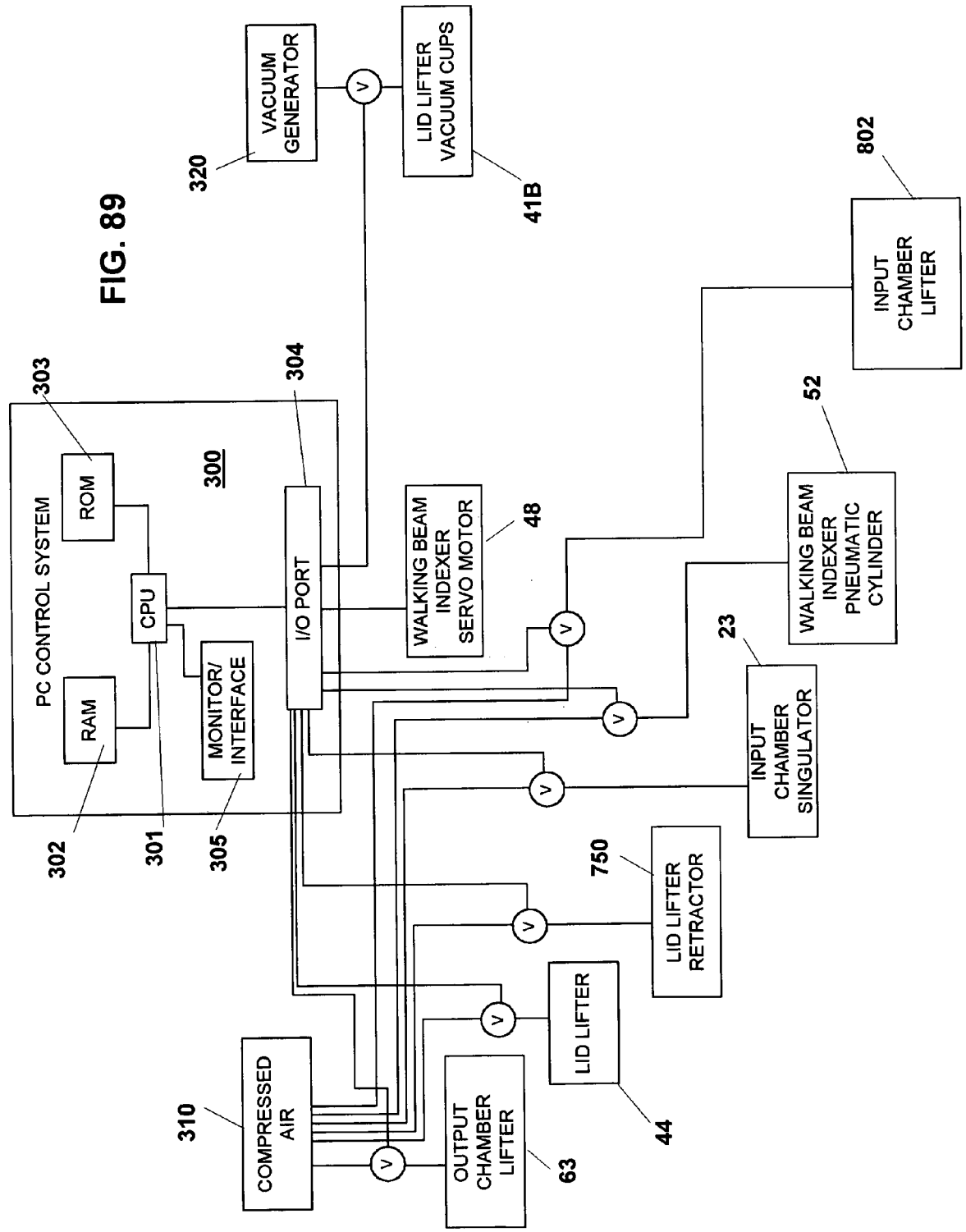

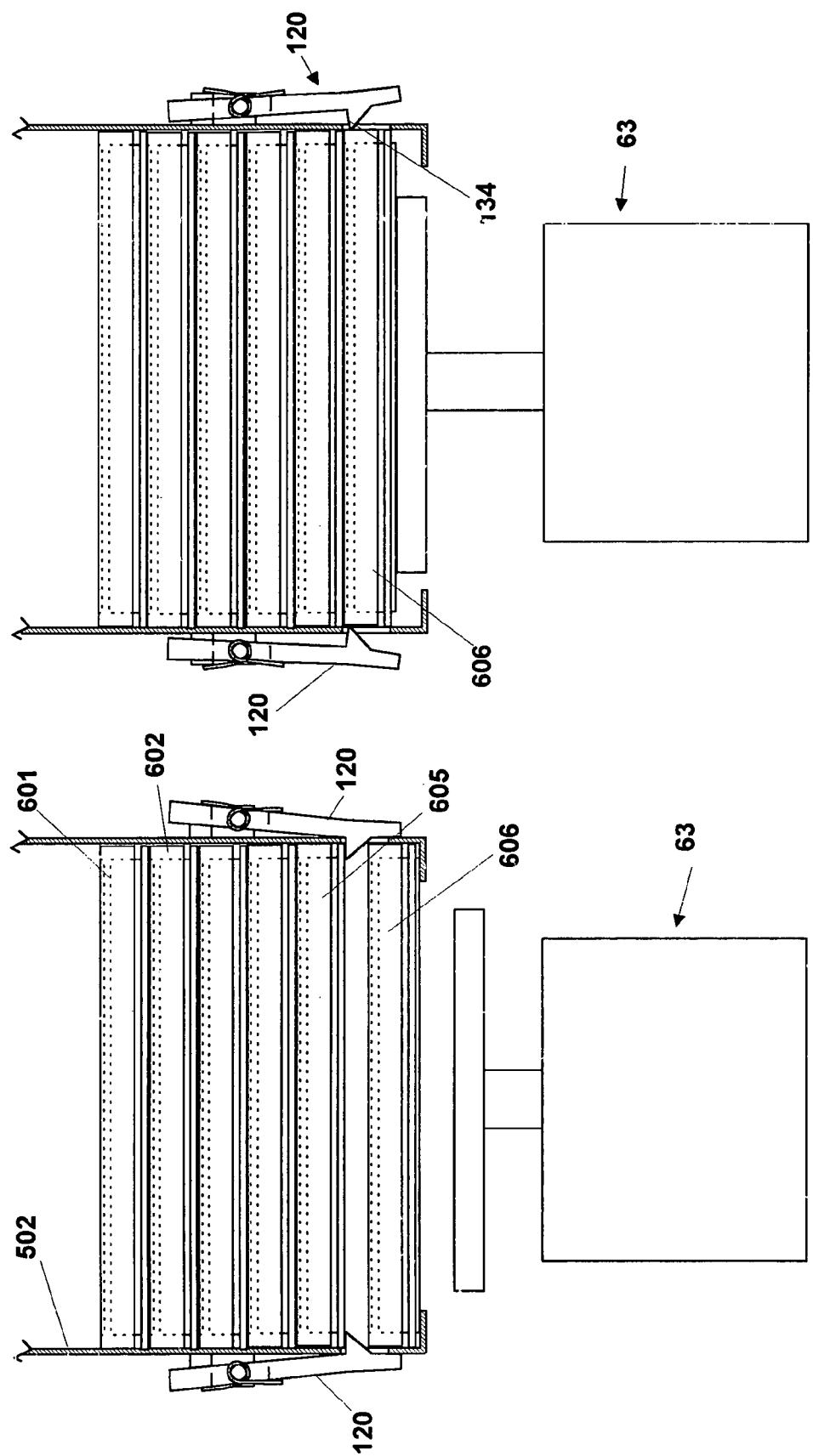

HIGH CAPACITY MICROARRAY DISPENSING

The present invention relates to automated microarray dispensing devices, more specifically it relates to high capacity automated microarray dispensing devices. The present invention is a continuation-in-part of U.S. patent application Ser. No. 09/411,943, filed Oct. 4, 1999, now U.S. Pat. No. 6,148,878, and is also a continuation-in-part of U.S. patent application Ser. No. 09/611,256, filed Jul. 6, 2000.

BACKGROUND OF THE INVENTION

Microarrays, also known as biochips, have recently become important in the study of genomics. The use of a microarray involves laying down an ordered array of genetic elements onto a solid substrate such as a slide. Depending on the application, a microarray may consist of genomic DNA, reverse-transcribed cDNA, or smaller chains of oligonucleotides as well as any preparatory substrates. The microarray is useful because it allows genetic analysis to take place on a massively parallel scale, wherein thousands of genes and markers can be scored in one experiment.

A microplate is a plate that may contain samples of genetic material in solution in small wells. A microarrayer, also known as a DNA array printer, is a high-capacity system used to print a microarray onto slides. Typically, a microarrayer is a specially built robotic platform designed to transfer solutions from the well of some type of microplate onto another surface for analysis. This process of depositing the liquid spot onto the slide is known as "spotting".

Recently, microarrayers have become extremely popular in laboratories because they add to the efficient productivity of the laboratory to be able to print samples onto slides accurately and rapidly. Affymetrix, Inc., with offices in Santa Clara, Calif., makes an automated arrayer called the 417 ARRAYER (Part No. 0-0001 and Part No. 0-0009). BioRobotics, with offices in Boston, Mass., produces two versions of an automated arrayer called the MICROGRID and MICROGRID II. GeneMachines, with offices in Menlo Park, Calif., makes an arrayer called the OMNIGRID (Model No. OGR-02). Packard Instrument Company with offices in Meriden, Conn. makes an automated arrayer called the BIOCHIP ARRAYER.

Although there are some differences between each of the above listed microarrayers, they are all similar in that they each spot microarrays in an automated fashion. However, there are significant problems with the prior art devices that detracts from their efficient operation.

A first problem arises due to the fact that as blank slides are cycled through prior art microarrayers, they can become askew or positioned improperly underneath dispensing tips. This problem results in spots being positioned improperly on the slides. A second problem can arise even if the slide is positioned correctly under the dispensing tips. It is possible for the spot to be deposited in the correct position, but be of poor quality and therefore useless as far as experimentation purposes.

Up to now, the only way to deal with these problems was to have a human operator visually monitor and inspect the microarrayer during its operation or inspect the samples after they come off the machine. This solution is an unacceptable waste of human effort. The BIOCHIP ARRAYER made by Packard Instrument Company has attempted to deal with the problem of monitoring the spotting process. However, it has only limited verification functionality with its integrated camera. This means that it verifies whether or not a spot has been dispensed, without any quality inspection to analyze whether that spot was good or bad.

Another problem with prior art automated microarrayers is that they have limited handling capacity. For example, once solution has been removed from a microplate and spotted on slides, the depleted microplate needs to be replaced with a new microplate. An operator typically has had to manually replace the depleted microplate with a new microplate before the microarrayer could continue operating.

What is needed is a better microarrayer with high capacity capability.

SUMMARY OF THE INVENTION

The present invention provides a high capacity microarrayer for spotting solution onto slides in an automated microarray dispensing device. A microplate indexing device automatically moves, in sequence, a plurality of microplates to a solution removal area. A dispense head accesses each microplate at the solution removal area to remove solution from the microplate. The dispense head then moves to a slide positioning station to spot slides at the slide positioning station. In a preferred embodiment of the present invention, the microplate indexing station has at least one input stacking chamber for stacking microplates, and at least one output stacking chamber for stacking microplates. A walking beam indexer is disposed between the at least one input stacking chamber and the at least one output stacking chamber. The walking beam indexer is for moving microplates from said at least one input stacking chamber to said at least one output stacking chamber. While at the solution removal area, a lid lifter lifts the lid off each microplate to permit the microplate to be accessed by the dispense head for solution removal. After the solution is removed, the lid lifter replaces the lid. In another preferred embodiment, there is at least one light source capable of illuminating the slides, and at least one camera operating in conjunction with the at least one light source. The at least one camera is capable of acquiring and transmitting slide image data to a computer. The computer is programmed to receive the slide image and analyze it. The computer will then generate post analysis data based on the analysis of the slide image data. The post analysis data is available for improving the spotting of the solution onto the slides. In a preferred embodiment, the slide image data includes information relating to slide alignment, information relating to spot quality, and slide identification information. In a preferred embodiment, the analysis of the information relating to slide alignment enables the computer to make automatic adjustments to the relative positions of the at least one dispense head and the slides to increase the accuracy of the spotting. In a preferred embodiment, the analysis of the information relating to spot quality identifies a spot as pass or fail. An operator is then able to rework the spot. In a preferred embodiment, the analysis of the slide identification information enables the computer to track each slide.

BRIEF DESCRIPTION OF THE DRAWINGS

FIGS. 3–32 illustrate the sequence of operation of a preferred embodiment of the present invention.

FIG. 34A shows the rework dispense head in the up position.

FIG. 34B shows the rework dispense head in the down position.

FIG. 34C shows a slide with a 2D bar code.

FIGS. 39A and 39B show the reworking of a slide for a preferred embodiment of the present invention.

FIGS. 44A–44B show the microplate indexing station.

FIGS. 45–76 show a detailed sequence of operation of the third preferred embodiment.

FIGS. 79–86 show a detailed sequence of operation of the third preferred embodiment.

FIGS. 88 and 89 show some major components of the third preferred embodiment.

FIG. 92 shows a detailed side view of a preferred output chamber.

FIGS. 92–95 show a sequence illustrating a preferred method for stacking microplates in the output chamber.

DETAILED DESCRIPTION OF THE PREFERRED EMBODIMENT

First Preferred Embodiment

Figure 1:
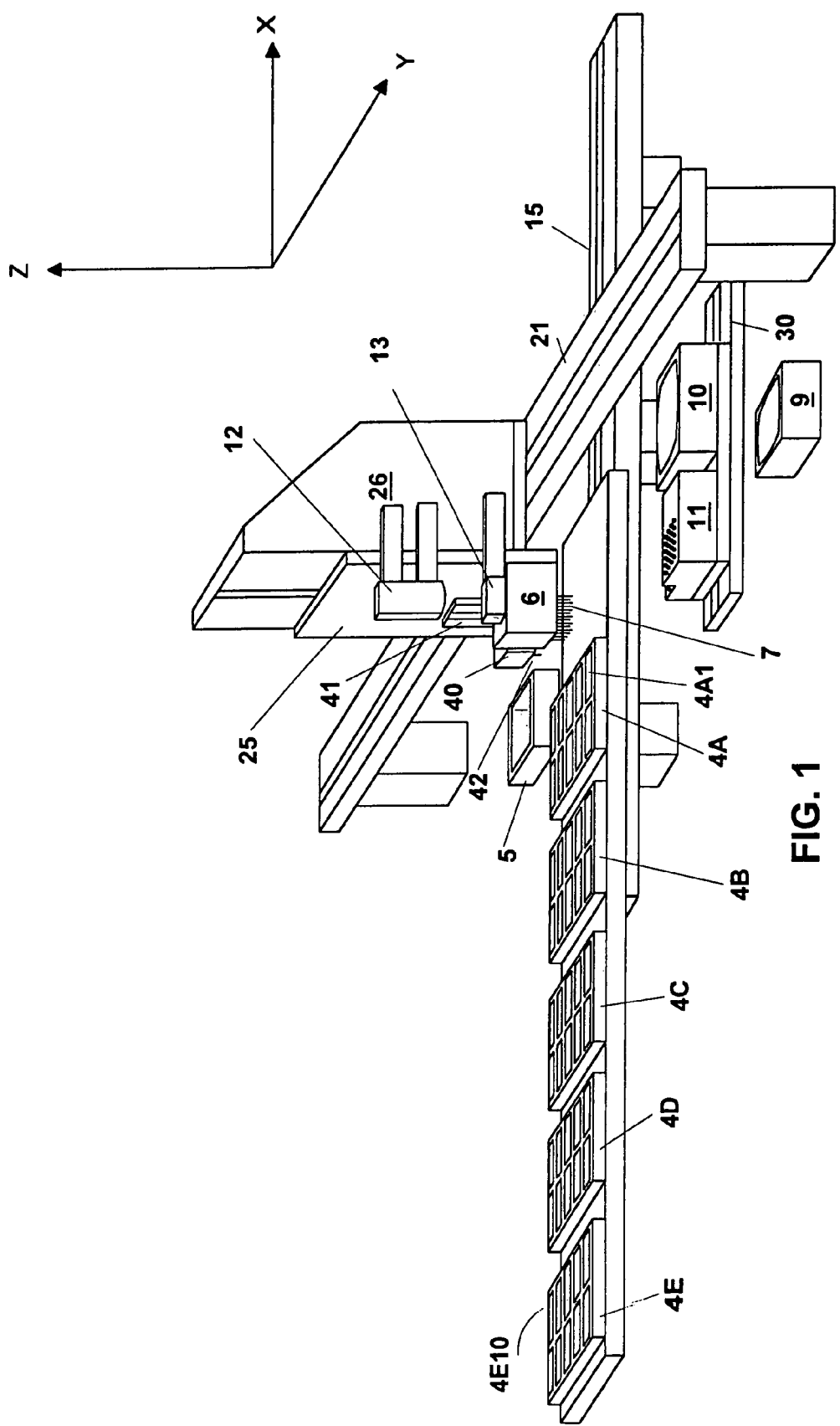
FIG. 1 shows the major components of a preferred embodiment of the present invention.

A detailed description of a first preferred embodiment of the present invention can be described by reference to FIGS. 1–38B. During the operation of the present invention, solution from reservoir plate 5 is automatically deposited onto an array of fifty blank slides 4A1–4E10 located on locating plates 4A–4E (see FIG. 1). An operator is able to select via a computer interface whether dispense tip 42 (located underneath dispense head 40) or a 4×6 array of dispense tips 7 (located underneath dispense head 6) will be used to make the deposits onto slides 4A1–4E10. In the preferred embodiment, dispense tips 7 and 42 are quill type dispense tips. Locating plates 4A–4E are mounted on linear actuator 15 so that they can move along the x-axis. Linear actuator 26 is mounted on linear actuator 21 so that linear actuator 26 can move along the y-axis. Dispense heads 6 and 40 are mounted on linear actuator 26 so that they can move along the z-axis. Camera 12 with strobe light 13 is focused so as to permit recording of the deposition process and functions to permit verification of slide identification information and to permit verification of proper deposition of solution on the slides. Periodically, during the cycle, the dispense tips are cleaned in sonic cleaner 9, rinsed in rinse fountain 10, and then dried in vacuum manifold 11. After the solution has been deposited onto the slides, the operator can retrieve locating plates 4A–4E containing slides 4A1–4E10 from the position shown in FIG. 2.

Sequence of Operation of a Preferred Embodiment

FIGS. 3–32 illustrate the sequence of operation of a preferred embodiment of the present invention.

Figure 37:
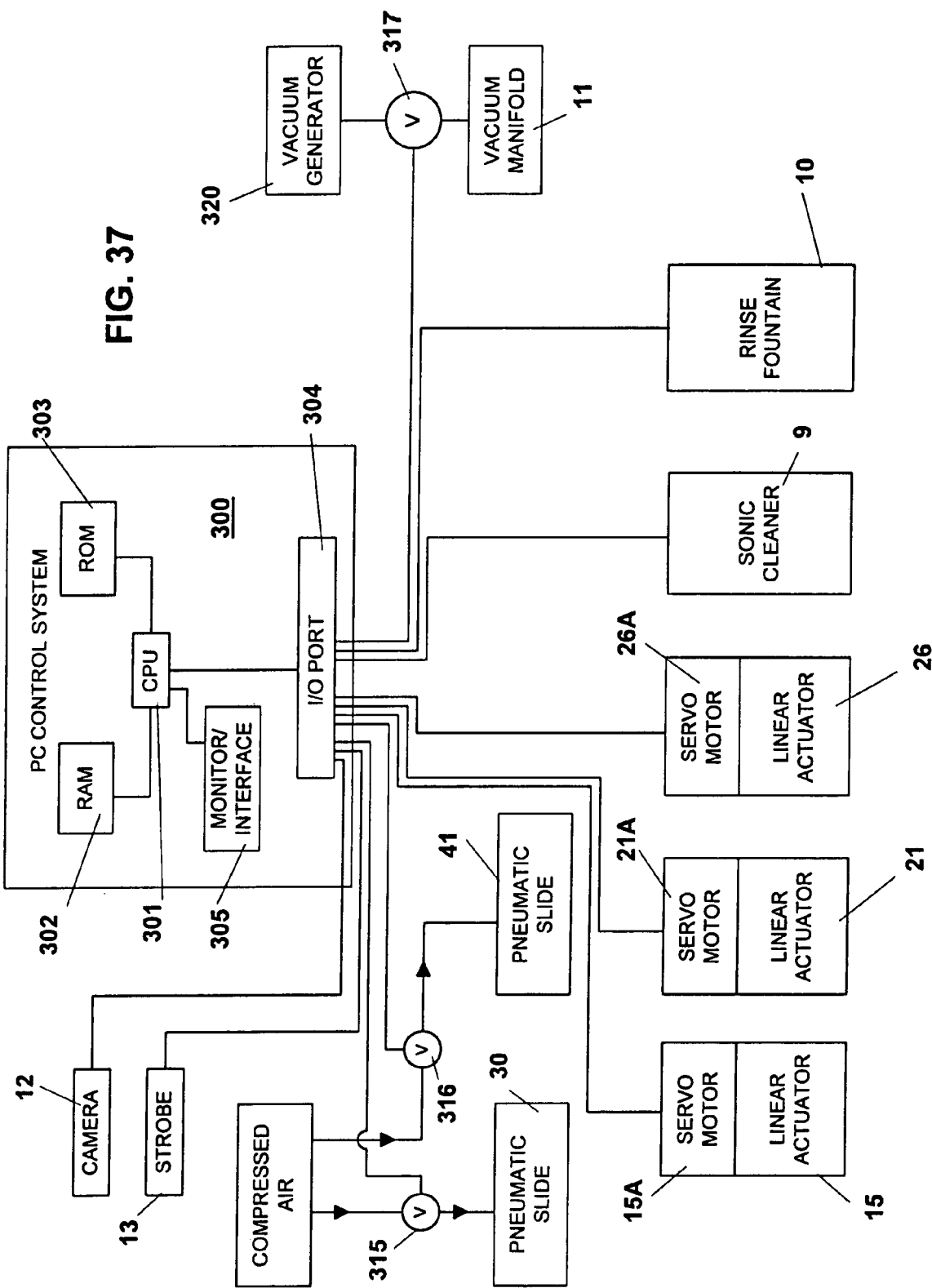
FIG. 37 shows the major components of a preferred embodiment of the present invention.
Figure 38A:
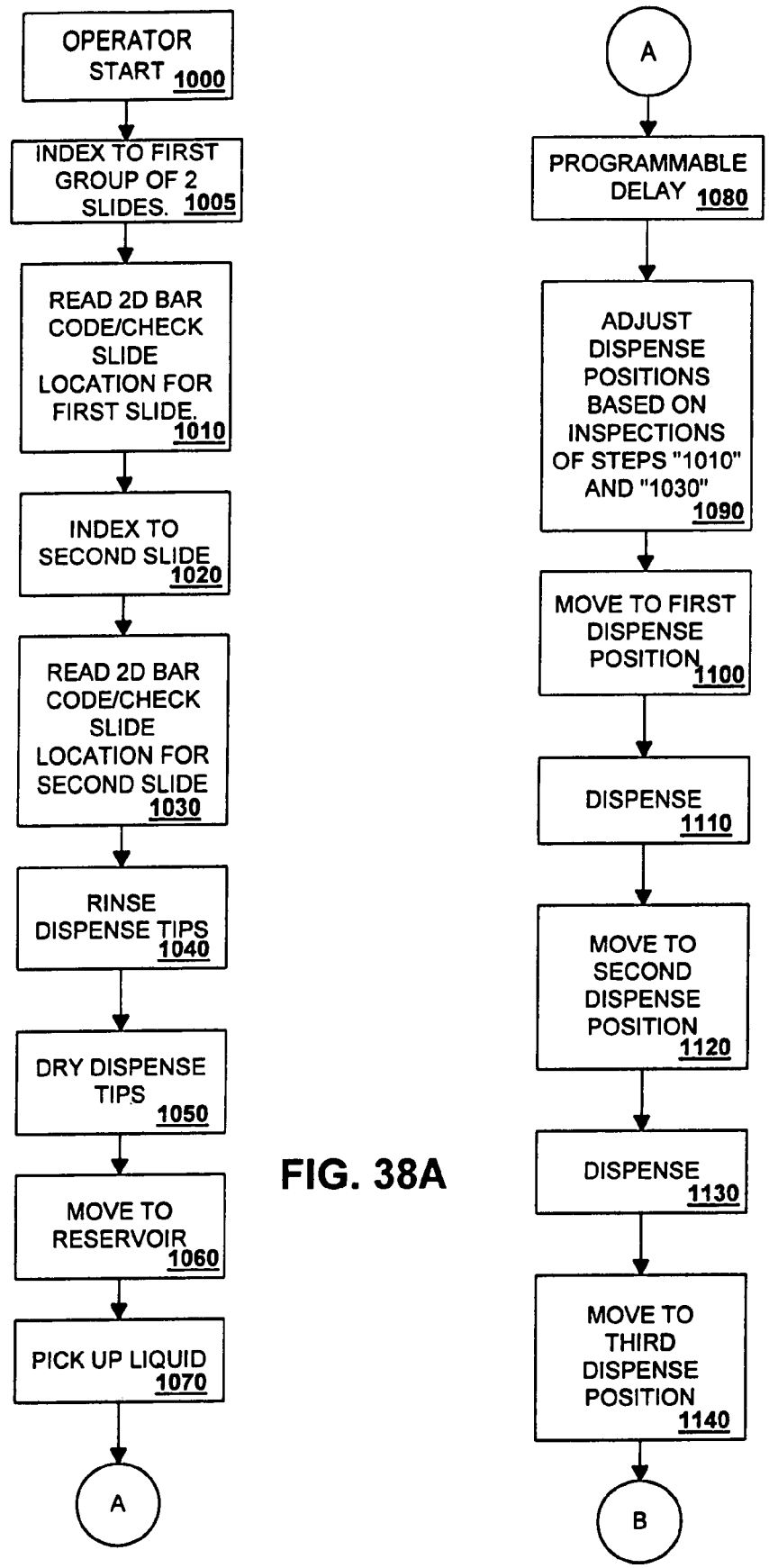
FIGS. 38A and 38B show a flowchart for the programming of a preferred embodiment of the present invention.
Figure 38B:
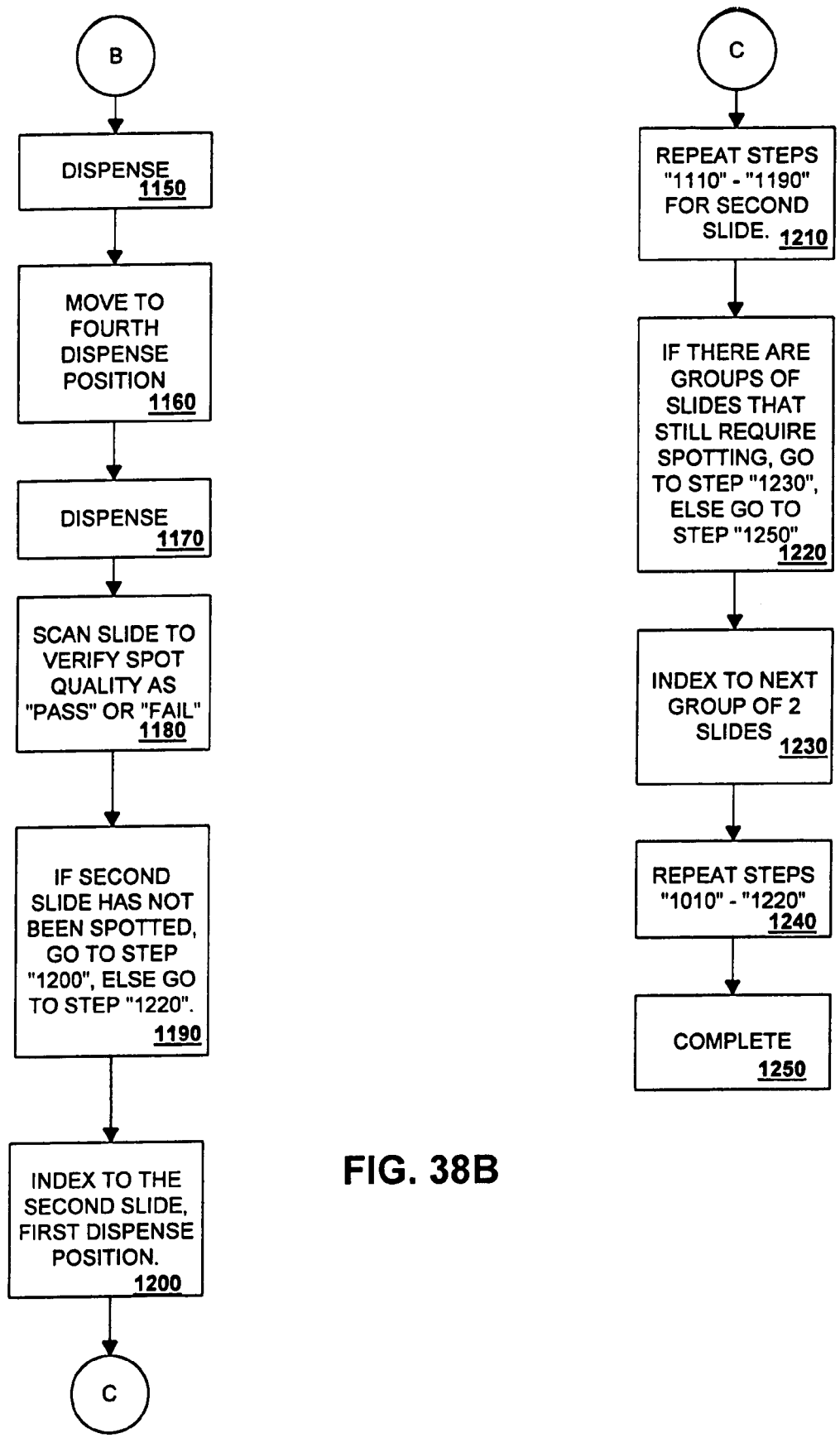

In a preferred embodiment of the present invention, the operation of the components is controlled by PC control system 300, as shown in FIG. 37. FIGS. 38A–38E show a flowchart representing preferred programming of PC control system 300 and corresponds to the sequence illustrated in FIGS. 3–32.

Figure 3:
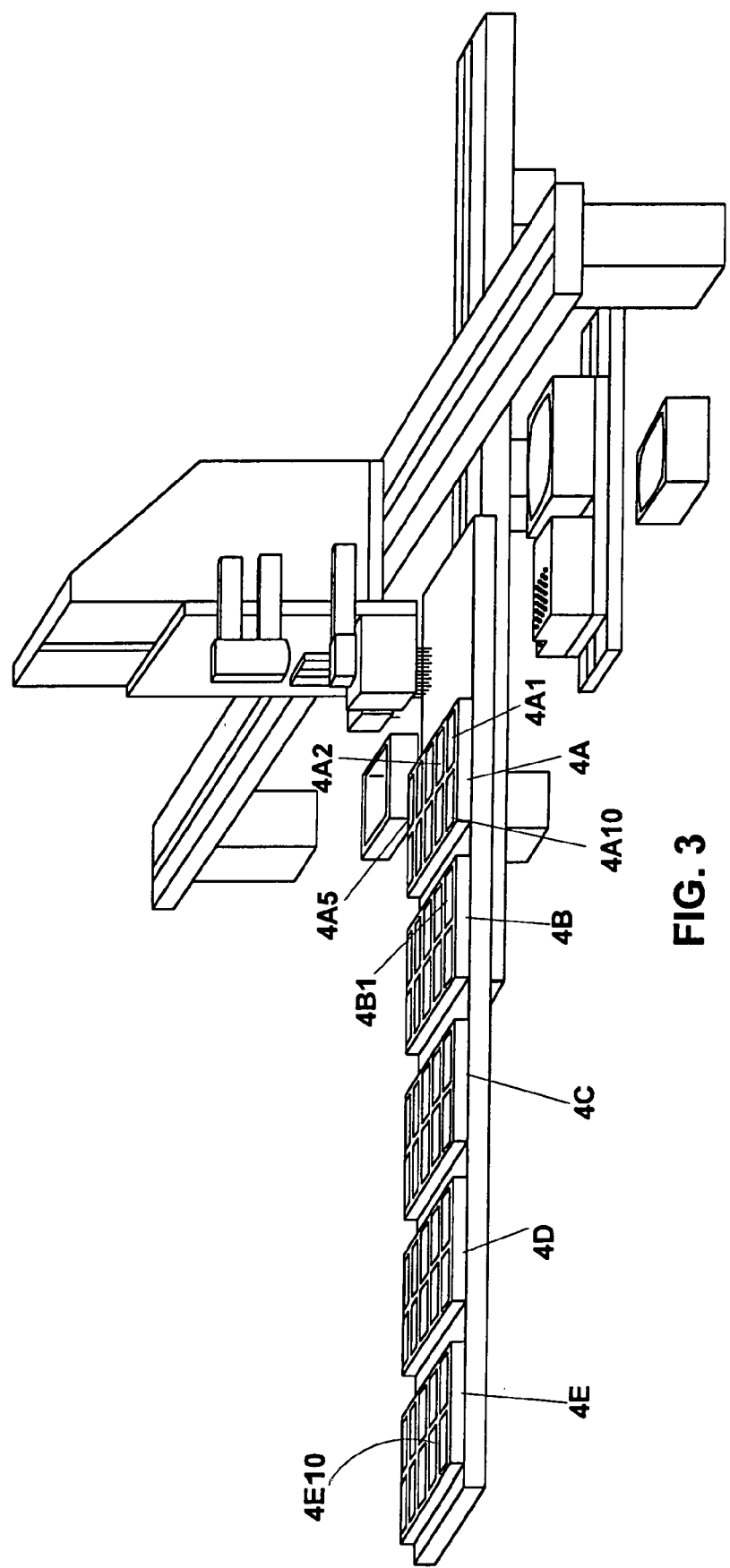
Figure 16B:
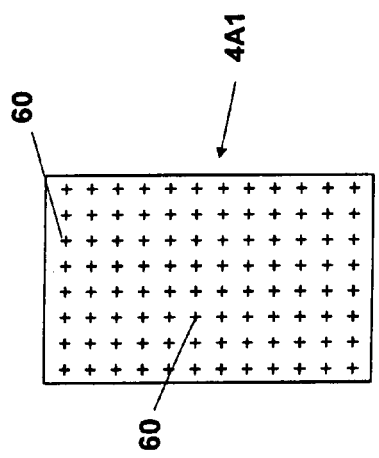

As shown in FIG. 3, an operator places five locating plates 4A–4E each having ten clean, blank slides 4A1–4E10 on platform 2. In a preferred embodiment of the present invention, slides 4A1–4E10 are made by Sequonem with offices in San Diego, Calif. A preferred slide is shown in FIG. 16B. It has ninety-six etched dispense positions 60 and has its own unique 2D bar code 65 for identification purposes.

Figure 4:
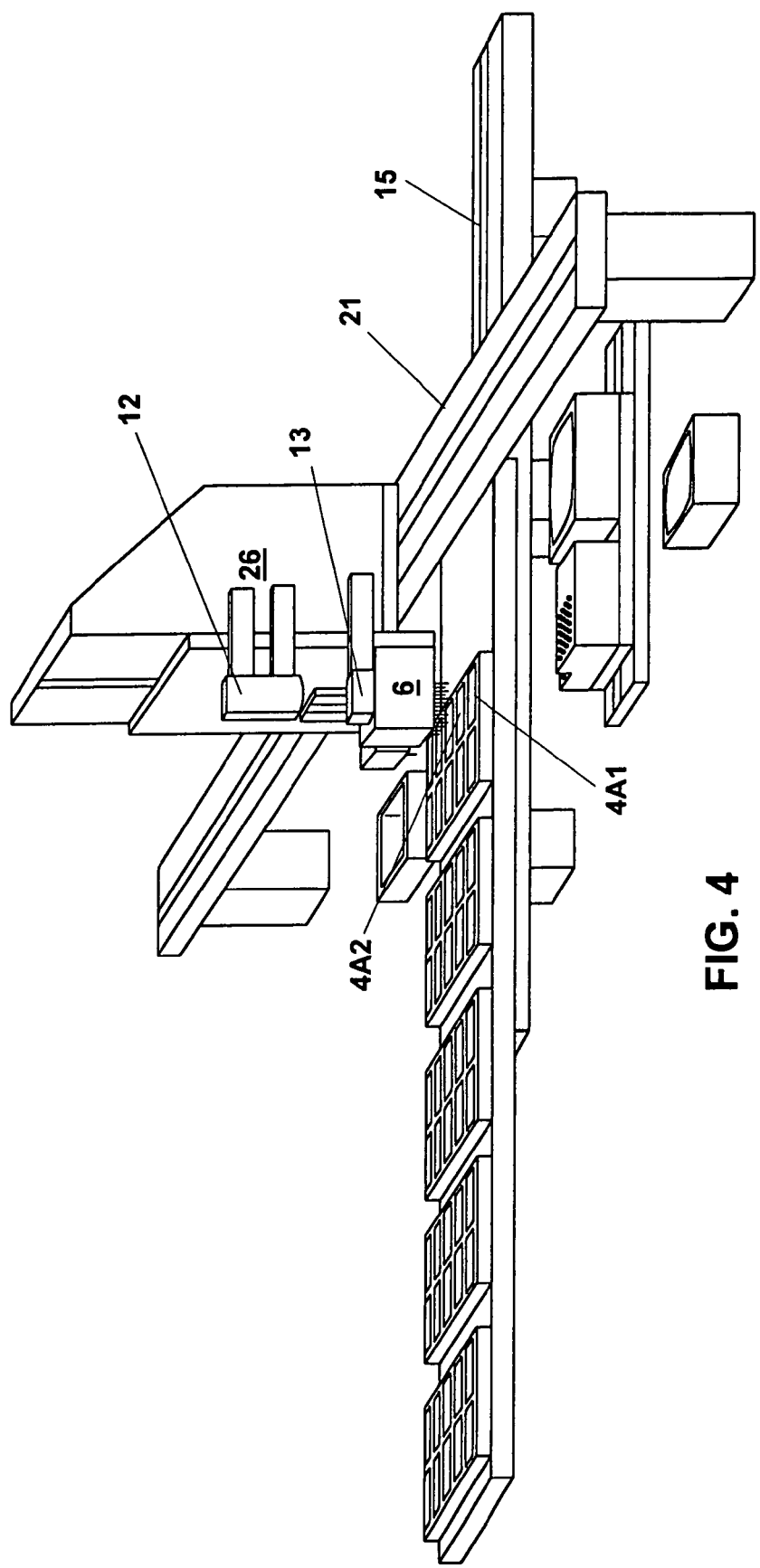

As shown in FIG. 4, linear actuator 15 moves platform 2 so that slide 4A1 is underneath the dispense head 6. Dispense head 6 is positioned directly above slide 4A1. Using camera 12 and the strobe light 13, an image is acquired of slide 4A1. The camera reads the bar code and inspects the positioning and alignment of slide 4A1 on locating plate 3A. The software then analyzes the position data and stores the information. The information stored and will be used later to adjust the positions of slide 4A1 and dispense head 6 to ensure accurate placement of the solution on the slide.

Figure 5:
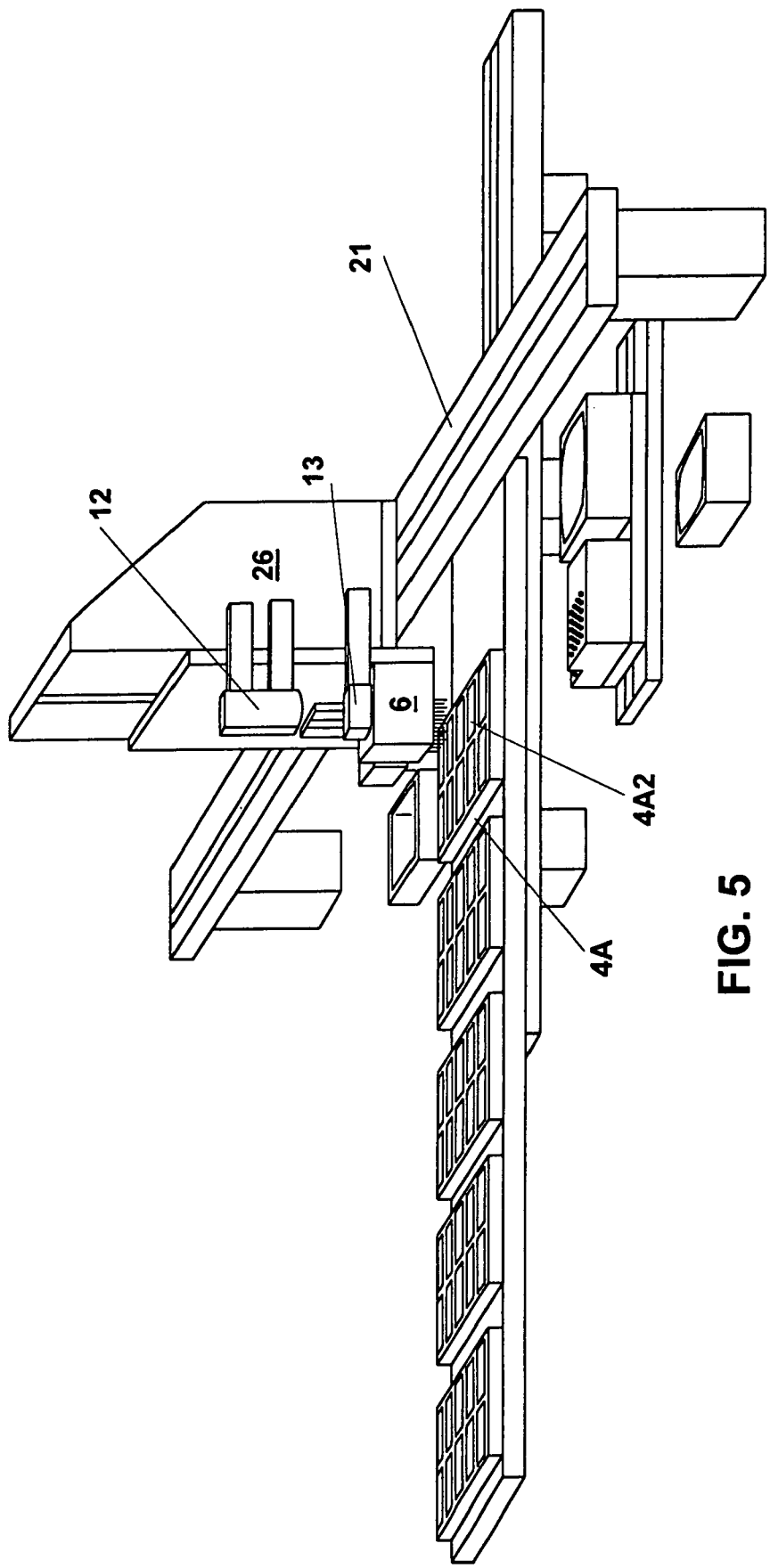

After camera 12 has acquired the image of slide 4A1, linear actuator 26 is moved via linear actuator 21 to the position shown in FIG. 5 so that dispense head 6 is directly above slide 4A2. Using camera 12 and the strobe light 13, an image is acquired of slide 4A2. As with slide 4A1, camera reads the bar code and inspects the positioning and alignment of slide 4A2 on locating plate 4A. The software then analyzes the position data and stores the information. The information stored and will be used later to adjust the positions of slide 4A2 and dispense head 6 to ensure accurate placement of the solution on the slide.

Figure 6:
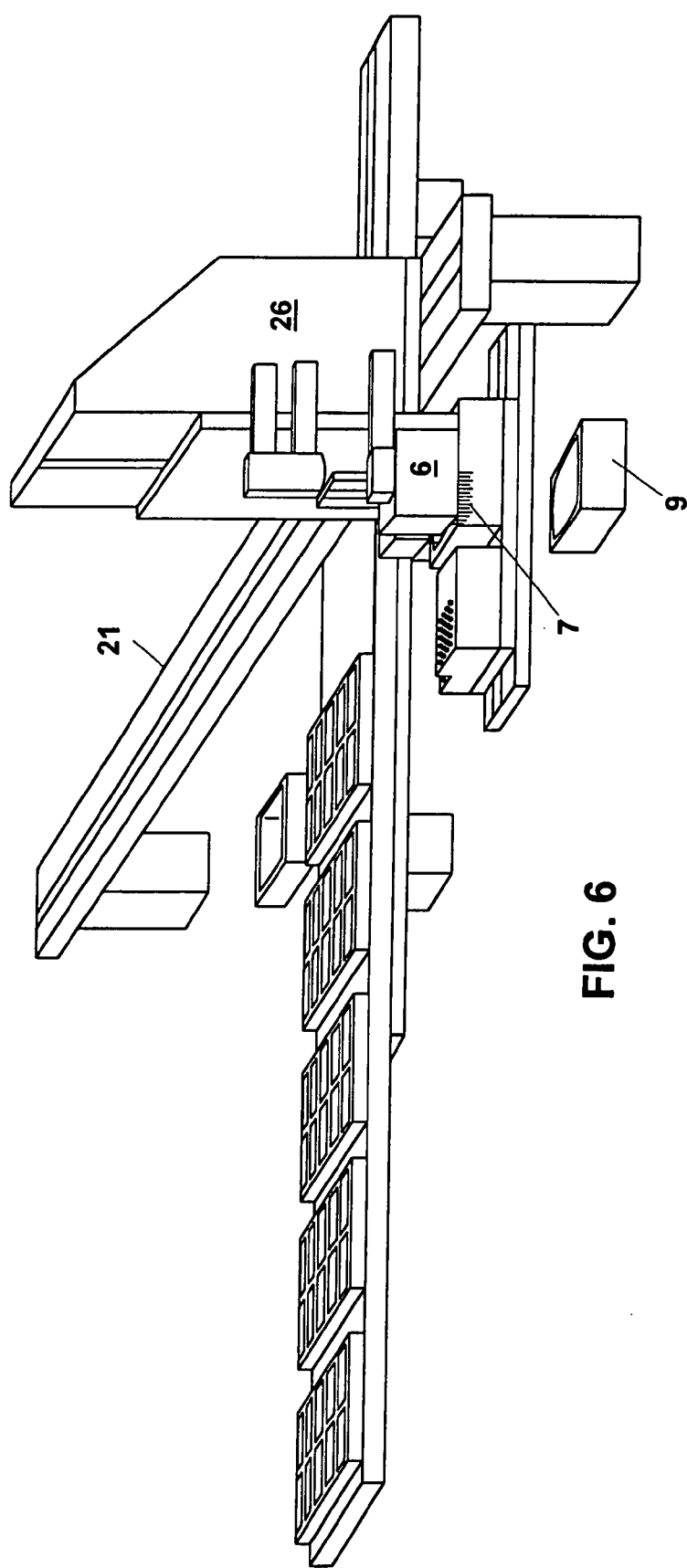

Linear actuator 26 is then moved via linear actuator 21 to the position shown in FIG. 6 so that dispense head 6 is directly above sonic cleaner 9.

Figure 7:
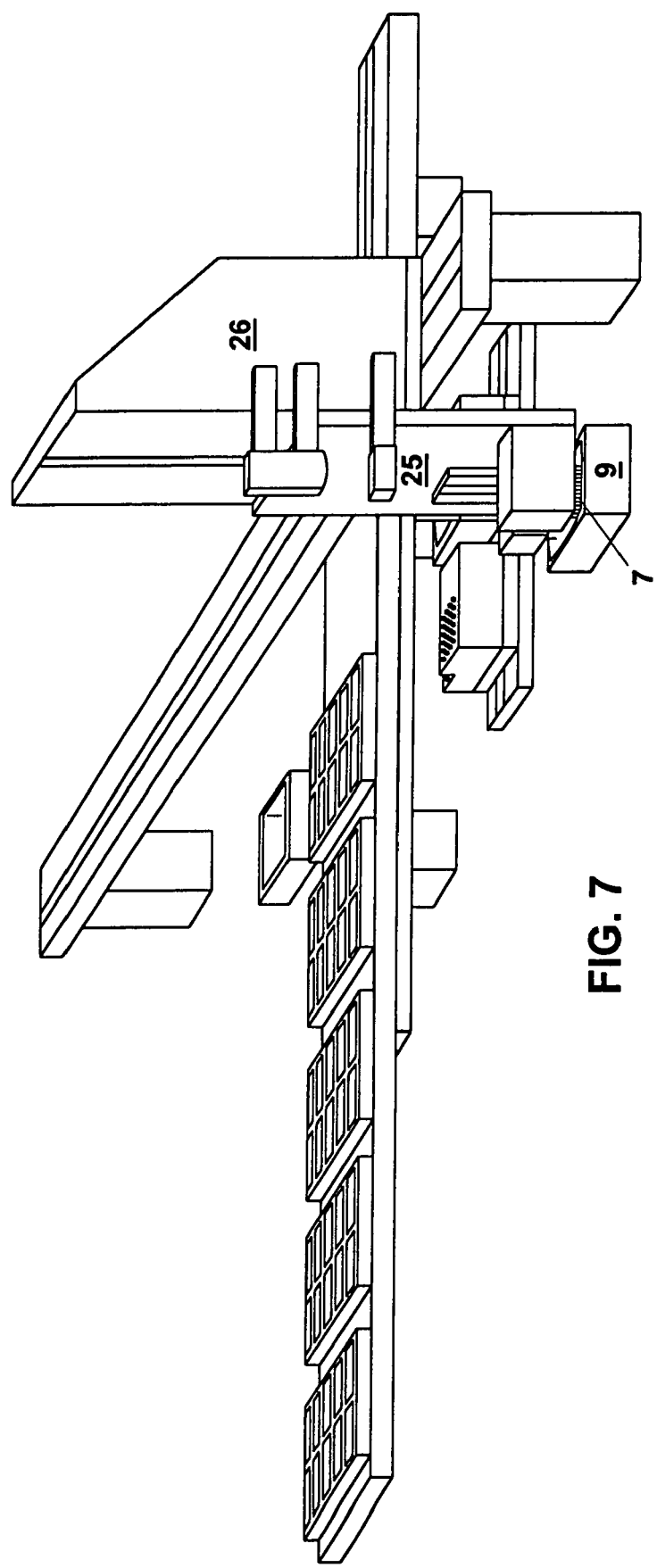
Figure 8:
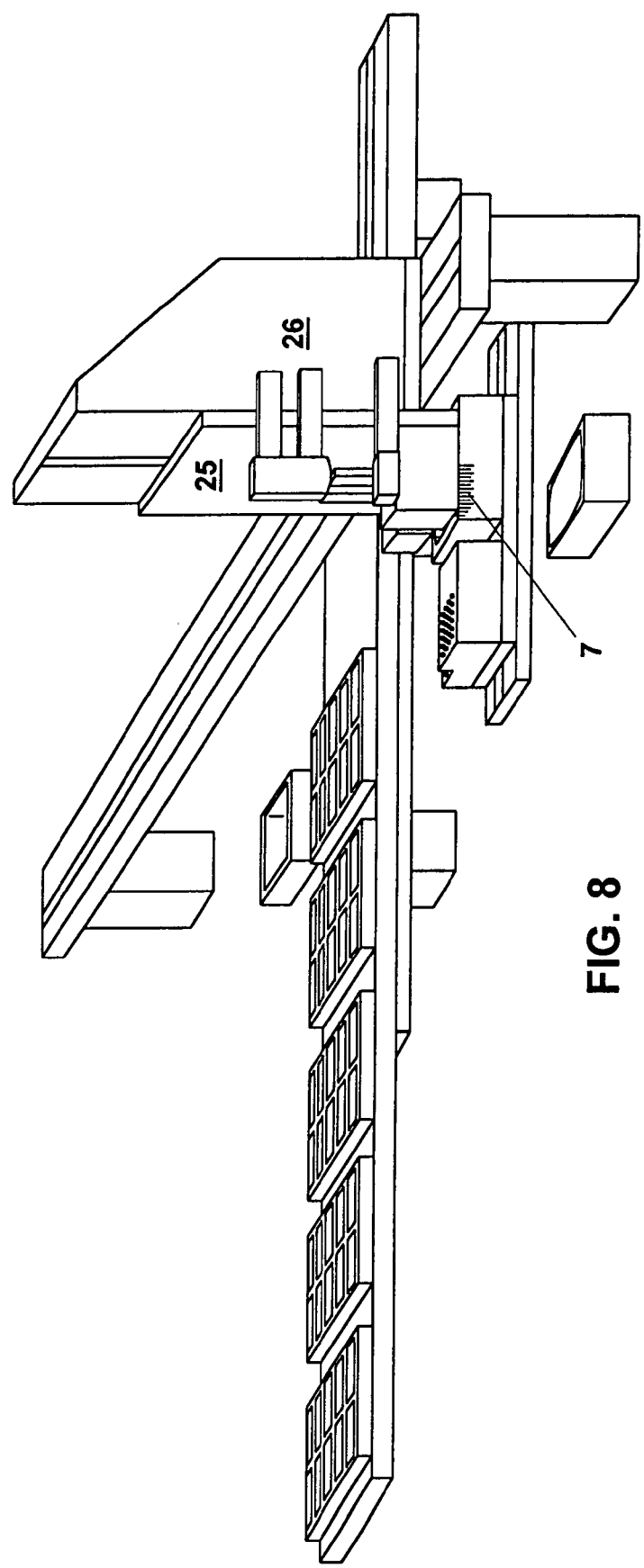

As shown in FIG. 7, mounting plate 25 moves downward via linear actuator 26 so that dispense tips 7 are dipped in sonic cleaner 9 for a programmable time period while the cleaner is turned on. When finished, mounting plate 25 moves upward as shown in FIG. 8.

Figure 9:
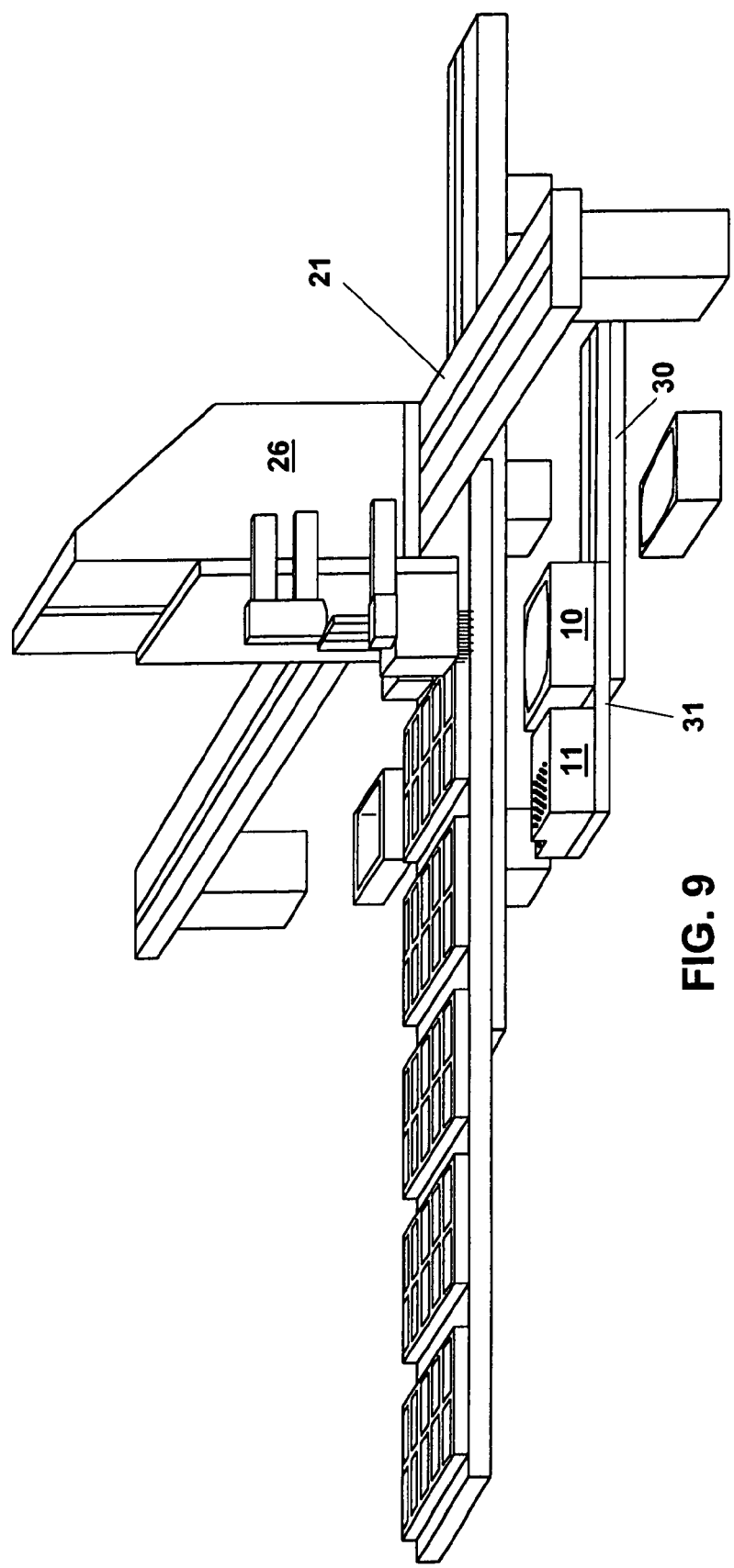

Then, as shown in FIG. 9, platform 31 moves to the left via pneumatic slide 30, thereby moving rinse fountain 10 and vacuum manifold 11 to the left. Linear actuator 26 is moved via linear actuator 21 back so that it is directly above rinse fountain 10.

Figure 10:
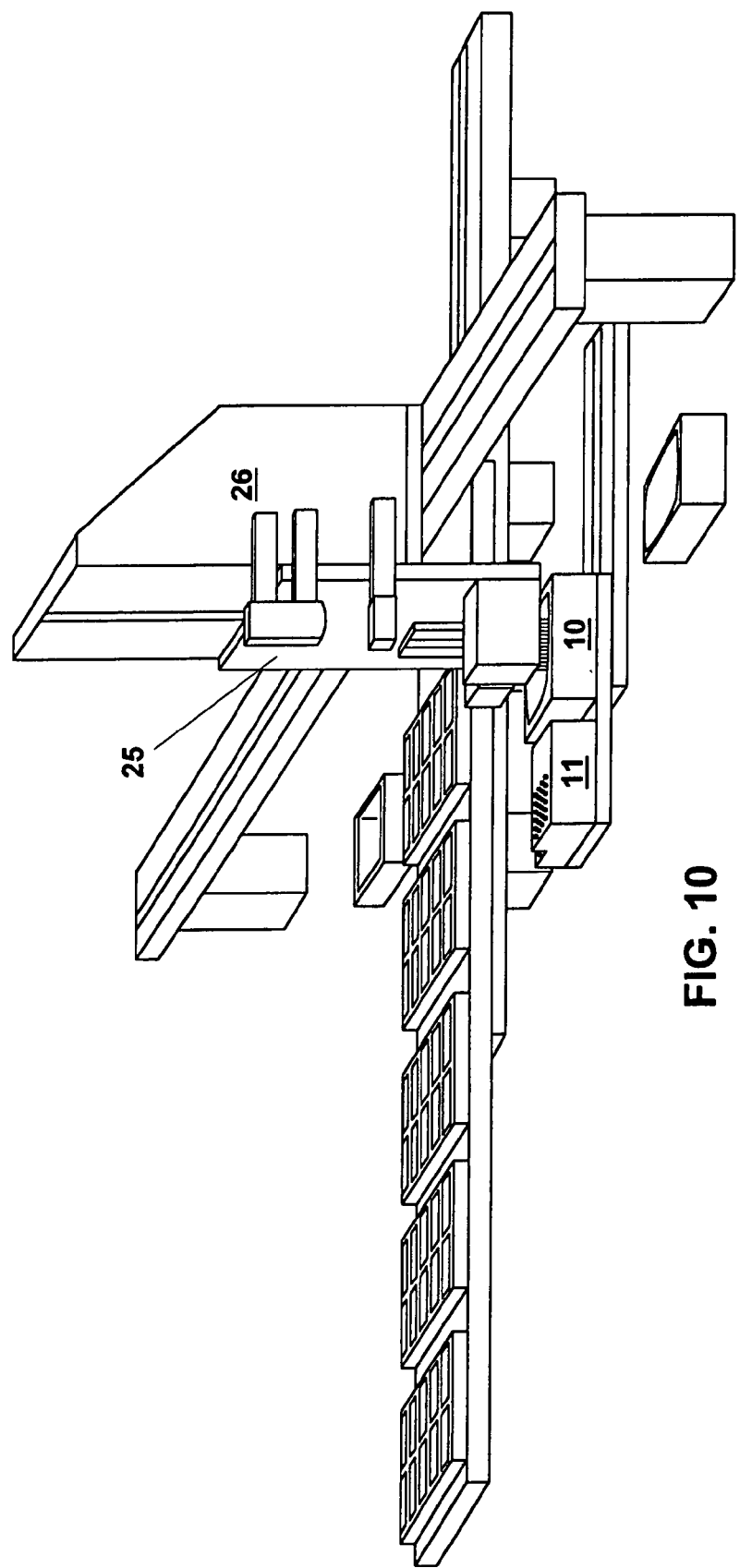

As shown in FIG. 10, mounting plate 25 moves downward via linear actuator 26 so that tips 7 are dipped in rinse fountain 10 for a programmable time period while the fountain is turned on.

Figure 11:
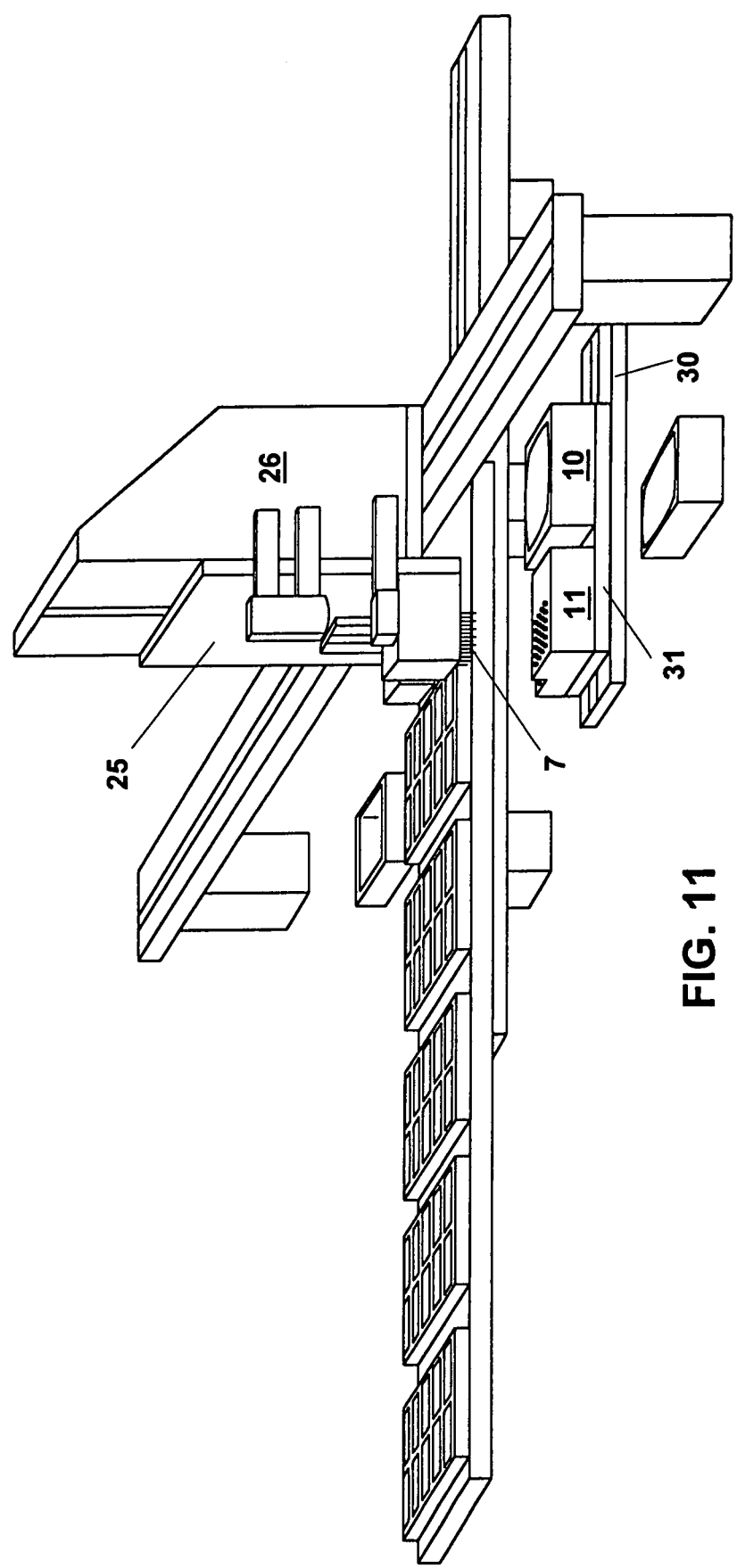

After rinsing, mounting plate 25 moves upward via linear actuator 26, as shown in FIG. 11. Platform 31 moves to the right via pneumatic slide 30, thereby moving rinse fountain 10 and vacuum manifold 11 to the right.

Figure 12:
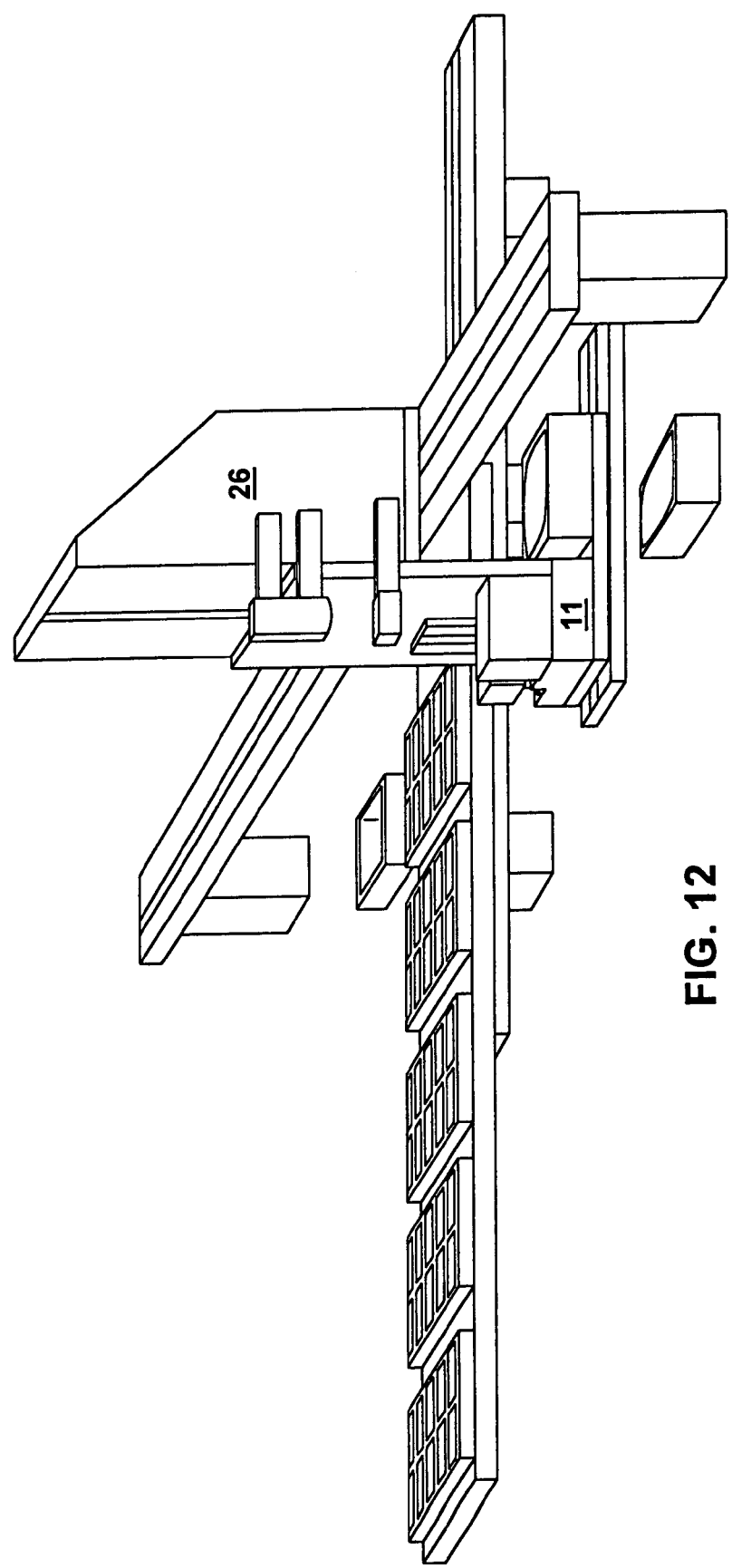

As shown in FIG. 12, dispense tips 7 are then lowered into the vacuum manifold 11 via linear actuator 26 and the vacuum is turned on for a programmable time period, thereby drying dispense tips 7. This cleaning cycle can be set by the user, via the computer interface, to be repeated as many times as necessary.

Figure 13:
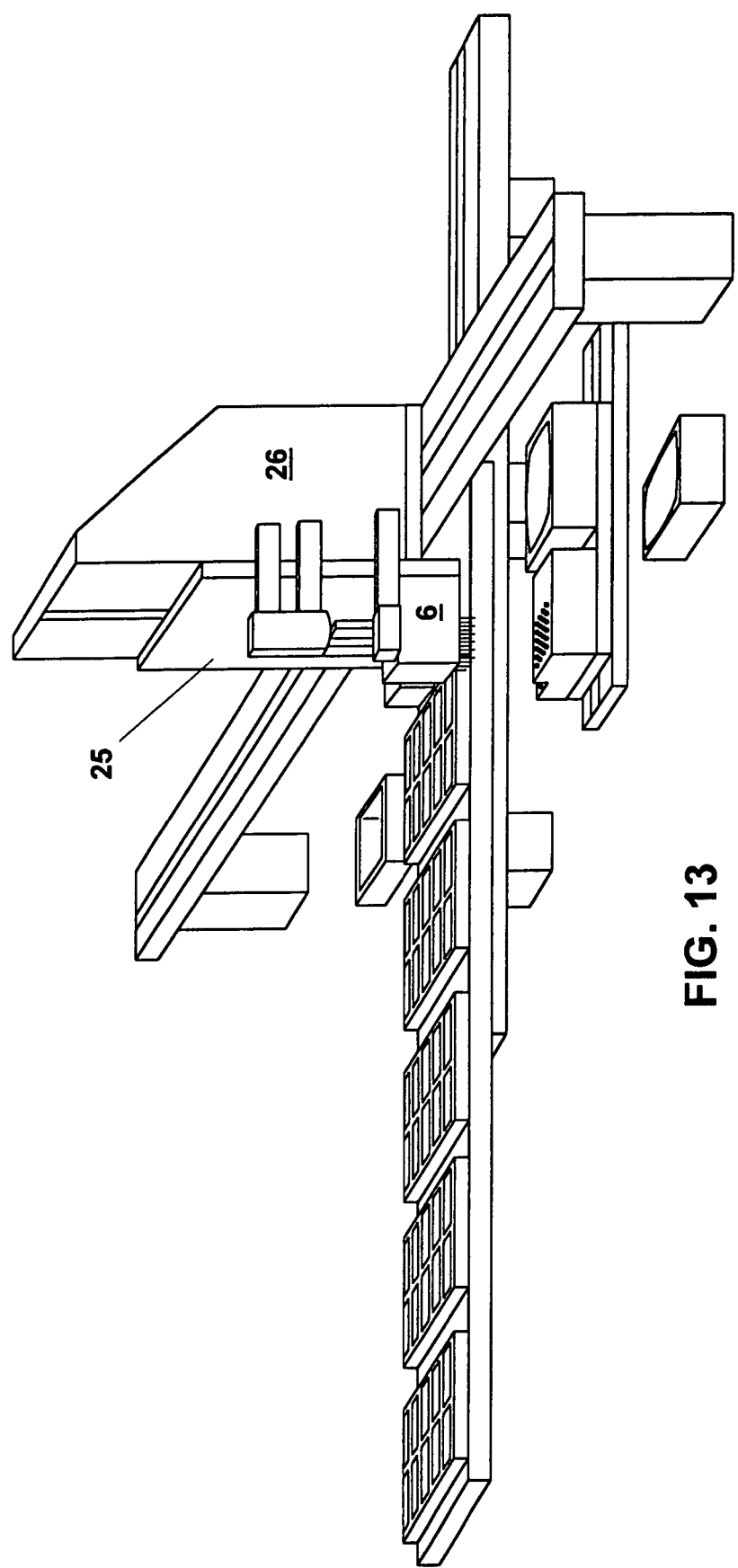
Figure 14:
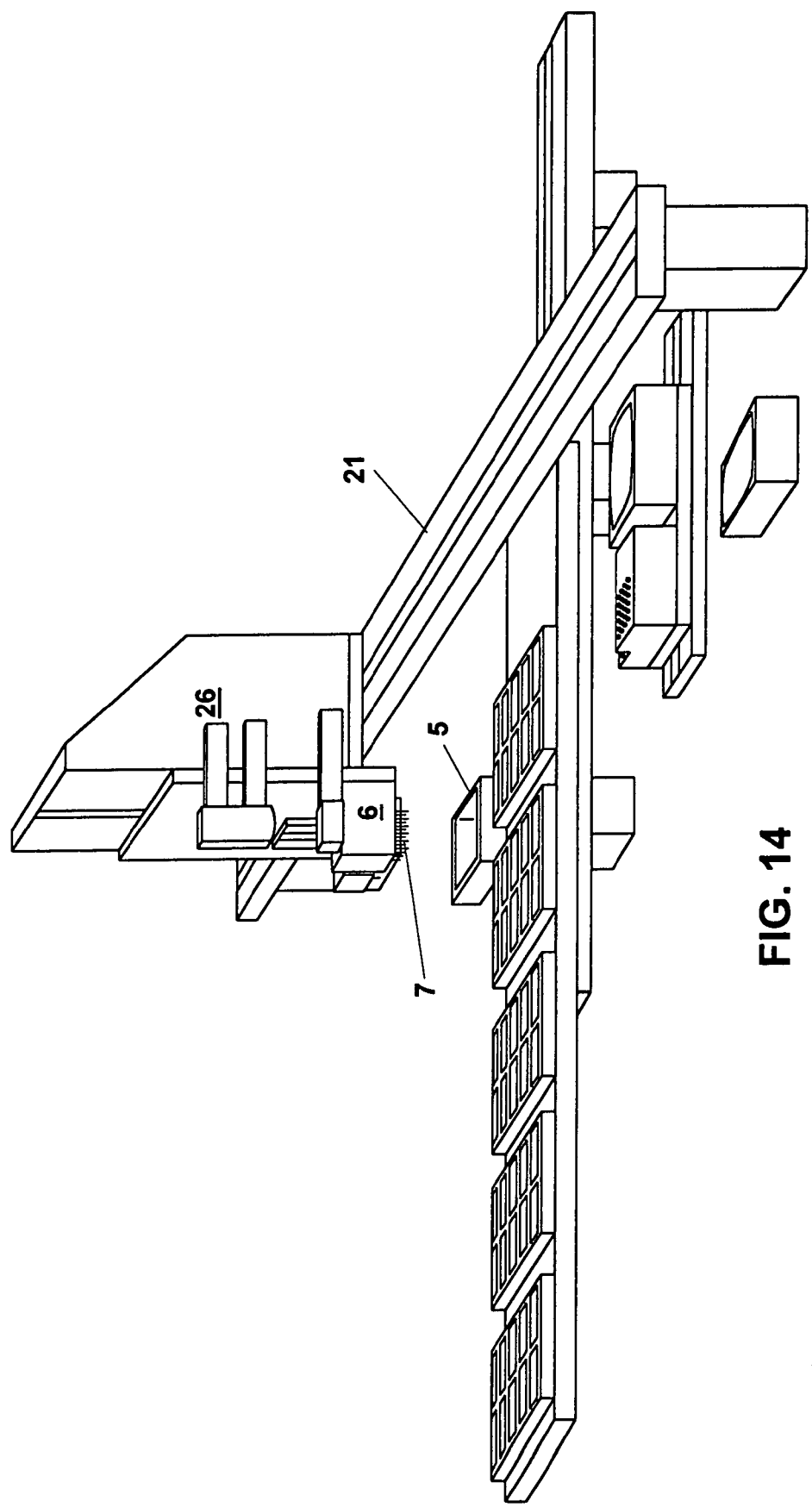

Mounting plate 25 is then raised via linear actuator 26 as shown in FIG. 13. Linear actuator 26 is then moved via linear actuator 21 so that dispense head 6 is directly above reservoir plate 5, as shown in FIG. 14.

Figure 15:
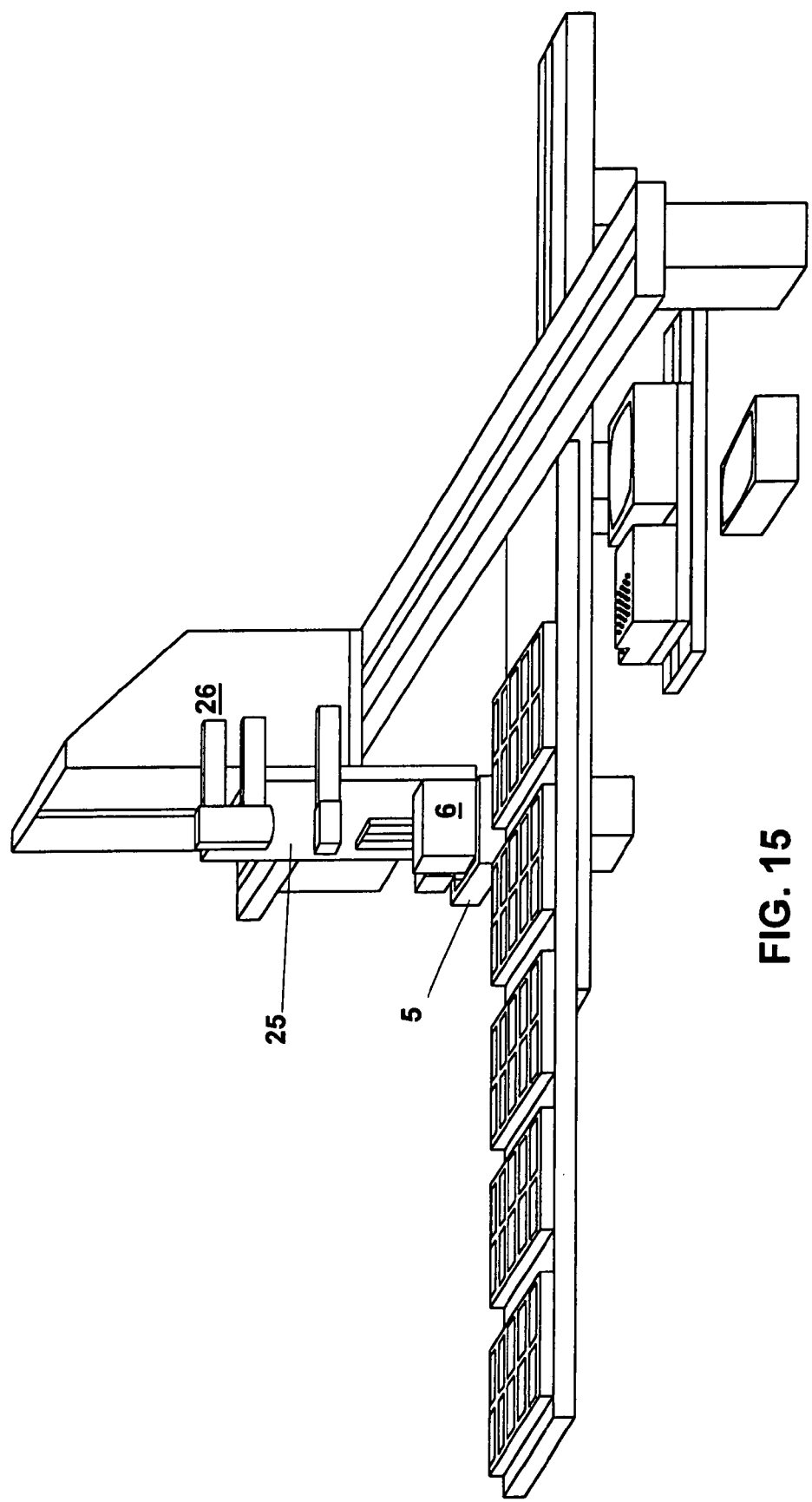

Mounting plate 25 is then lowered via linear actuator 26 so that tips 7 are dipped into the solution contained in reservoir plate 5, as shown in FIG. 15. While in reservoir plate 5, dispense tips 7 pick up some of the solution to be dispensed.

Figure 16A:
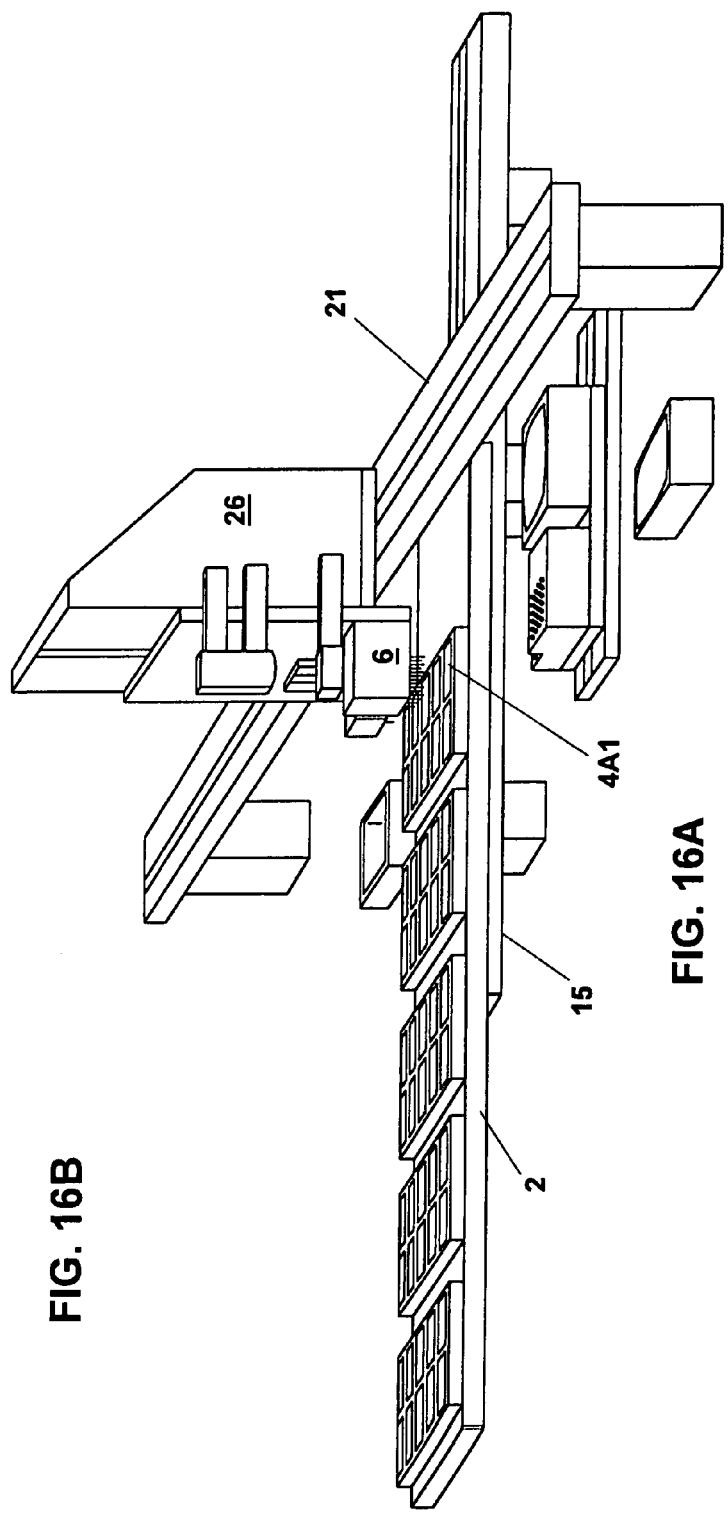

Linear actuator 26 then moves to the first dispense position shown in FIG. 16A so that dispense head 6 is above slide 4A1. Based on the earlier positioning data regarding slide 4A1 (see discussion of FIG. 4), linear actuator 21 makes minute positioning adjustments to linear actuator 26 and linear actuator 15 makes minute positioning adjustments to platform 2 in order to accurately position dispense head 6 over slide 4A1 at the first dispense position.

FIG. 16B shows a top view of a blank slide 4A1. In this preferred embodiment, slide 4A1 has 96 positions 60 arranged in an 8×12 array. At each position 60, slide 4A1 is etched so as to be better able to retain a drop of solution deposited at the spot.

Figure 17A:
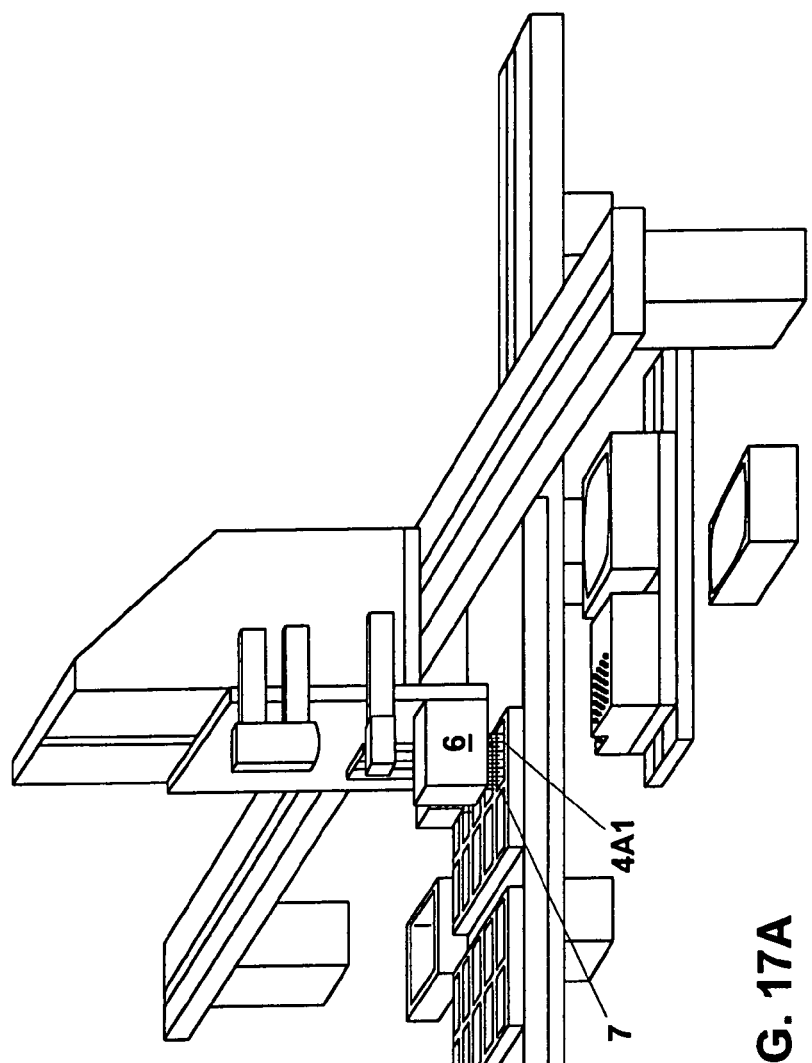
Figure 17B:
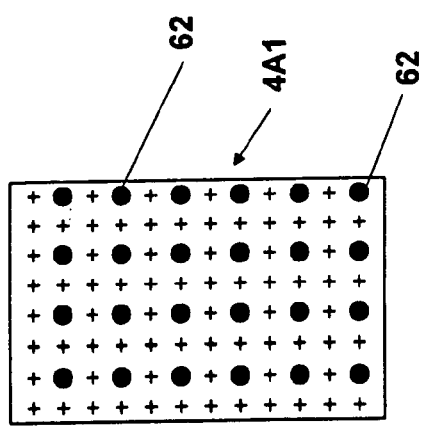

Dispense head 6 is then lowered via linear actuator 26 so that tips 7 are in contact with slide 4A1 at the first dispense position, as shown in FIG. 17A. As tips 7 contact slide 4A1, spots 62 are placed on slide 4A1 via surface tension, as shown in FIG. 17B.

Figure 18:
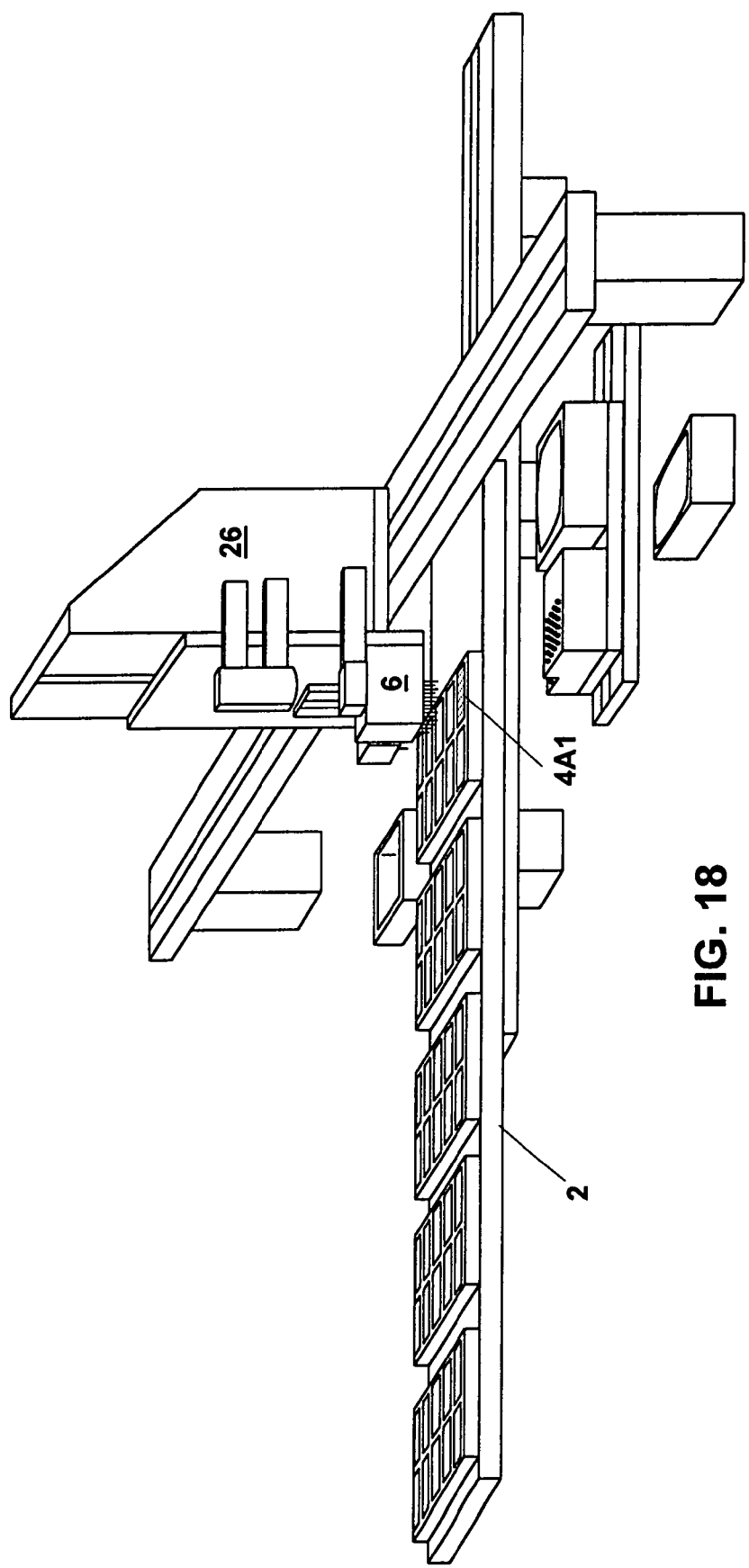

Dispense head 6 is raised via linear actuator 26, as shown in FIG. 18. Based on the earlier positioning data regarding slide 4A1, linear actuator 21 makes minute positioning adjustments to linear actuator 26 and linear actuator 15 makes minute positioning adjustments to platform 2 in order to accurately position dispense head 6 over slide 4A1 at the second dispense position.

Dispense head 6 is then lowered via linear actuator 26 so that tips 7 are in contact with slide 4A1 at the second dispense position, as shown in FIG. 19A. As tips 7 contact slide 4A1, more spots 62 are added to slide 4A1, as shown in FIG. 19B.

Dispense head 6 is raised via linear actuator 26, as shown in FIG. 20. Based on the earlier positioning data regarding slide 4A1, linear actuator 21 makes minute positioning adjustments to linear actuator 26 and linear actuator 15 makes minute positioning adjustments to platform 2 in order to accurately position dispense head 6 over slide 4A1 at the third dispense position.

Dispense head 6 is then lowered via linear actuator 26 so that tips 7 are in contact with slide 4A1 at the third dispense position, as shown in FIG. 21A. As tips 7 contact slide 4A1, more liquid spots 62 are added to slide 4A1, as shown in FIG. 21B.

Figure 22:
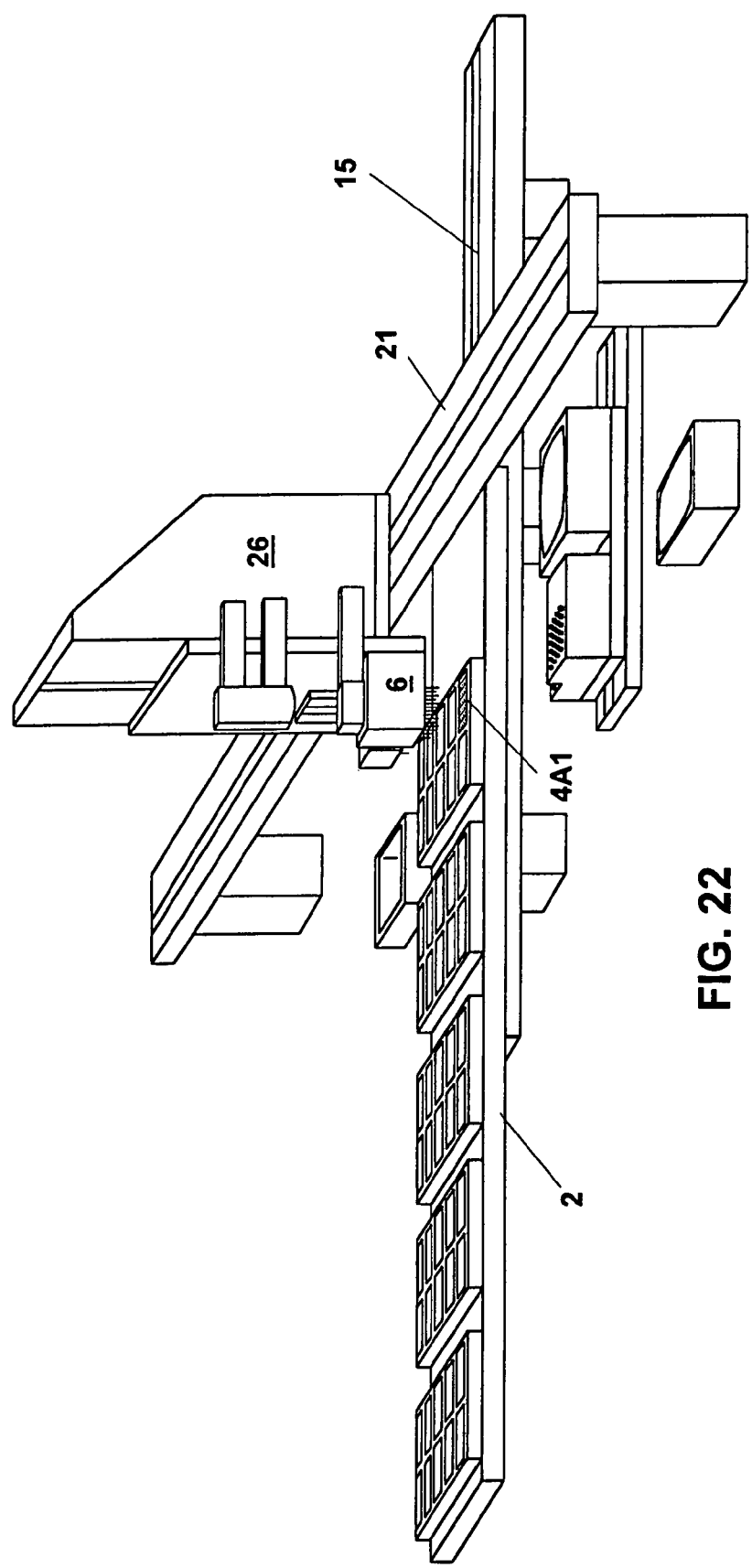

Dispense head 6 is raised via linear actuator 26, as shown in FIG. 22. Based on the earlier positioning data regarding slide 4A1, linear actuator 21 makes minute positioning adjustments to linear actuator 26 and linear actuator 15 makes minute positioning adjustments to platform 2 in order to accurately position dispense head 6 over slide 4A1 at the fourth dispense position.

Figure 23A:
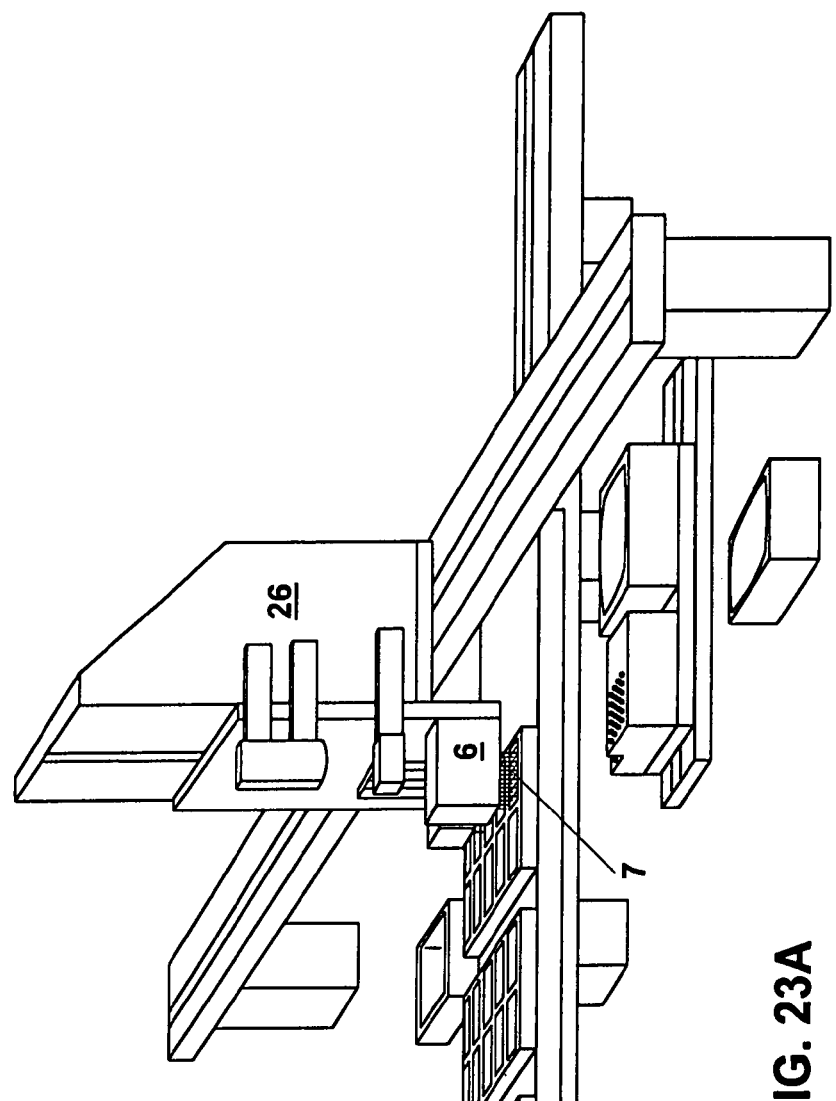
Figure 23B:
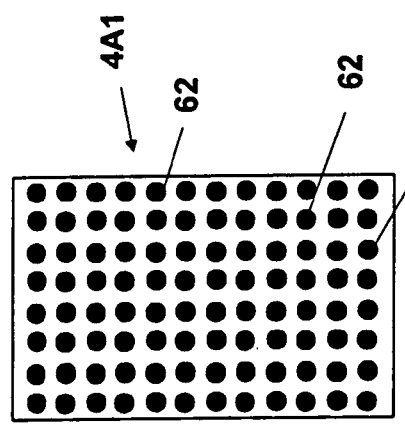

Dispense head 6 is then lowered via linear actuator 26 so that tips 7 are in contact with slide 4A1 at the fourth dispense position, as shown in FIG. 23A. As tips 7 contact slide 4A1, more liquid spots 62 are added to slide 4A1, as shown in FIG. 23B.

Figure 24:
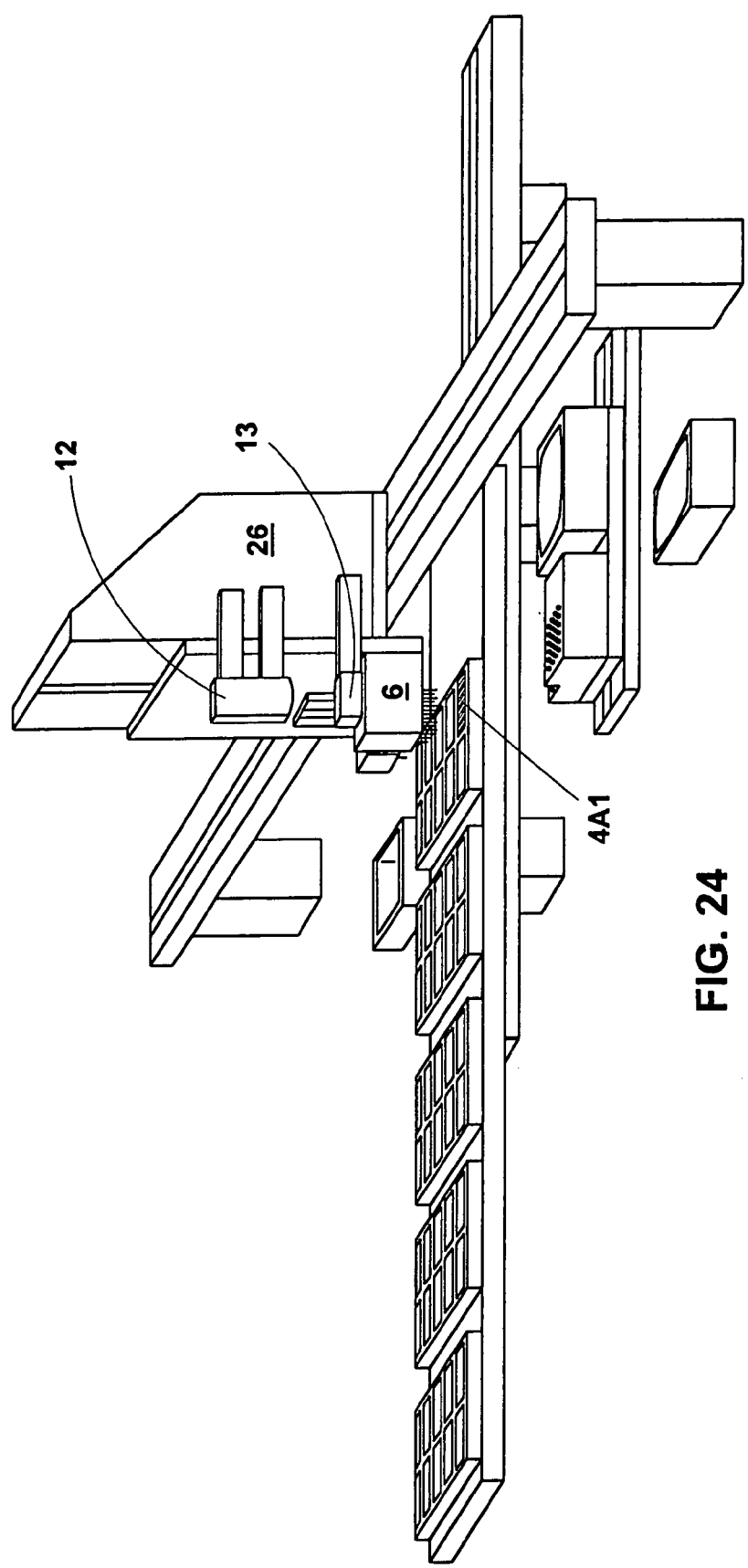

Dispense head 6 is raised via linear actuator 26, as shown in FIG. 24. Camera 12 and strobe 13 scans slide 4A1 and acquires images and inspects for spot quality. It is at this point that PC control system 300 (FIG. 37) identifies slide 4A1 as pass or fail. (Preferred computer controlled techniques for making this determination are discussed in a following section.)

Figure 25:
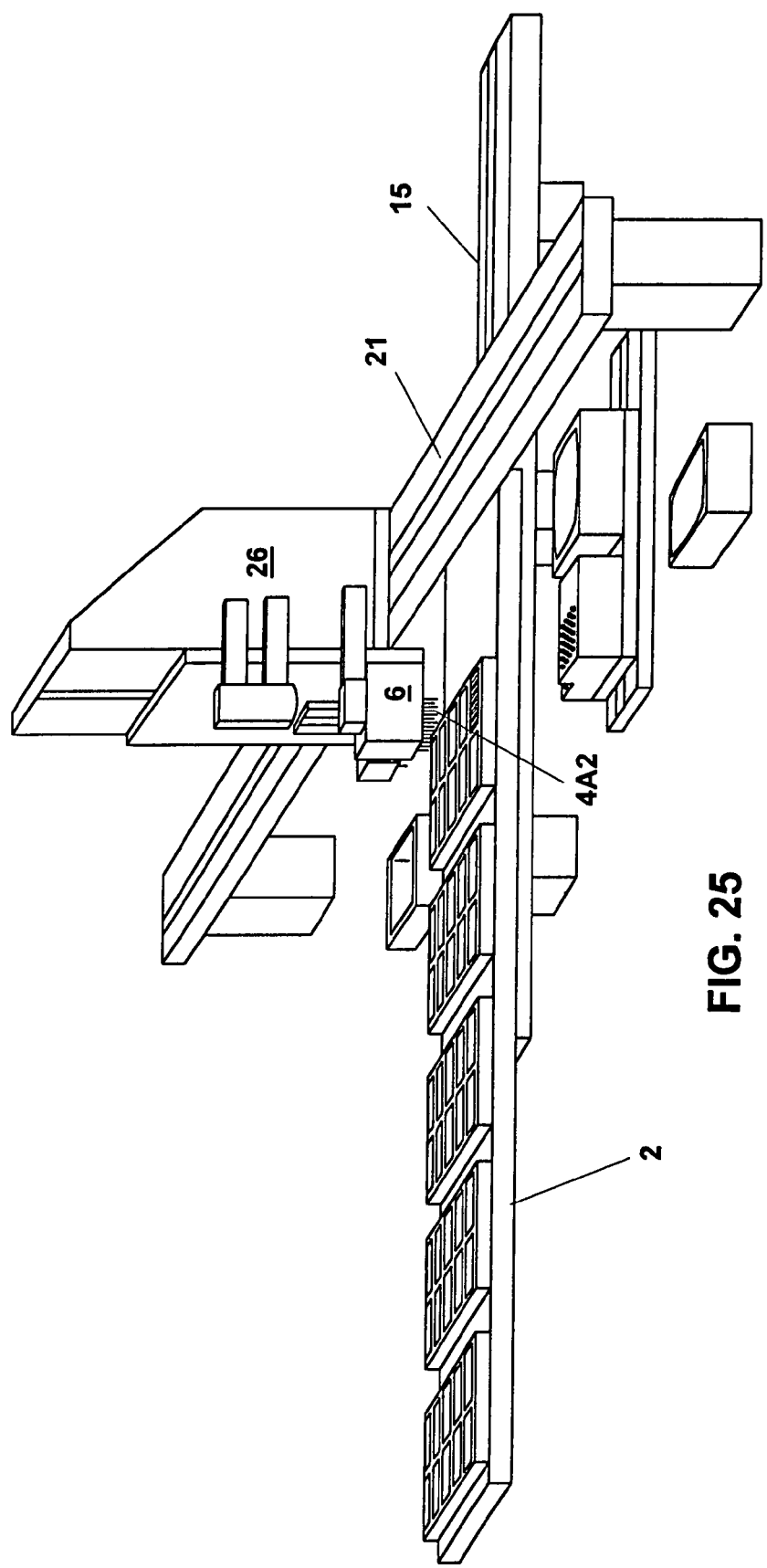

As shown in FIG. 25, based on the earlier positioning data regarding slide 4A2 (see discussion regarding FIG. 5), linear actuator 21 makes positioning adjustments to linear actuator 26 and linear actuator 15 makes positioning adjustments to platform 2 in order to accurately position dispense head 6 over slide 4A2 at the first dispense position for slide 4A2.

The four-stage liquid dispense cycle (explained above with respect to slide 4A1 in discussion regarding FIGS. 17A–24) is repeated so that at the end of the four-stage cycle, slide 4A2 contains spots 62, as shown in FIG. 26B. At the end of the four stage cycle, dispense head 6 is raised via linear actuator 26, as shown in FIG. 26A. Camera 12 and strobe 13 scans slide 4A2 and acquires images and inspects for spot quality. It is at this point that the control system identifies slide 4A2 as pass or fail.

Figure 27:
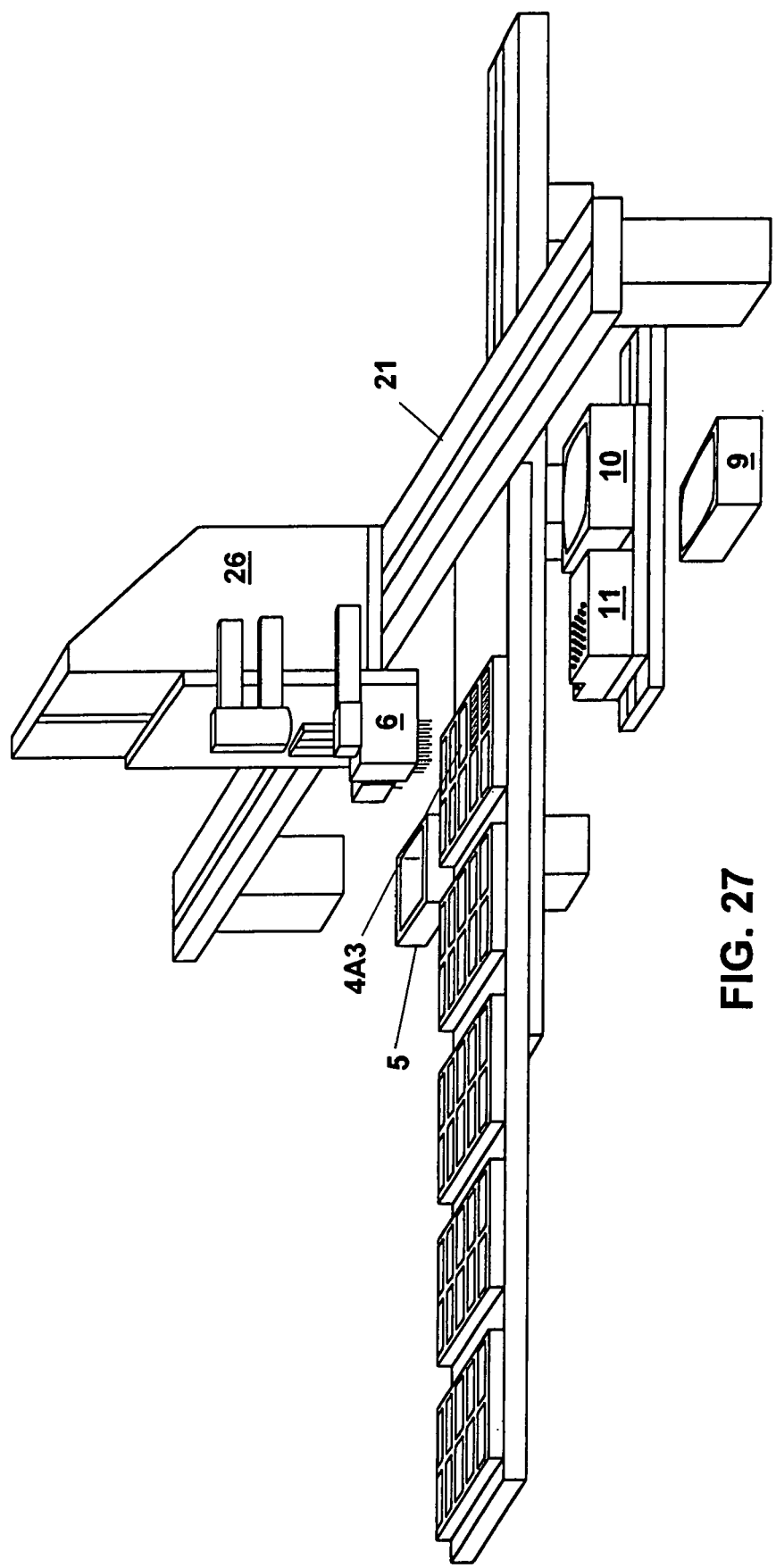

As shown in FIG. 27, linear actuator 21 moves linear actuator 26 so that dispense head 6 is above slide 4A3.

Figures 28A, 28B, 28C:
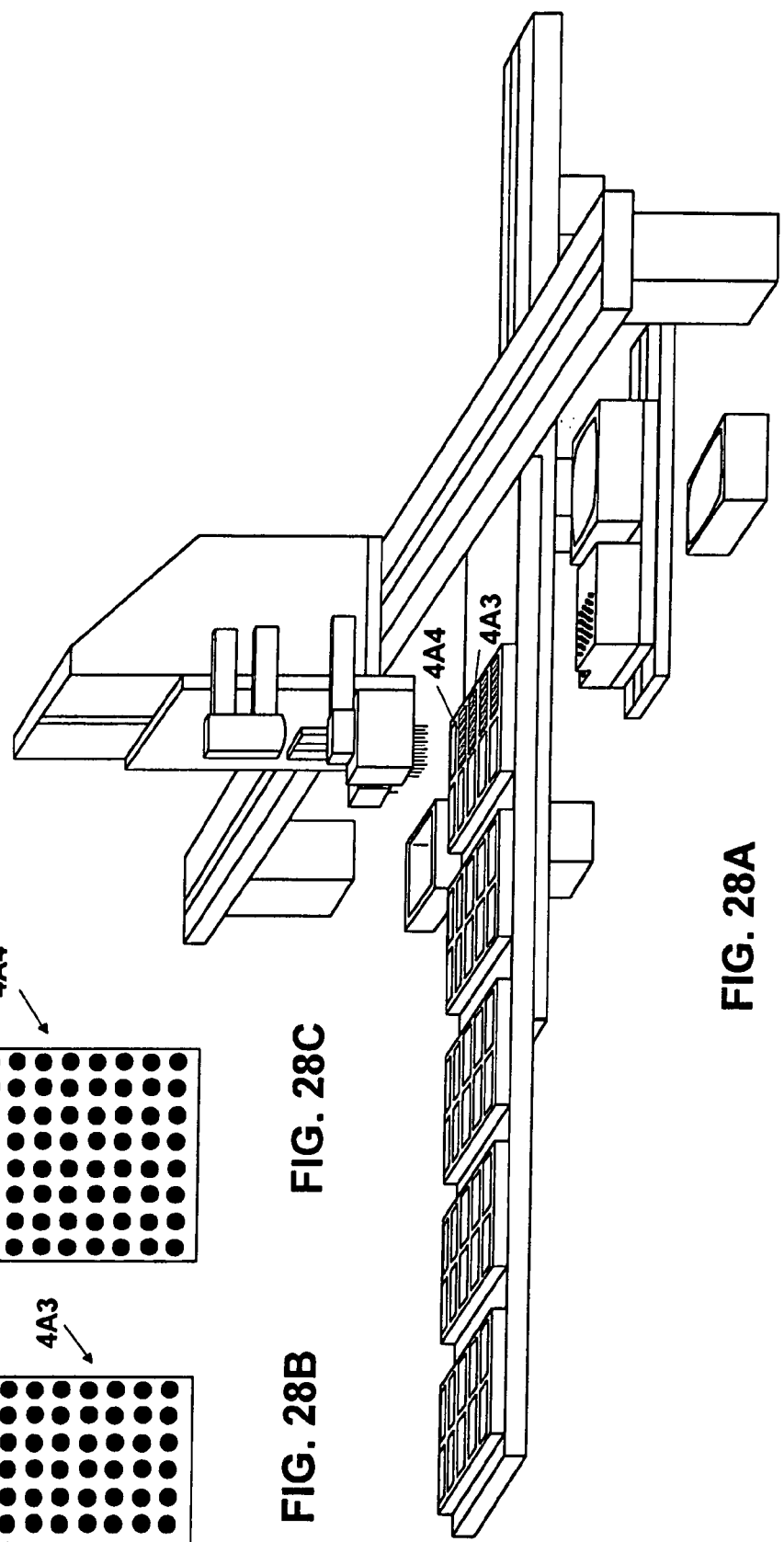

The sequence outlined in the discussion regarding slides 4A1 and 4A2 (depicted in FIGS. 4–26) is repeated with regards to slides 4A3 and 4A4. To summarize, by utilizing light provided by strobe 13, camera 12 will first record the positions of slides 4A3 and 4A4. Then, dispense tips 7 are dipped in sonic cleaner 9. Dispense tips 7 are then rinsed in rinse fountain 10. Then, dispense tips 7 are dried in vacuum manifold 11. This cycle is repeated as needed. Then, liquid is picked up by dispense tips 7 when dispense tips 7 are lowered into reservoir plate 5. Then, liquid is spotted onto slide 4A3 by dispense tips 7 in a four-stage liquid dispense cycle. Likewise, liquid is spotted onto slide 4A4 in a four-stage liquid dispense cycle so that liquid has been spotted on both slides, as shown in FIGS. 28B and 28C.

Figure 29:
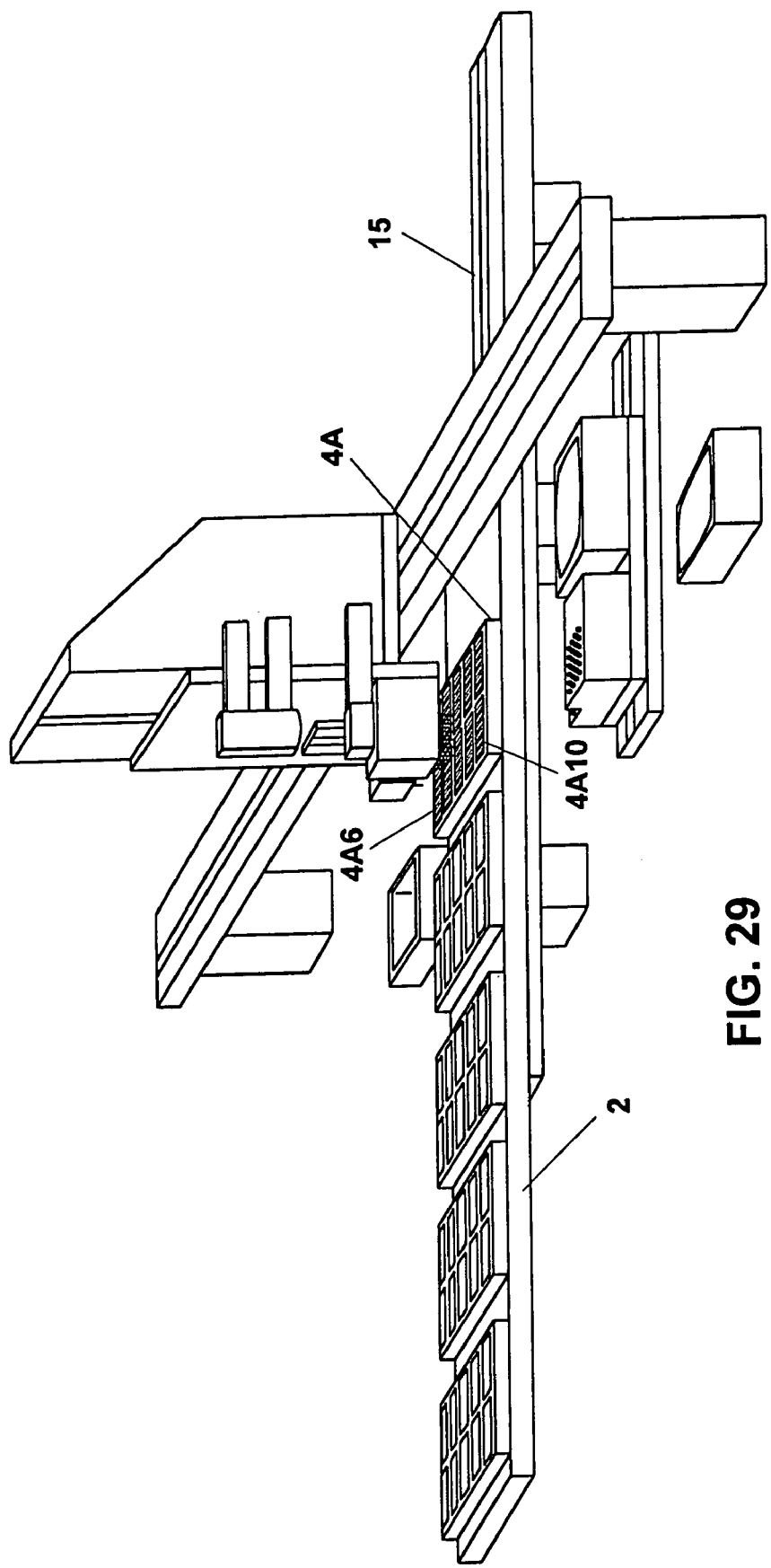

The process is then repeated for the remaining six slides 4A5–4A10 until all the slides on locator plate 4A have been spotted, as shown in FIG. 29.

Figure 30:
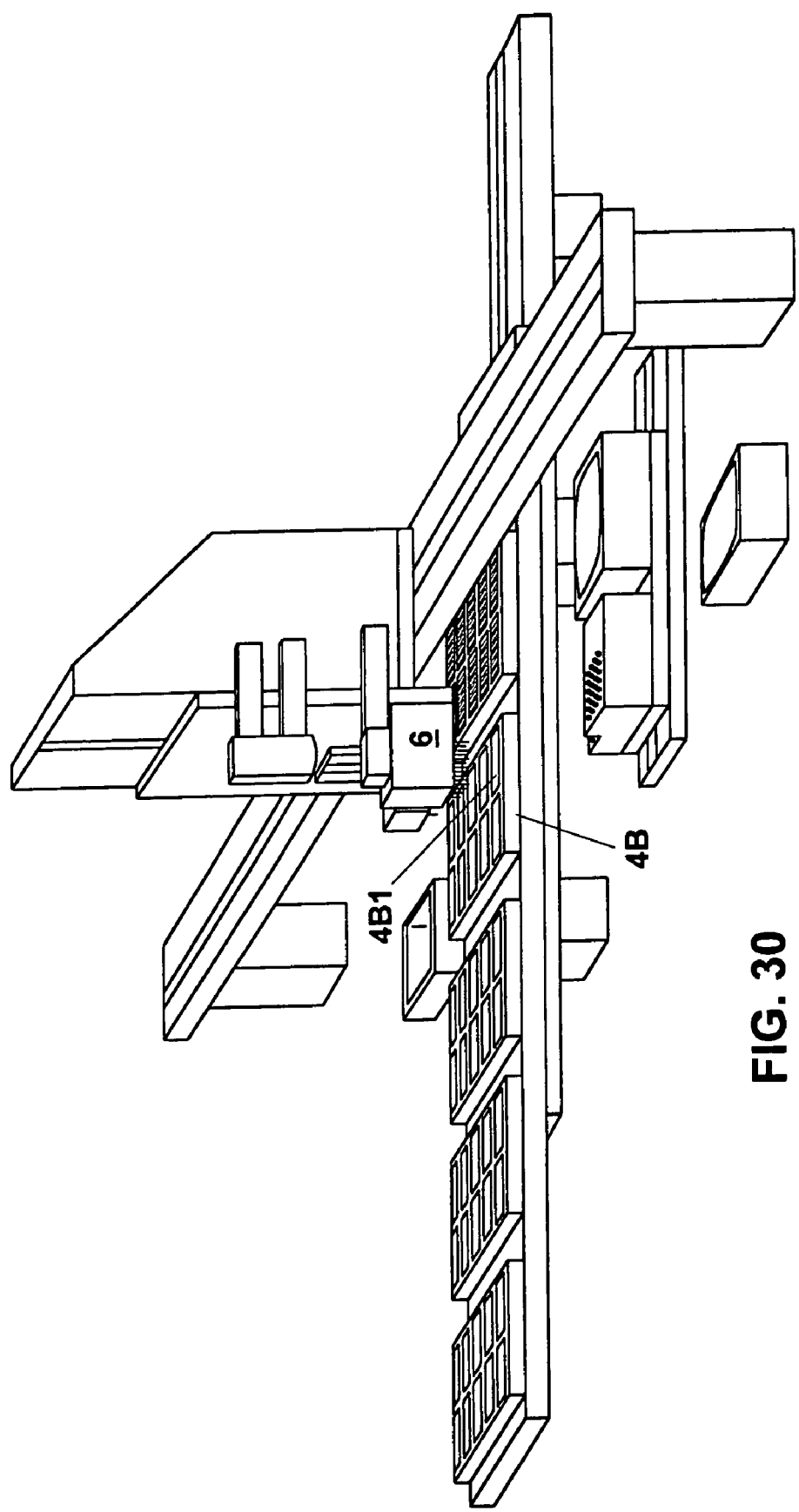

Linear actuator 15 then moves platform 2 so that slide 4B1 of locator plate 4B is underneath dispense head 6, as shown in FIG. 30.

Figure 31:
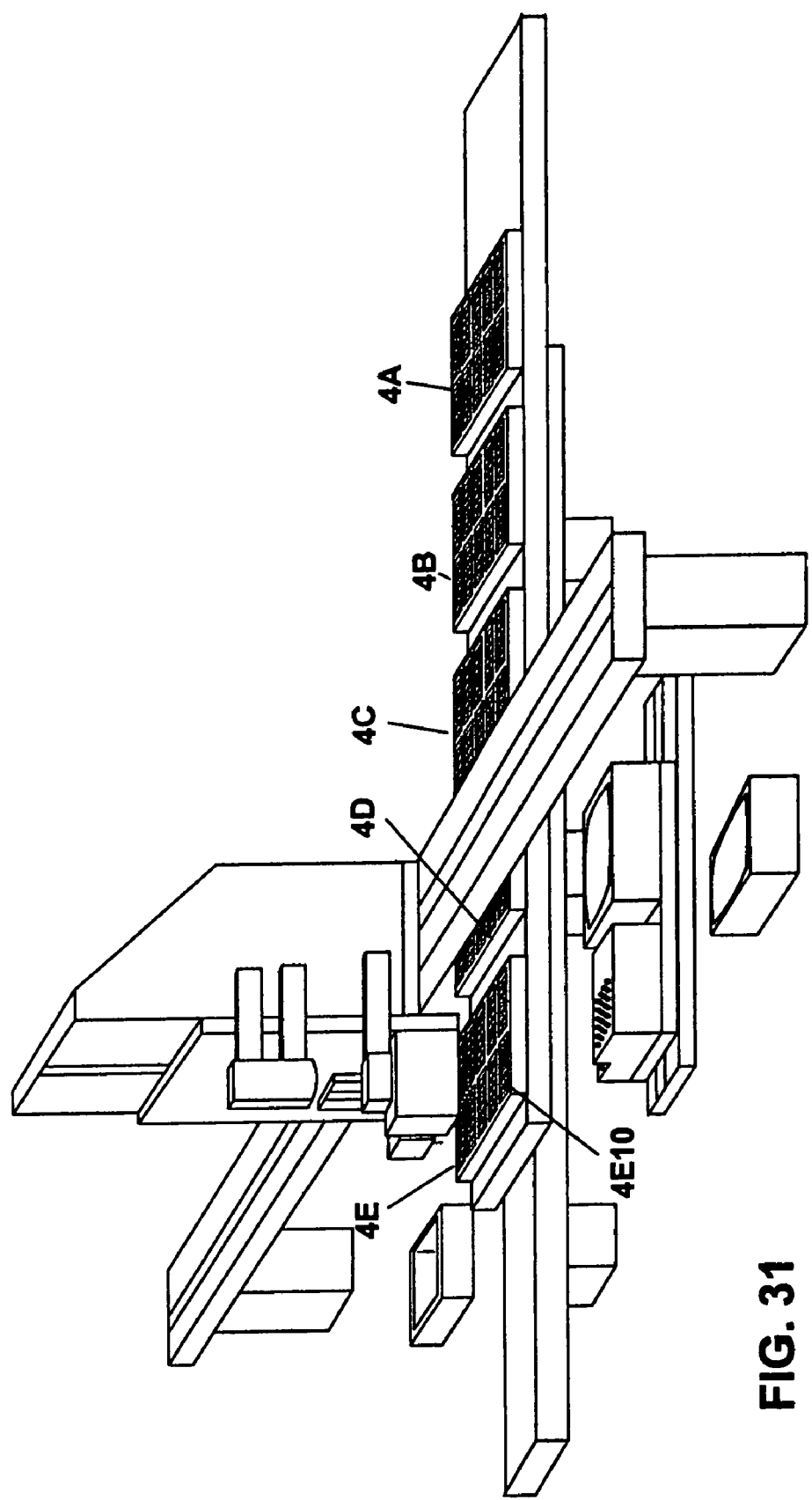

In a similar fashion, dispense tips 7 continue to spot all ten slides on locator plates 4B–4E, until the last slide 4E10 has been spotted, as shown in FIG. 31.

Figure 32:
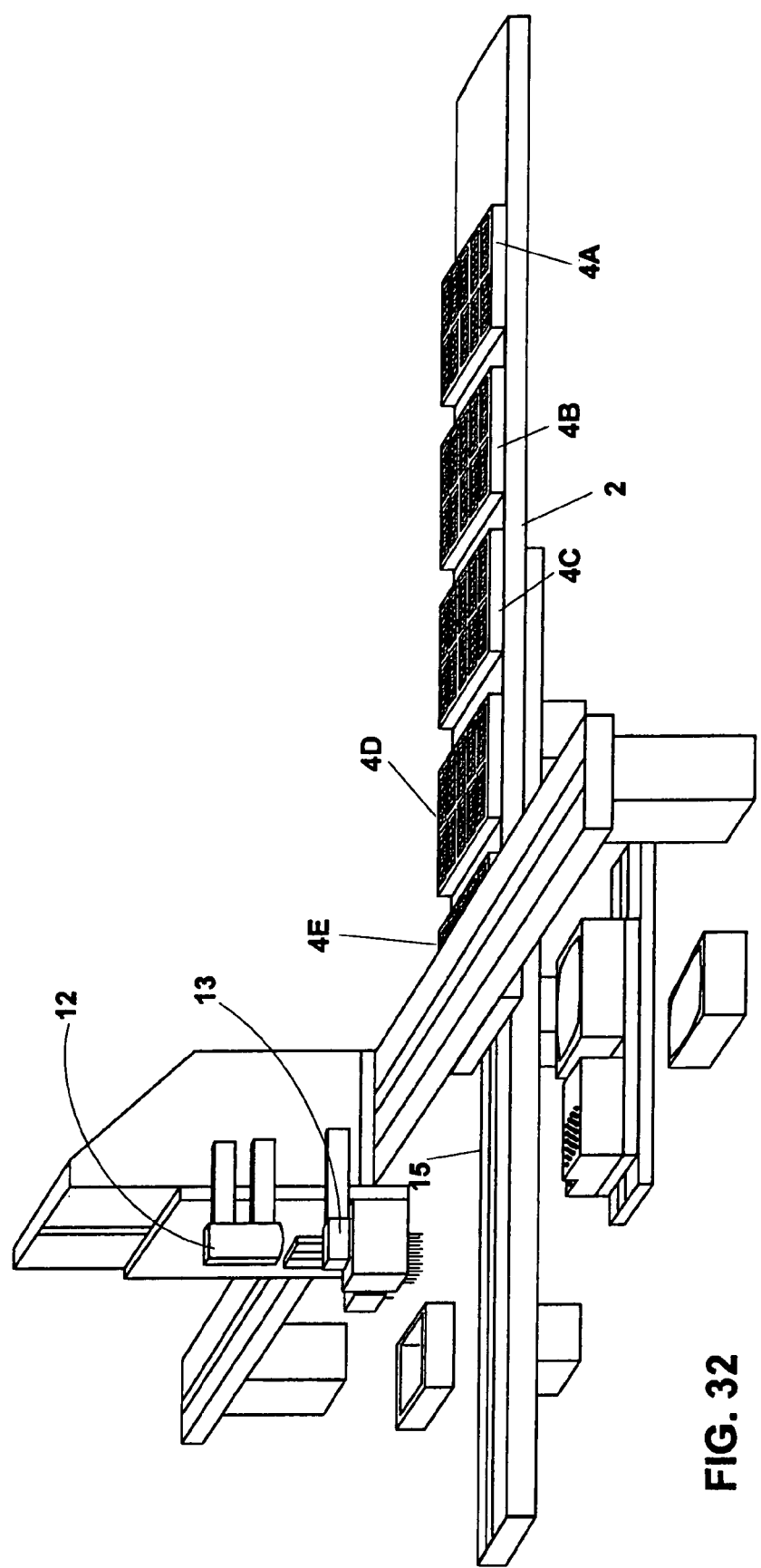

After slide 4E10 has been spotted and camera 12 and strobe 13 has scanned slide 4E10 for spot quality, linear actuator 15 moves platform 2 to the position shown in FIG. 32 so an operator can remove locator plates 4A–4E.

Computer Controlled Pass-Fail Determination Technique

The computer controlled pass-fail determination technique determines individual spots as pass or fail based on several criteria. For each slide, the camera system scans a region to look for a spot. In a preferred embodiment the criteria that are applied to that inspection region are spot presence, spot size in area, spot location, and spot geometry. Additional criteria can be added through software configuration. Each of the criteria can have upper and lower limits designated which define the acceptable values for that particular criteria. Any value that falls outside of the limits for any criteria qualifies that spot and slide as failed. The actual inspection values are determined by analyzing the grayscale intensity of each pixel. The total number of pixels falling above and below a threshold are tallied to give values for each of the inspection criteria.

Rework Capability

As explained above, after each slide has been spotted, camera 12 and strobe 13 scans the slide and acquires images and inspects for spot quality. It is at this point that the control system identifies the slide as pass or fail. In a preferred embodiment of the present invention, an operator monitoring the spotting process via monitor 305 (FIG. 37) has the option of correcting a slide that has failed.

For example, FIG. 29 shows locating plate 4A after all slides 4A1–4A10 have been spotted. At this point, an operator can scan locating plate 4A. A good plate shows up green as in all slides pass. A plate with at least one bad spot on one of the slides shows up red. The user can then zoom in on the bad slide and the good and bad spots show up green and red respectively as pass or fail. From there, the user can decide whether or not to rework the bad spots.

FIGS. 39A and 39B show where an operator has decided to rework slide 4A6 that has a spot that has failed quality inspection. Dispense head 40 is lowered via pneumatic slide 41 so that dispense tip 42 is lower than dispense tips 7. Solution from reservoir plate 5 is then deposited on the slide at the location of the failed spot. If there are other spots that failed, the operator can likewise rework those spots in a similar fashion.

Although in the description given above regarding the rework process, the operator reworked failed slides after locating plate 4A had been entirely spotted, it is also possible to rework failed slides at other stages during the spotting process. For example, it may be desirable to wait until all slides 4A1–4E10 on plates 4A–4E have been spotted (FIG. 31) before reworking them. This allows an operator to be free to do other activities while the initial spotting is taking place. Then, after all slides have been spotted, he can come back and do all the reworking at one sitting.

Alternatively, it may be desirable to rework each slide immediately after it has been spotted, as shown in FIG. 24.

Automatic Rework Capability

The previous section described a preferred embodiment where an operator can decide whether or not to rework a spot based on a computer determination of pass or fail. In another preferred embodiment the rework decision is made automatically by the computer based on whether or not the spot has passed or failed. In this preferred embodiment, the computer makes a determination whether or not a spot has passed or failed using the computer controlled pass-fail determination technique earlier described. If, based on its analysis, the computer determines that the spot has failed, the computer will automatically take steps to rework the spot. For example, dispense tip 42 will extract solution from reservoir plate 5. Then, the computer will lower dispense head 40 via pneumatic slide 41 so that dispense tip 42 is lower than dispense tips 7, as shown in FIGS. 39A and 39B. Solution from reservoir plate 5 will then deposited on the slide at the location of the failed spot.

Components of a Preferred Embodiment of the Present Invention

Three Axis Robotic Positioning Stage

Figure 33:
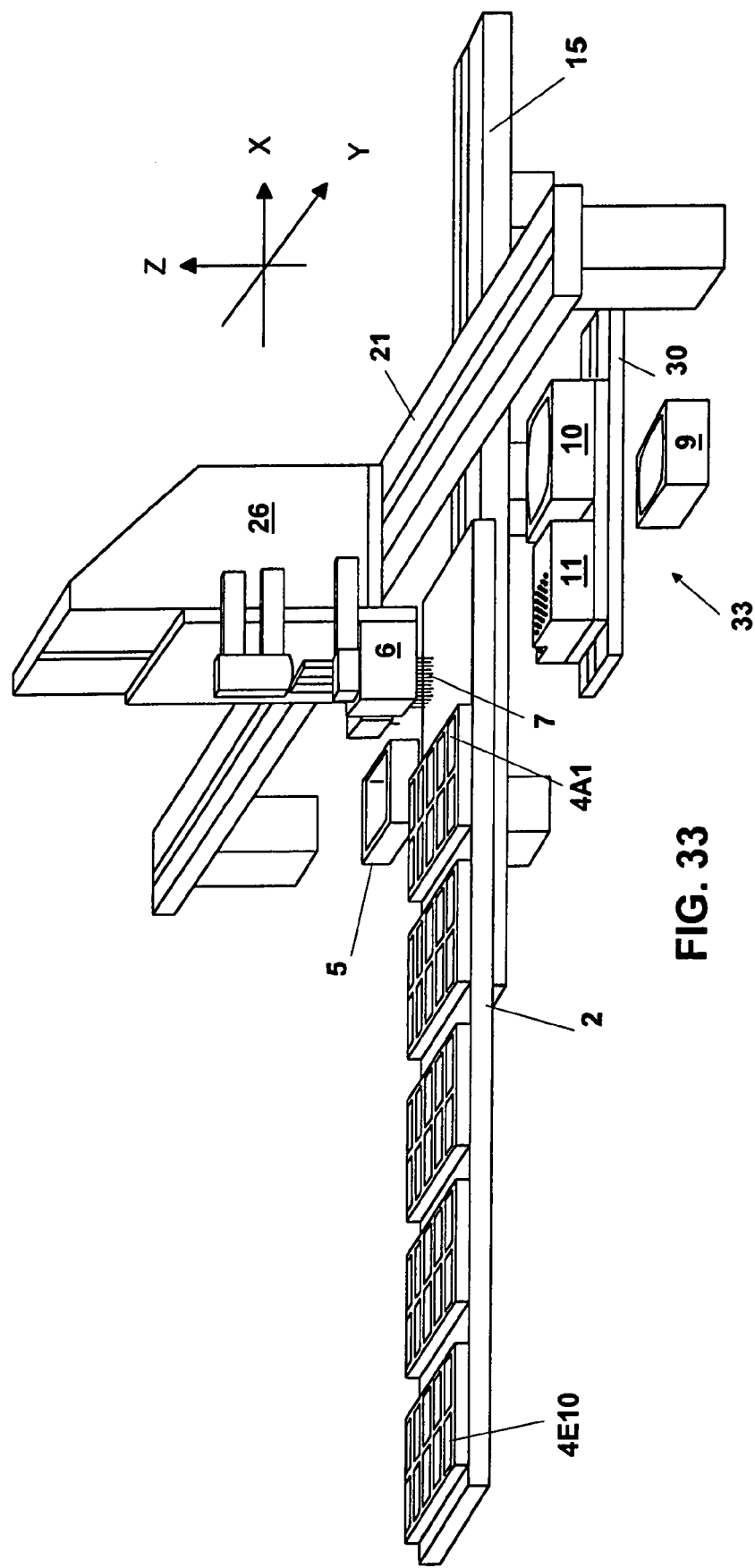
FIG. 33 shows the major components of a preferred embodiment of the present invention.

In a preferred embodiment, linear actuators 26, 21 and 15 are industrial grade precision ground ball screw linear actuators, as shown in FIG. 33. These linear actuators are manufactured by Parker Automation (Model #s:404XR and 406XR series). They are each controlled by a smart servomotor (SmartMotor, Model #2320 VRE, manufactured by Animatics, with offices in Santa Clara Calif.), which is a fully self-contained closed loop servo system. Each of these smart servomotors contains the motor, encoder, amplifier, and controller all in one small package mounted to the linear actuator. Linear actuator 15 (the x-axis positioning device) has an overall travel distance of 600 mm with an accuracy within +/−0.032 micrometers Linear actuator 21 (the y-axis positioning device) has an overall travel distance of 400 mm with an accuracy within +/−0.032 micrometers. Linear actuator 26 (the z-axis positioning device) has an overall travel distance of 100 mm with an accuracy within +/−micrometers. In this preferred embodiment, this extreme accuracy is needed to accommodate very small spot size and spacing between spots. The linear actuators have pitches of 5 mm per revoloution giving a positioning accuracy of $0.032 \times 10^{-6}$ meters.

Linear actuator 15 controls the positioning of platform 2 containing slides 4A1–4E10 along the x-axis of motion making all slides presentable to the dispense head 6. Linear actuator 21 controls the positioning of the dispense head along the y-axis of motion making all slides 4A1–4E10, sonic cleaner 9, rinse fountain 10, vacuum manifold 11, and reservoir plate 5 presentable to dispense head 6. Linear actuator 26 controls the positioning of dispense head 6 along the z-axis of motion allowing dispense head 6 to be lowered to and raised from all slides 4A1–4E10, sonic cleaner 9, rinse fountain 10, vacuum manifold 11, and reservoir plate 5.

Cleaning Station

Cleaning station 33 consists of sonic cleaner 9, rinsing fountain 10, and a drying vacuum manifold 11. In a preferred embodiment, sonic cleaner 9 is an ultrasonic cleaner manufactured by Prosonic, Inc. (part no. E0028). Sonic cleaner 9 can contain either a cleaning solution or simply purified water. Dispense tips 7 are dipped in the sonic cleaner 9, where the ultra sonic oscillations of the cleaning solution clean the tips.

Rinsing fountain 10 and the vacuum manifold 11 are placed on a pneumatic slide 30. Pneumatic slide 30 is used to select which operation is to be performed, rinsing or drying. The reason for this slide is so that both operations can be performed at a single position along the y-axis. This allows for both operations without having to increase the overall travel of linear actuator 26 along the y-axis.

Rinsing fountain 10 pumps in purified water and drains it out to a waste bin. Dispense tips 7 are dipped in this purified water to rinse away any debris or cleaning solution that may remain on the tips after cleaning.

Drying vacuum manifold 11 is a block with an array of holes in it that match the array of dispense tips 7. The tips are inserted into the block, each of these holes are connected to a manifold which is connected to a vacuum generator and air supply. The vacuum pulls away any remaining liquid or debris left on the dispense tips after rinsing.

Dispense Head Assemblies

Figure 35B:
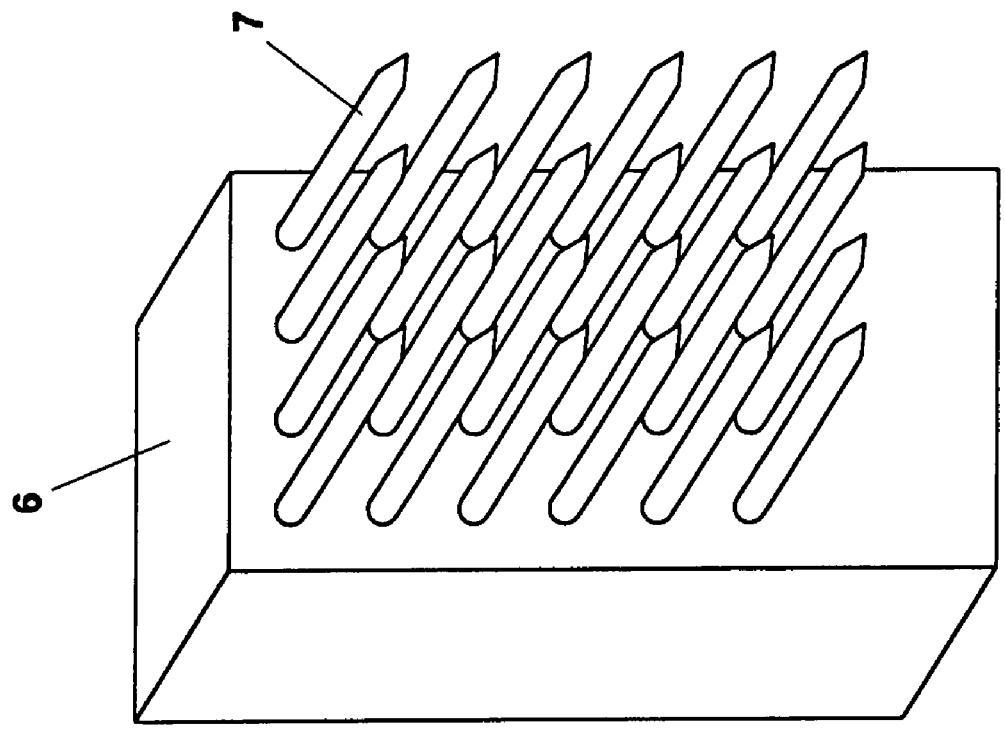
FIGS. 35A and 35B shows dispense tips attached to dispense heads.
Figure 35A:
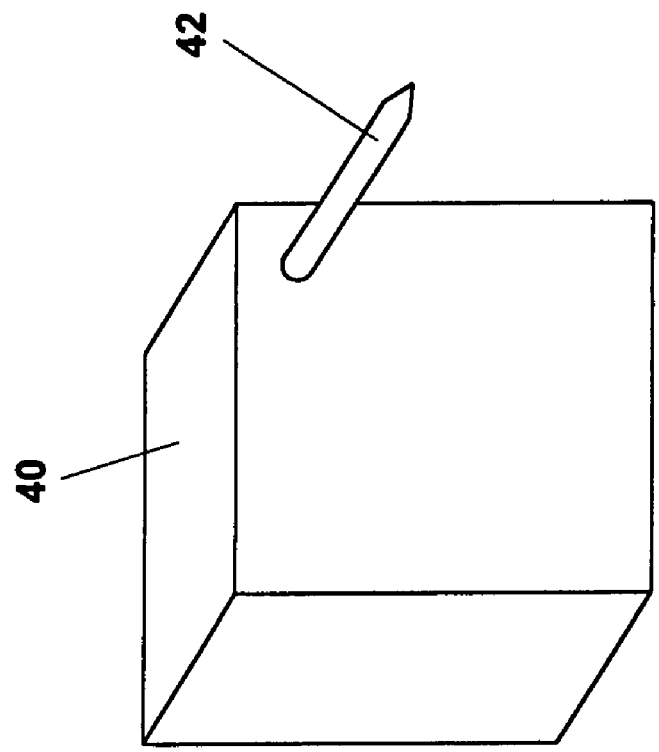

As shown in FIG. 35B, dispense head 6 is a 4×6 grid Micro Quill Holder (part no. 11946-0) made by Major Precision of Arizona. A 4×6 array of primary dispense tips 7 are held in dispense head 6. As shown in FIG. 35A, dispense head 40 is a Micro Quill Holder also made by Major Precision. Dispense tip 42 is held in dispense head 40. Dispense tips 7 and 42 are spring loaded within the dispense heads 6 and 40.

Figure 2:
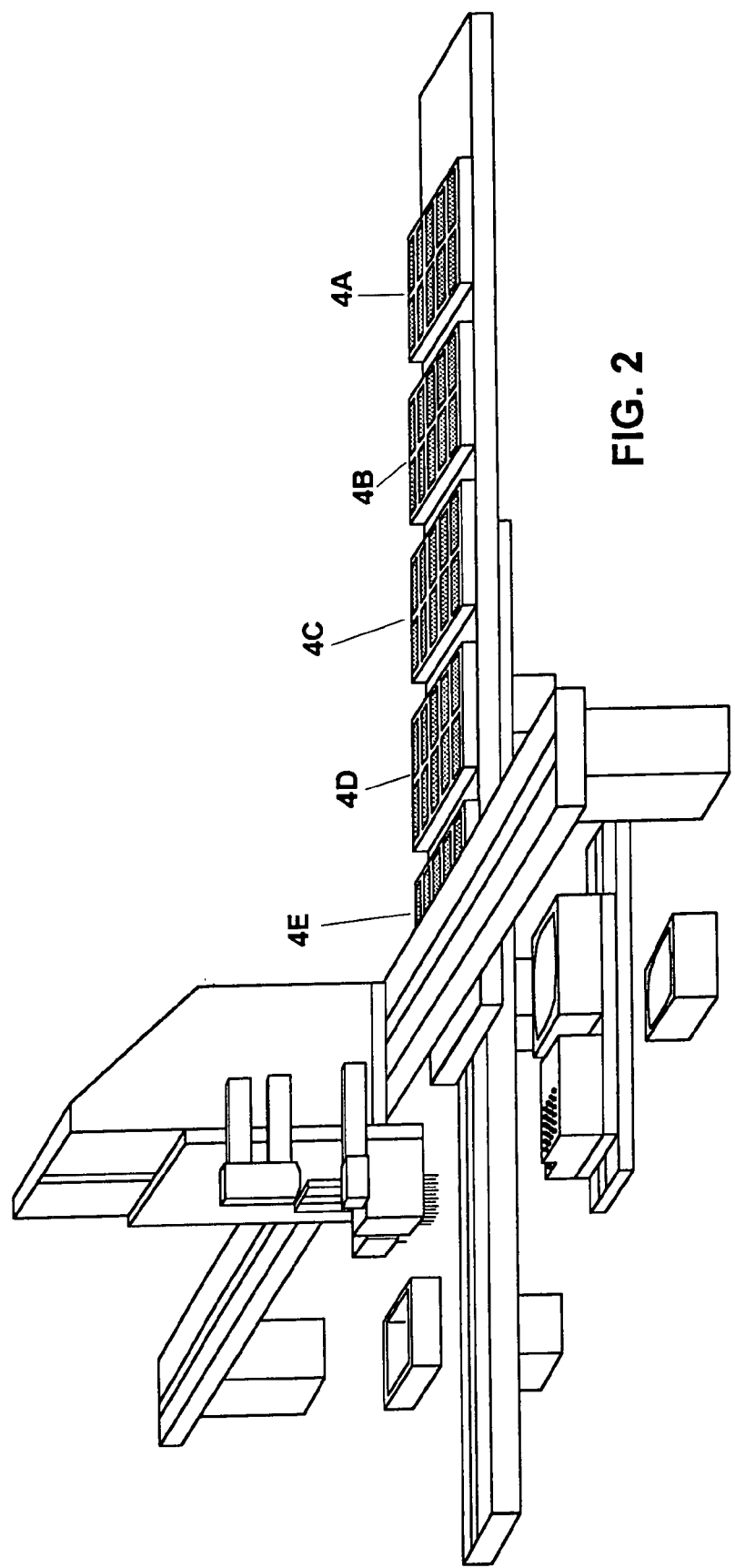
FIG. 2 shows slides fifty slides located on 5 locating plates after the slides have been spotted.

As shown in FIGS. 1, 34A and 34B, dispense head 6 is rigidly mounted to mounting plate 25, whereas dispense head 40 is mounted to pneumatic slide 41 (manufactured by Robohand, Inc., with offices in Montroe, Conn., part no. MPS1-2). Mounting plate 25 is capable of moving up and down along the z-axis via linear actuator 26. Furthermore, dispense head 40 is capable of independent additional movement up and down along the z-axis via pneumatic slide 41, as shown in FIGS. 34A–34B.

During normal operation, such as that depicted in the sequence illustrated in FIGS. 3–32, dispense head 6 is used to spot slides 4A1–4E10. For example, FIG. 34C shows a front view of dispense tips 7 in contact with slide 4A1. Dispense tips 7 will be used to spot slide 4A1 at positions 60, as shown in FIG. 34C. Note that when dispense head 6 has been selected, dispense head 40 is raised via pneumatic slide 41 so that dispense tips 42 do not interfere with the spotting process.

If, however, the operator wishes to spot slide 4A1 at positions 61 (FIG. 34C), dispense head 40 will be lowered via pneumatic slide 41 so that dispense tips 42 are in contact with slide 4A1 and dispense tips 7 are out of the way, as shown in FIG. 34B.

Camera and Lighting

In a preferred embodiment, camera 12 and strobe 13 are mounted to the side of linear actuator 26 as shown in FIG. 1. Camera 12 is a self-contained camera with image processing and Ethernet capabilities manufactured by DVT Corporation with offices in Norcross, Ga. (series 600 model). Using light provided by strobe 13, camera 12 can snap pictures while in dynamic motion, process the image for results, pass the results off to the PC control system, and prepare for the next image acquisition. The camera uses a 55 mm Telecentric lens which provides the proper field of view and magnification for reading of 2D bar code 62 (FIG. 34C) and for image inspection. Strobe light 13 is preferably Model DL2449, manufactured by Advanced Illumination, with offices in Rochester, Vt. In the preferred embodiment, the image acquisition time is ~40 ms and the image processing time is ~50 ms. The system can also be equipped with a flouresence device along with the camera for further genomic expression analysis.

Vibration Isolated Base

Figure 36:
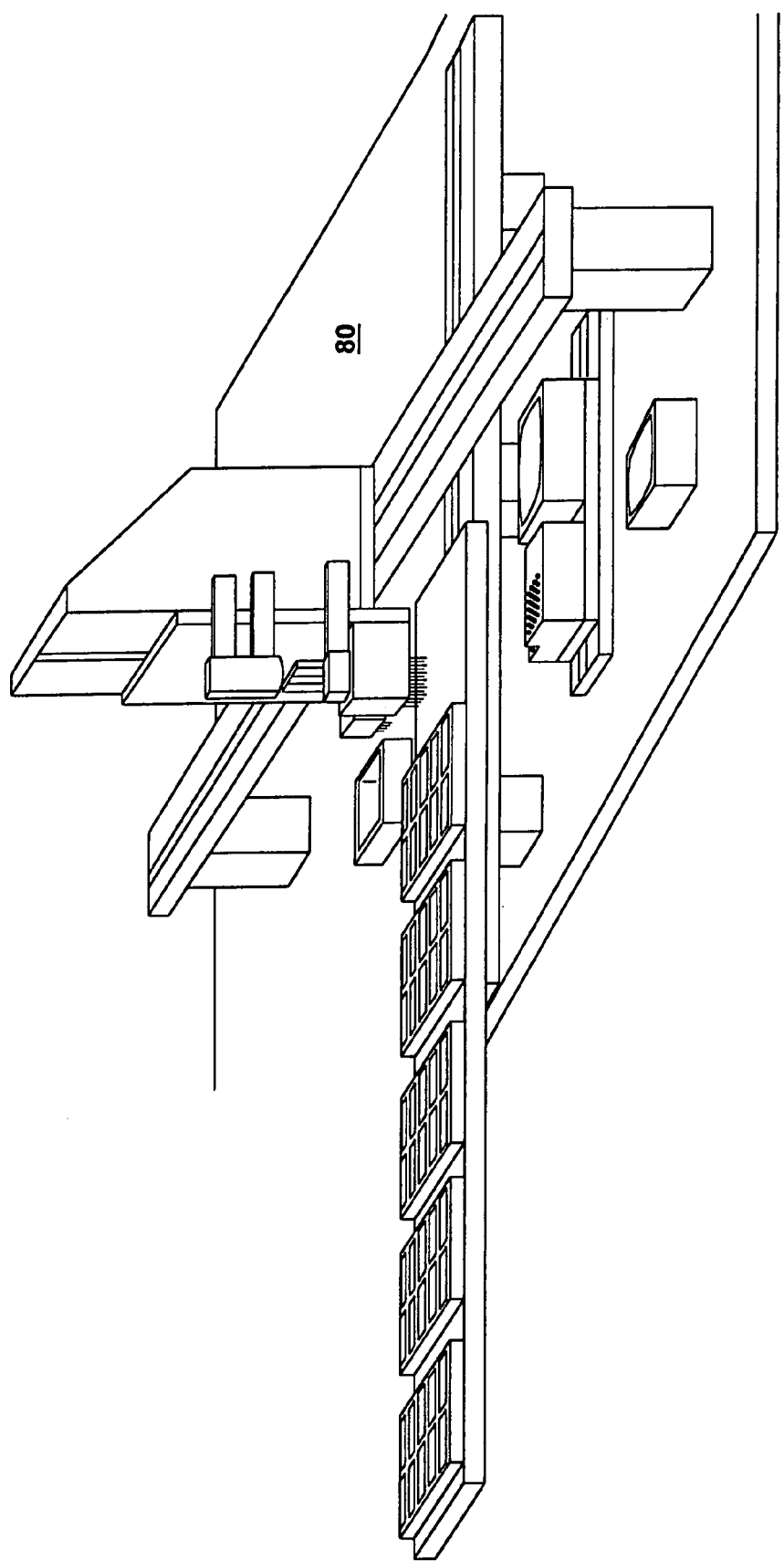
FIG. 36 shows a preferred embodiment of the present invention mounted on a vibration isolated base.

As shown in FIG. 36, vibration isolated base 80 is provided to minimize any possible affects that high frequency environmental vibrations might have on the dispensing process. This base is a pneumatic system which acts as a shock absorber to the system. In a preferred embodiment, the base is manufactured by Newport, Inc. with offices in Irvine, Calif., model # CM-225.

PC Based Control System

FIG. 37 depicts a block diagram of PC control system 300 and other components of a preferred embodiment of the present invention. PC Control System 300 includes CPU 301 with associated memory (RAM 302 and ROM 303). It also includes a touch screen monitor/interface 305 that allows for operator monitoring, intervention and control of the present invention. In the preferred embodiment, the computer system is a PC based computer equipped with an ethernet card and running windows software. The programming is preferably written in VISUAL BASIC. (VISUAL BASIC is a federally registered trademark of Microsoft Corp., a Delaware Corporation) PC Control System 300 is equipped with CMS (Central Monitoring System). The CMS gives PC Control System 300 it's own IP (Internet Protocol) address and ethernet connectivity. This allows for remote monitoring and control via Intranets as well as Internet provided that the bandwith is available for proper functionality. The software is highly comfigurable to allow increased flexibility for customers with varying slide types, slide sizes, slide orientations, spot size, spot spacing and many other variables.

Control of the Components of the Preferred Embodiment of the Present Invention through the PC Control System As previously stated, linear actuators 26, 21 and 15 are industrial grade precision ground ball screw linear actuators. As shown in FIG. 37, PC control system 300 sends signals to smart servomotors 26A, 21A and 15A to control linear actuators 26, 21 and 15, respectively. PC control system 300 controls sonic cleaner 9 and rinse fountain 10. Compressed air source 310 provides compressed air to pneumatic slides 30 and 41 via valves 310 controlled by PC control system 300. Vacuum generator 320 provides a vacuum to vacuum manifold 11 via valve 317. As previously explained camera 12 and strobe 13 work in conjunction to provide sensory data to PC control system 300. This input is used to accurately position the dispense heads over the slides to ensure optimum spotting and to verify the quality of the spotting as "pass" or "fail" using multiple criteria as to placement at intended location as well as spot size (too big or too small).

Second Preferred Embodiment of the Present Invention

Figure 41:
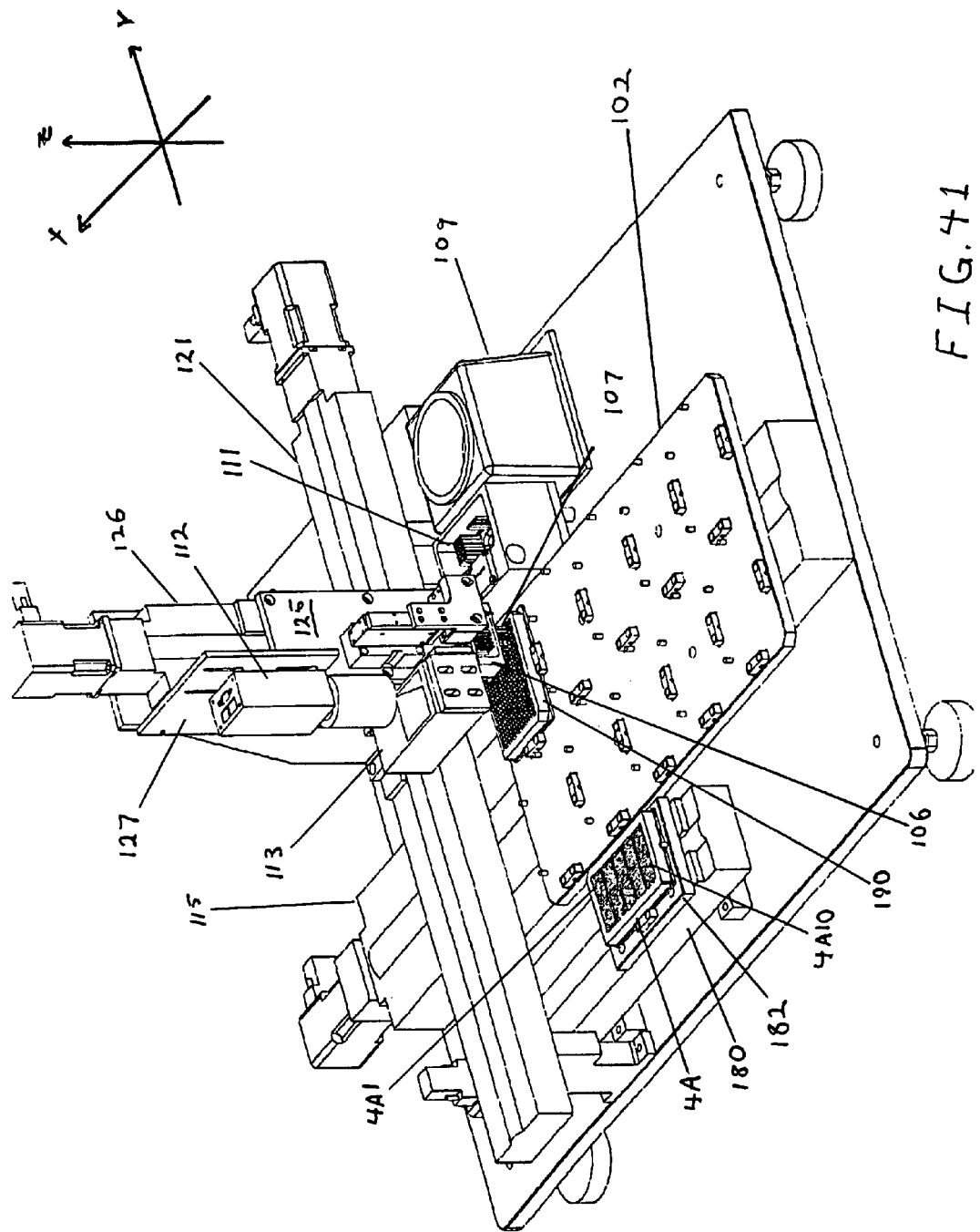
FIG. 41 shows another preferred embodiment of the present invention.

A second preferred embodiment of the present invention is shown in FIG. 41. In the second preferred embodiment, dispense head 106 is connected via mounting plate 125 to linear actuator 126 so that dispense tips 107 can be raised and lowered along the z-axis into solution in microplate 190. Camera 112 and strobe 113 are rigidly mounted to the side of linear actuator 126 so that they remain stationary with respect to the side of linear actuator 126 along the z-axis. Linear actuator 126 is mounted to linear actuator 121 so that it can move along the y-axis.

Platform 182 is mounted to linear actuator 180 so that it can move along the x-axis. Locating plate 4A is placed on top of platform 182. Platform 102 is mounted to linear actuator 115 so that it can move along the x-axis. Microplate 190 is place on top of platform 102. In this preferred embodiment platform 102 has the capacity to hold ten microplates 190.

Solution in microplate 190 is removed via dispense tips 107. Linear actuator 126 then moves along the y-axis so that dispense tips 107 are above locating plate 4A. The solution is then spotted in a fashion similar to that described for the earlier preferred embodiments. Camera 112 with strobe 113 is focused so as to permit recording of the deposition process and functions to permit verification of slide identification information, permit verification of proper deposition of solution on the slides, and to verify slide alignment. As explained above, slide image data is transferred via camera 112 to a PC control system where the data is analyzed. The results of the analysis are then available for improving the spotting of the solution onto the slides. For example, spots that have failed to meet the threshold limits can be reworked. Also, the computer can automatically make adjustments to the relative positions of the slides and dispense tips based on the slide alignment analysis. Periodically, during the cycle, the dispense tips are cleaned in sonic cleaner 109, then rinsed in the rinse fountain and dried in vacuum manifold 111.

Second Preferred Embodiment has High Capacity Capability

In the second preferred embodiment, ten different microplates can be positioned on platform 102. Platform 102 is mounted on linear actuator 115. Linear Actuator 115 can move platform 102 and any microplates mounted on platform 102 so that any particular microplate is directly below dispense tips 107. The area below dispense tips 102 constitutes a solution removal area. One of ordinary skill in the art will recognize that by making platform 102 larger, the number of solution filled microplates positioned on platform 102 can be increased, thereby increasing the overall capacity of the second embodiment.

Operation of the First Preferred Embodiment with the Second Preferred Embodiment The first preferred embodiment (described in the sequence illustrated in FIGS. 3–32) can be used in conjunction with the second preferred embodiment to spot slides. For example as shown in FIG. 32, locating plate 4A can be removed from the microarrayer via an operator after it has been spotted with a base solution. Locating plate 4A can be transferred to the microarrayer depicted in FIG. 41. It can be placed on platform 180. DNA from microplate 190 can then be spotted on top of the base solution spotted already on slides 4A1–4A10.

Third Preferred Embodiment

Figure 42:
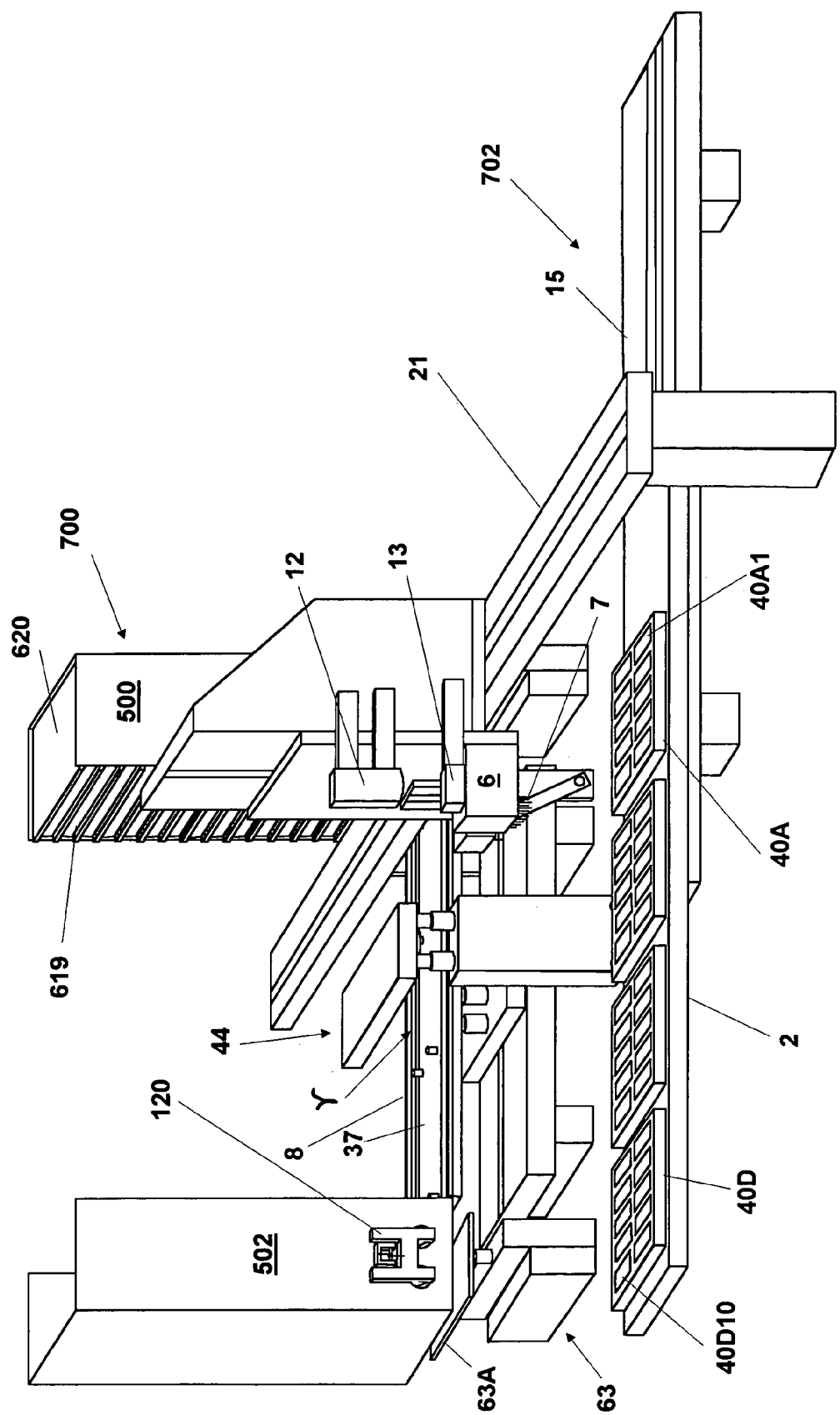
FIG. 42 shows a third preferred embodiment of the present invention.

A perspective view of the third preferred embodiment is seen by reference to FIG. 42. The third preferred embodiment is similar to the second preferred embodiment in that it has the advantage of accommodating high capacity microplate handling capabilities. The third preferred embodiment of the present invention utilizes microplate indexing station 700, also shown in FIGS. 44A and 44B. Embodiments of microplate indexing station 700 were described in detail in U.S. application Ser. No. 09/411,943, the specification of which is herein incorporated by reference. In U.S. application Ser. No. 09/411,943, microplate indexing station 700 was described as being used in conjunction with an automated microplate filling device and it included a microplate fill nozzle. In the third preferred embodiment of the present invention, microplate indexing station 700 is used in conjunction with other components to dispense solution onto slides.

Overview of the Operation of the Third Preferred Embodiment

During the operation of the present invention, solution filled microplates are stacked inside input chamber 500 of microplate indexing station 700, as shown in FIG. 42. They are then sequentially moved towards output chamber 502 via walking beam indexer 37. When a microplate reaches position $\gamma$, its lid is removed via lid lifter 44. (FIG. 44B shows a top view of microplate indexing station 700 with microplates at five different positions $\alpha$, $\beta$, $\gamma$, $\delta$, and $\epsilon$.) Lid lifter 44 then moves the microplate lid out of the way via lid lifter retractor 750 (FIGS. 44A, 44B, 67–68). Solution can then be extracted from the microplate via dispense tips 7 mounted on dispense head 6. The solution is then deposited on slides located at slide station 702. After the solution has been removed from the microplate at position $\gamma$, its lid is replaced via lid lifter 44 and the microplates are sequentially stacked inside output chamber 502. During the course of operation of this embodiment, dispense head 6 is moved back and forth between microplate indexing station 700 and slide station 702 via linear actuator 21. Slides at slide station 702 are moved from left to right via linear actuator 15.

Figure 43A:
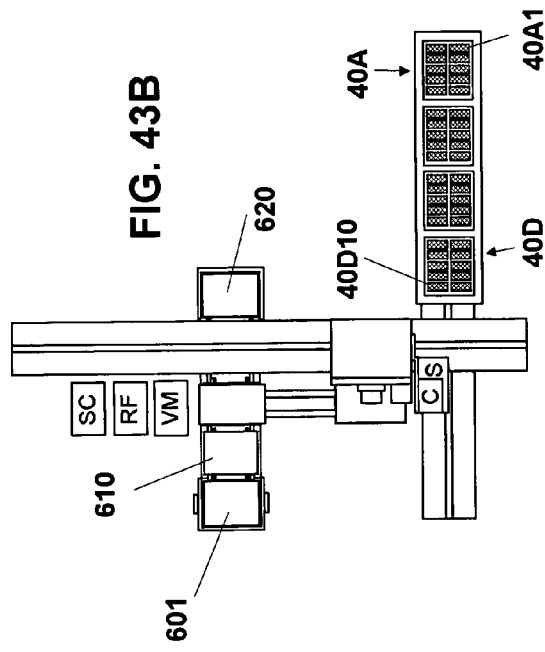
FIGS. 43A–43D show a sequence of operation of the third preferred embodiment.
Figure 43B:
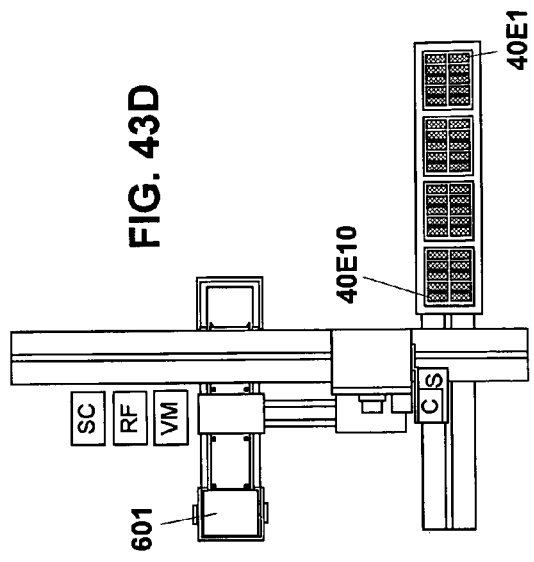
Figure 43C:
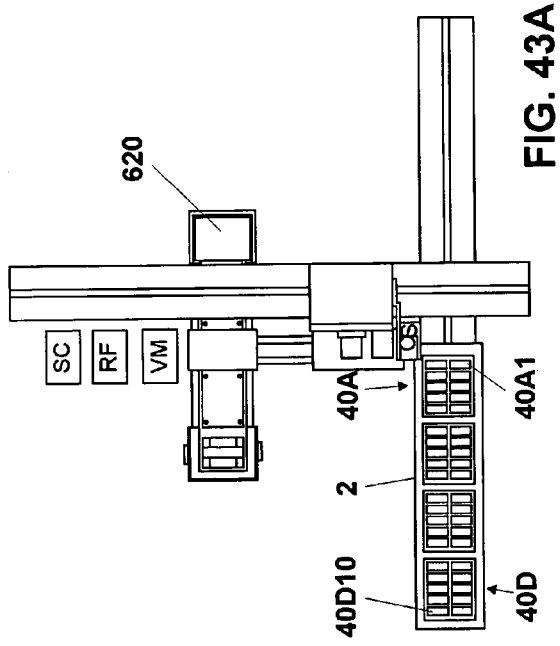
Figure 43D:
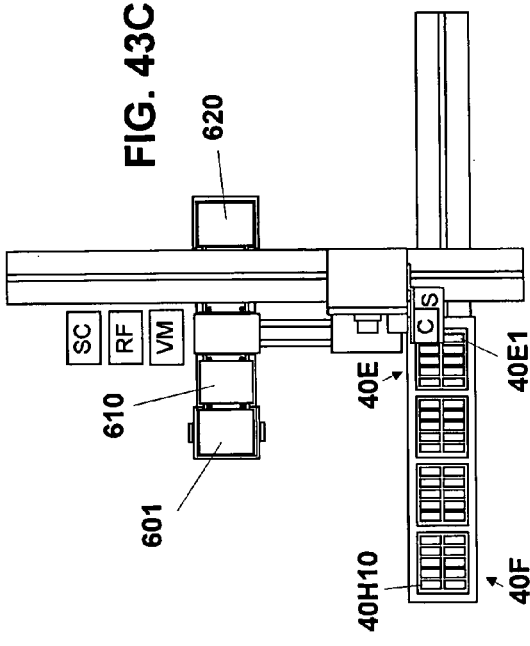

In the third preferred embodiment, dispensing tips 7 (FIG. 42) will remove solution from each well of each of the first ten of the twenty 384-well microplates (i.e., microplates 601–610) and deposit a corresponding spot on each of the slides 40A1–40D10 (FIG. 43B). Then the operator will remove locating plates 40A–40D and replace them with locating plates 40E–40H each having ten clean, blank slides 40E1–40H10 (FIG. 43C). Likewise, the 40 slides on plates 40E–40H will be spotted with the second ten of the twenty 384-well microplates in input chamber 500 (i.e, microplates 611–620) (FIG. 43D).

In the third preferred embodiment, the total number of wells in microplates 601–620 are 384×20=7680 wells. Since there are 96 etched positions on each slide and there are 80 slides on plates 40A–40H, the total number of etched positions available to receive a spot from dispense tips 7, are 96×80=7680.

Detailed Sequence of Operation of the Third Preferred Embodiment

Figure 78A:
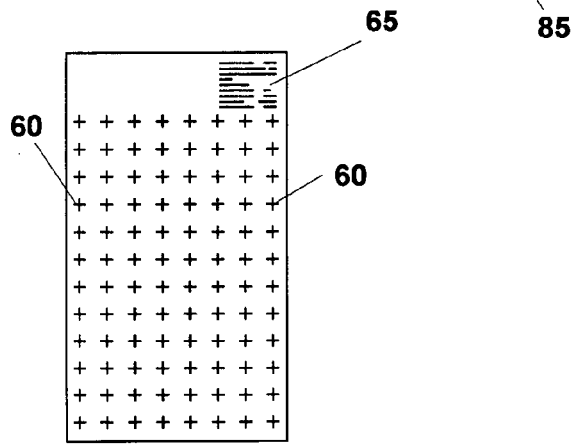
FIGS. 78A–78E show slides.

As shown in FIGS. 42 and 43A, an operator places four locating plates 40A–40D each having ten clean, blank slides 40A1–40D10 on platform 2. A preferred slide is shown in FIG. 78A. It has ninety-six etched dispense positions 60 and has its own unique 2D bar code 65 for identification purposes.

Figure 45:
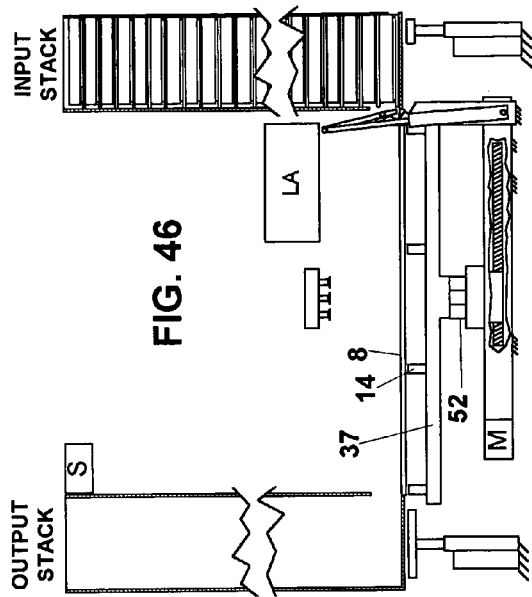

The operator then deposits twenty solution filled microplates 601–620 into input chamber 500 (FIGS. 42, 43A, 45). In a preferred embodiment, microplates 601–620 are each 384-well microplates.

Microplates Sequentially Moved to Position $\gamma$ for Lid Removal

In the third preferred embodiment of the present invention, the operation of the components is controlled by programmable logic controller (PLC) 300, as shown in FIGS. 88 and 89. FIG. 89 shows the major components associated with microplate indexing station 700.

The user powers "on" the present invention, PLC 300 automatically conducts a start up routine. In this routine, PLC 300 checks all PLC 300 controlled components, homes all pneumatic devices and checks all sensors. If there are any errors (for example, jammed microplates or component malfunction), the user will be alerted via monitor 305.

The user inputs via a computer interface the type of microplates that are stacked in input chamber 500 (i.e., either a single-well, 96-well, or 384-well microplate). In this preferred embodiment, microplates 601–620 are 384-well microplates. Depending upon the microplate selected by the user in the start up routine, PLC 300 selects walking beam indexer 37 positioning data.

All components move to their start position. FIG. 45 shows a stack of twenty filled microplates 601–620 loaded into input chamber 500. Microplate 601 is at the bottom at position α (FIG. 44B) and microplate 602 is directly above microplate 601. Microplate 620 is at the top of the stack. In FIG. 45 output stack 502 is empty with no microplates.

Figure 46:
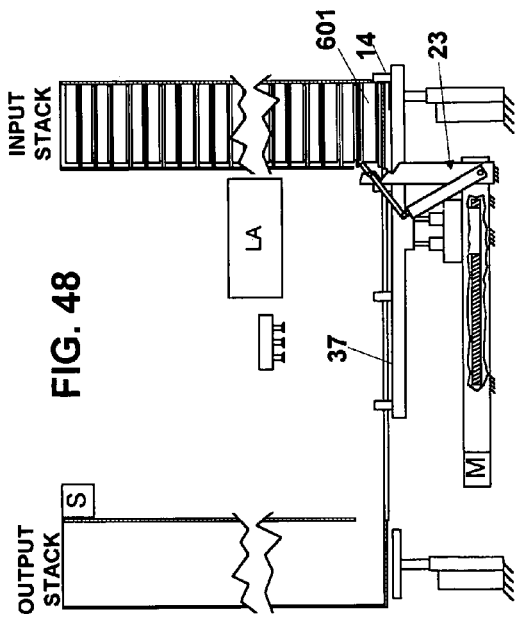

In FIG. 46, walking beam indexer 37 is lowered via pneumatic cylinders 52 so that dowel pins 14 are below the horizontal plane formed by the top surface of beam 8.

Figure 47:
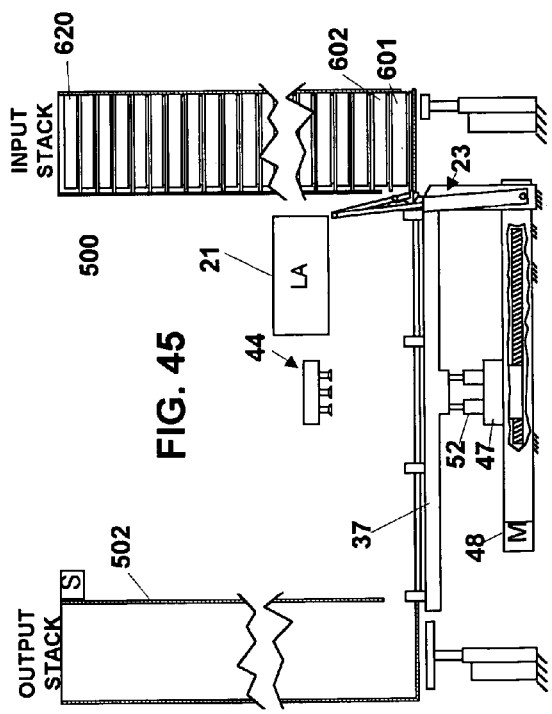
Figure 87:
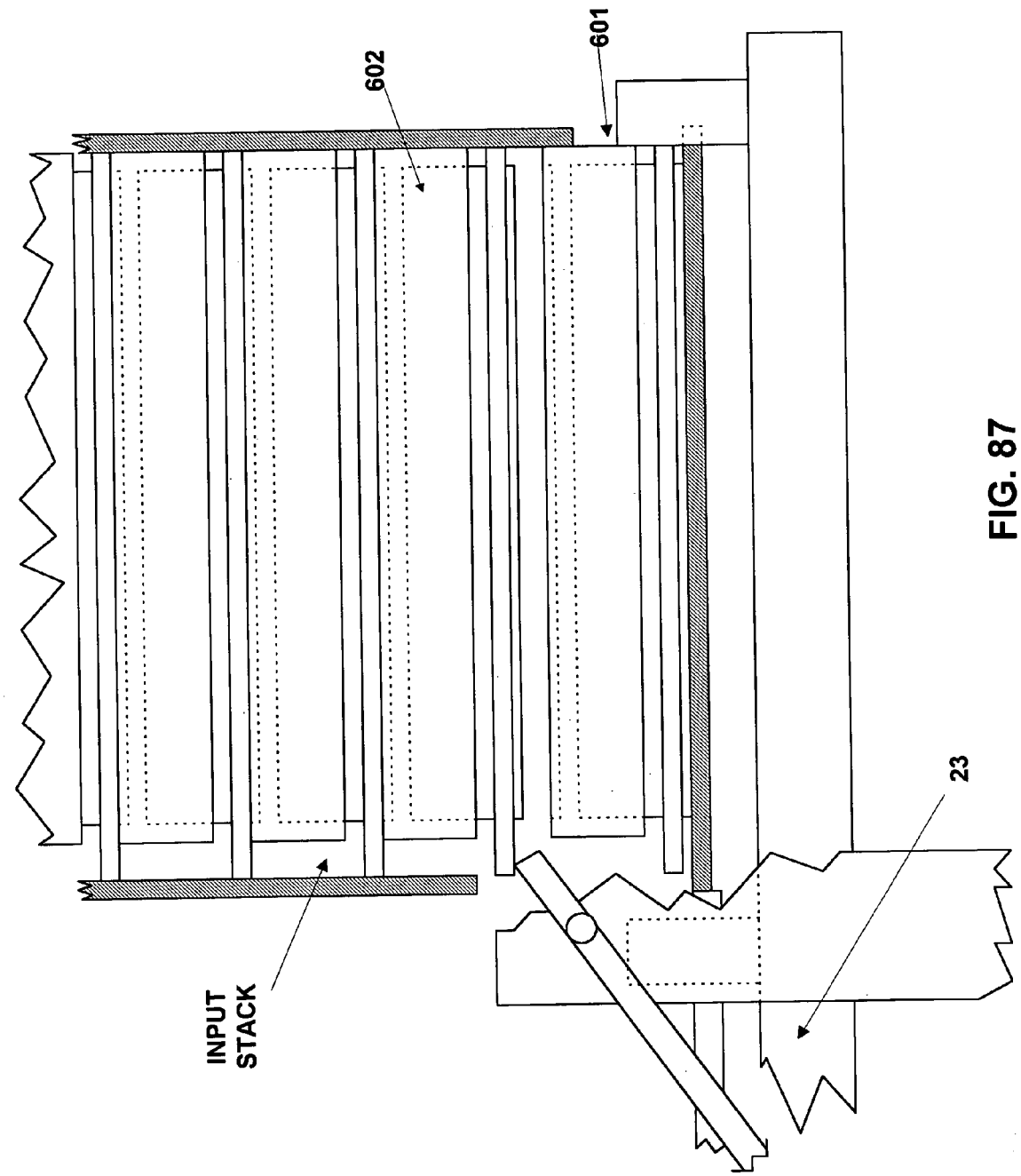
FIG. 87 shows a detailed view of the input singulator.

In FIG. 47, input chamber singulator 23 has lifted input stack 602–620 at microplate 602. Microplate 601 is left at position a, as shown in FIG. 44B. A detailed view of input chamber singulator 23 lifting input stack 602–620 is seen in FIG. 87. (Input chamber singulator 23 was described in detail in U.S. patent application Ser. No. 09/441,943). Input chamber singulator 23 lifts microplate 602 allowing a small gap to form between microplate 601 and 602. Since input stack 602–620 is confined on all sides by input chamber 500, instead of tilting input stack 602–620, lifting from the front edge lifts the entire stack vertically. Also, as shown in FIG. 47, walking beam indexer 37 has moved to the right.

Figure 48:
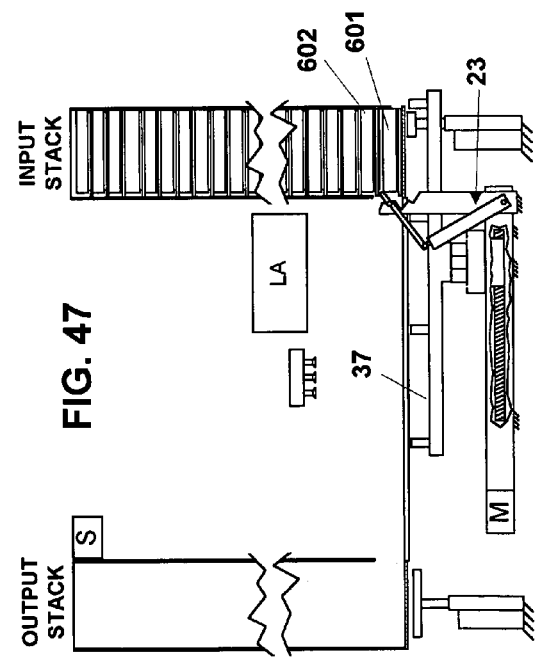

In FIG. 48, walking beam indexer 37 is raised so that dowel pin 14 is located directly behind microplate 601.

In FIG. 49, walking beam indexer 37 has moved to the left pushing microplate 601 to position β, (see FIG. 4) from the bottom of the stack. As soon as microplate 601 is no longer above input chamber lifter 802, input chamber lifter 802 moves upward so that it is supporting input stack 602–620 along with input chamber singulator 23.

In FIG. 50, walking beam indexer 37 has been lowered so that dowel pins 14 are below the horizontal plane formed by the top surface of beam 8. Input chamber singulator 23 and input chamber lifter 802 has lowered the input stack. Microplate 601 is at position β and microplate 602 is at position α.

In FIG. 51, walking beam indexer 37 has moved to the right. Input chamber singulator 23 has lifted input stack 603–620, leaving behind microplate 602 at position α.

In FIG. 52, walking beam indexer 37 is raised so that dowel pin 14 is located directly behind microplate 602.

In FIG. 53, walking beam indexer 37 has moved to the left. Microplate 601 is at position γ and microplate 602 is at position β (FIG. 44B). As soon as microplate 602 is no longer above input chamber lifter 802, input chamber lifter 802 moves upward so that it is supporting input stack 603–620 along with input chamber singulator 23.

In FIG. 54, lid lifter 44 has dropped to the top of microplate lid 27 of microplate 601 and has grasped microplate lid 27 with a vacuum force via lid lifter vacuum cups 41B.

In FIG. 55, lid lifter 44 has lifted microplate lid 27. Microplate 601 is at position γ (see FIG. 44B) and microplate 602 is at position β. (The side view shown in FIG. 55 corresponds to the top view shown in FIG. 67.)

In FIGS. 56 and 68, lid lifter 44, via lid lifter retractor 750, has moved microplate lid 27 out of the way so that it is no longer directly above microplate 601.

Dispense Head Moved so it is Above the Microplate at Position γ

In a preferred embodiment the following steps occur concurrently with the procedure described referring to FIGS. 45–56.

FIG. 61 is a top view of the present invention and corresponds with the perspective drawing shown in FIG. 42. As shown in FIG. 62, linear actuator 15 moves platform 2 and linear actuator 21 moves linear actuator 26 so that dispense head 6 is positioned directly above slide 40A1. Using camera 12 and the strobe light 13, an image is acquired of slide 40A1. The camera reads the bar code and inspects the positioning and alignment of slide 40A1 on locating plate 40A. The software then analyzes the position data and stores the information. The information stored and will be used later to adjust the positions of slide 40A1 and dispense head 6 to ensure accurate placement of the solution on the slide.

After camera 12 has acquired the image of slide 40A1, linear actuator 26 is moved via linear actuator 21 to the position shown in FIG. 63 so that dispense head 6 is directly above slide 40A2. Using camera 12 and the strobe light 13, an image is acquired of slide 40A2. As with slide 40A1, camera reads the bar code and inspects the positioning and alignment of slide 40A2 on locating plate 40A. The software then analyzes the position data and stores the information. The information stored and will be used later to adjust the positions of slide 40A2 and dispense head 6 to ensure accurate placement of the solution on the slide.

Linear actuator 26 is then moved via linear actuator 21 to the position shown in FIG. 64 so that dispense head 6 is directly above sonic cleaner 9. Dispense tips 7 are dipped into sonic cleaner 9 and then raised. The procedure for dipping dispense tips 7 into sonic cleaner 9 is described in detail above.

Linear actuator 26 is then moved via linear actuator 21 to the position shown in FIG. 65 so that dispense head 6 is directly above rinse fountain 10. Dispense tips 7 are dipped into rinse fountain 10 and then raised. The procedure for dipping dispense tips 7 into rinse fountain 10 is also described in detail above.

Linear actuator 26 is then moved via linear actuator 21 to the position shown in FIG. 66 so that dispense head 6 is directly above vacuum manifold 11. Dispense tips 7 are dipped into vacuum manifold 11 and then raised. The procedure for dipping dispense tips 7 into vacuum manifold 11 is also described in detail above.

The cleaning cycle described in FIGS. 64–66 can be set by the user, via the computer interface, to be repeated as many times as necessary.

Solution is Removed From the Microplate at Position γ

As shown in FIGS. 69 and 70, linear actuator 26 is moved so that dispense head 6 is directly above microplate 601 at position γ. (FIG. 44B).

Mounting plate 25 is then lowered via linear actuator 26 so that tips 7 are dipped into microplate 601, as shown in FIG. 71. While in microplate 601 dispense tips 7 pick up some of the solution to be dispensed.

Figure 77:
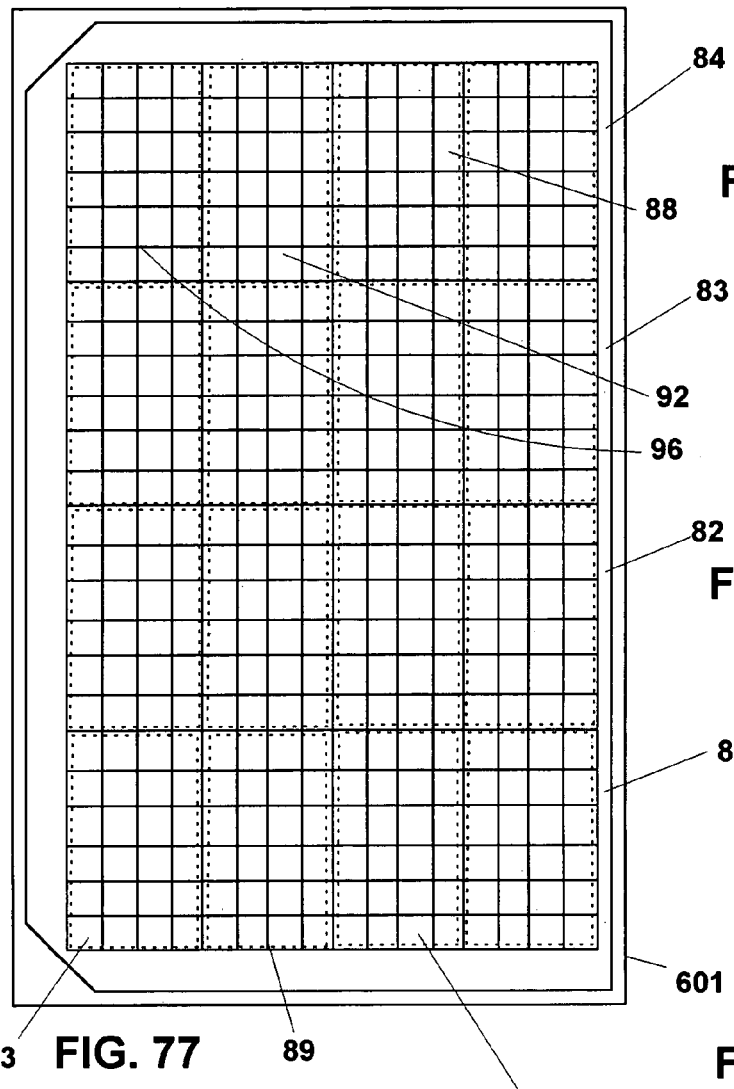
FIG. 77 shows a top view of a microplate.

An enlarged top view of microplate 601 is shown in FIG. 77. When dispense tips 7 are first dipped into microplate 601, solution is removed from the 4×6 array at first removal position 81.

Mounting plate 25 is then raised via linear actuator 26, as shown in FIG. 72.

Figure 73:
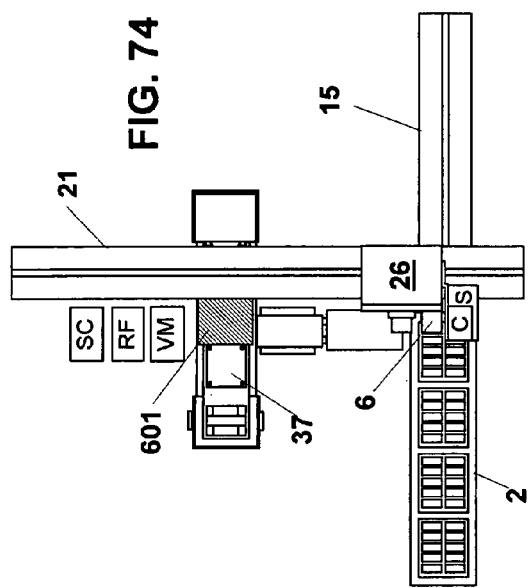

Linear actuator 26 then moves so that dispense head 6 is above slide 40A1, as shown in FIG. 73. Based on the earlier positioning data regarding slide 40A1, linear actuator 21 makes minute positioning adjustments to linear actuator 26 and linear actuator 15 makes minute positioning adjustments to platform 2 in order to accurately position dispense head 6 over slide 40A1 at the first dispense position.

Figure 78B:
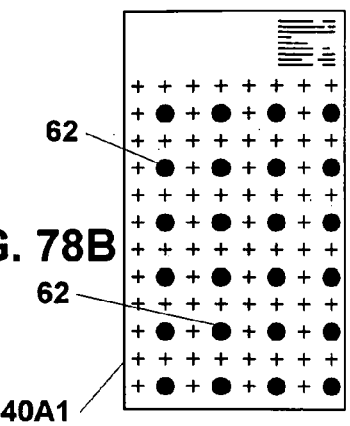

Dispense head 6 is then lowered via linear actuator 26 so that tips 7 are in contact with slide 40A1 at the first dispense position. As tips 7 contact slide 40A1 at the first dispense position, spots 62 are placed on slide 40A1 via surface tension, as shown in FIG. 78B.

Dispense head 6 is raised via linear actuator 26. Linear actuator 26 is moved via linear actuator 21 so that it is above microplate 601 at position γ (FIG. 44B), as shown in FIGS. 69 and 70. Then positioning adjustments are made to linear actuator 26 and to walking beam indexer 37 so that dispense head 6 is directly above microplate 601 at second removal position 82, as shown in FIG. 77.

Mounting plate 25 is then lowered via linear actuator 26 so that dispense tips 7 are dipped into microplate 601 at second removal position 82. While in microplate 601 dispense tips 7 pick up some of the solution to be dispensed.

Linear actuator 26 then moves so that it is positioned over slide 40A1. Based on the earlier positioning data regarding slide 40A1, linear actuator 21 makes minute positioning adjustments to linear actuator 26 and linear actuator 15 makes minute positioning adjustments to platform 2 in order to accurately position dispense head 6 over slide 40A1 at the second dispense position.

Figure 78C:
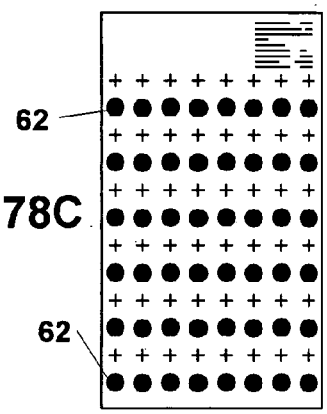

Dispense head 6 is then lowered via linear actuator 26 so that tips 7 are in contact with slide 40A1 at the second dispense position. As tips 7 contact slide 40A1 at the second dispense position, spots 62 are placed on slide 40A1 via surface tension, as shown in FIG. 78C.

Figure 78D:
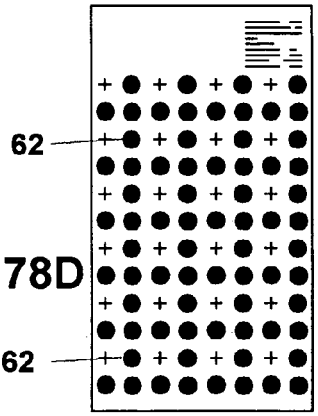
Figure 78E:
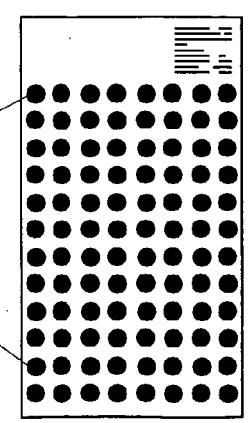

Dispense head 6 is raised via linear actuator 26. In a fashion similar to that just described, solution is removed from microplate 601 at third removal position 83 and then deposited on slide 40A1 at the third dispense position so that spots 62 are deposited as shown in FIG. 78D. Then, solution is removed from microplate 601 at fourth removal position 84 and deposited on slide 40A1 at the fourth dispense position so that spots 62 are deposited as shown in FIG. 78E. Slide 40A1, as shown in FIG. 78E, has been completely spotted.

After slide 40A1 has been completely spotted, camera 12 and strobe 13 scans slide 40A1 and acquires images and inspects for spot quality. It is at this point that PC control system 300 (FIGS. 88–89) identifies slide 40A1 as pass or fail. (Preferred computer controlled techniques for making this determination were discussed in a preceding section.)

Figure 74:
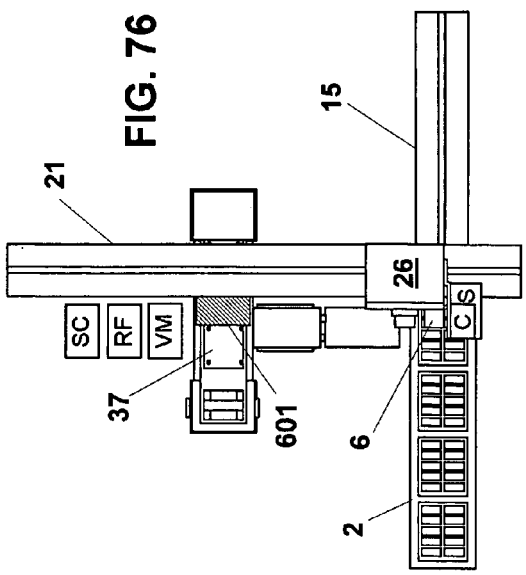

After slide 40A1 has been inspected for spot quality, walking beam indexer 37 moves slightly to the right, as shown in FIG. 74. Linear actuator 26 is moved via linear actuator 21 to a position above microplate 601 at position 7 (FIG. 44B). Then, positioning adjustments are made to linear actuator 26 and to walking beam indexer 37 so that dispense head 6 is directly above microplate 601 at fifth removal position 85, as shown in FIG. 77. Solution is then removed from fifth removal position 85.

As shown in FIG. 74, linear actuator 26 is then moved so that it is above slide 40A2. Based on the earlier positioning data regarding slide 40A2, linear actuator 21 makes minute positioning adjustments to linear actuator 26 and linear actuator 15 makes minute positioning adjustments to platform 2 in order to accurately position dispense head 6 over slide 40A2 at its first dispense position.

Dispense head 6 is then lowered via linear actuator 26 so that tips 7 are in contact with slide 40A2 at its first dispense position. In a fashion similar to that described regarding slide 40A1, slide 40A2 is completely spotted utilizing solution removed from removal positions 85–88. Camera 12 and strobe 13 scans slide 40A2 and acquires images and inspects for spot quality. It is at this point that the control system identifies slide 40A2 as pass or fail.

After slide 40A2 has been completely spotted, camera 12, utilizing light provided by strobe 13, will record the positions of slides 40A3 and 40A4. Then, walking beam indexer 37 and platform 2 move slightly to the right, as shown in FIG. 75.

The cleaning cycle is repeated. In summary, dispense tips 7 are dipped in sonic cleaner 9. Dispense tips 7 are then rinsed in rinse fountain 10. Then, dispense tips 7 are dried in vacuum manifold 11. Preferably, dispense tips 7 are cleaned after every two slides have been completely spotted. However, the frequency of cleaning may be adjusted as is appropriate.

Linear actuator 26 is moved via linear actuator 21 to a position above microplate 601. Then, positioning adjustments are made to linear actuator 26 and to walking beam indexer 37 so that dispense head 6 is directly above microplate 601 at ninth removal position 89, as shown in FIG. 77. Solution is then removed from ninth removal position 85.

Figure 75:
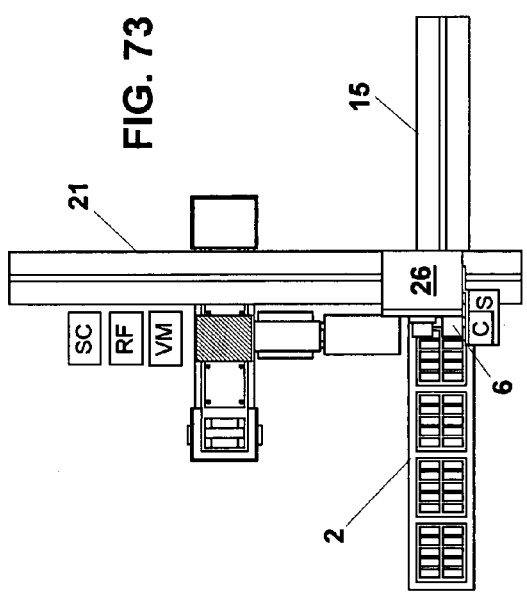

As shown in FIG. 75, linear actuator 26 is then moved so that it is above slide 40A3. Based on the earlier positioning data regarding slide 40A3, linear actuator 21 makes minute positioning adjustments to linear actuator 26 and linear actuator 15 makes minute positioning adjustments to platform 2 in order to accurately position dispense head 6 over slide 40A3 at its first dispense position.

Dispense head 6 is then lowered via linear actuator 26 so that tips 7 are in contact with slide 40A3 at its first dispense position. In a fashion similar to that described regarding slide 40A1, slide 40A3 is completely spotted utilizing solution removed from removal positions 89–92.

Figure 76:
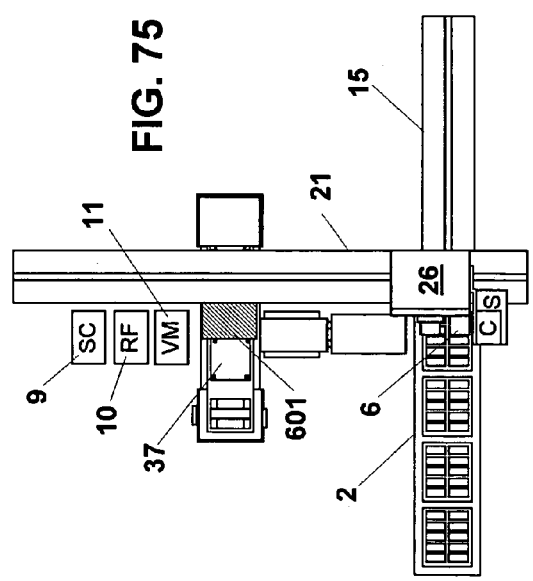

After slide 40A3 has been completely spotted, walking beam indexer 37 moves slightly to the right, as shown in FIG. 76. Linear actuator 26 is moved via linear actuator 21 to a position above microplate 601. Then, positioning adjustments are made to linear actuator 26 and to walking beam indexer 37 so that dispense head 6 is directly above microplate 601 at thirteenth removal position 93, as shown in FIG. 77. Solution is then removed from thirteenth removal position 93.

As shown in FIG. 76, linear actuator 26 is then moved so that it is above slide 40A4. Based on the earlier positioning data regarding slide 40A4, linear actuator 21 makes minute positioning adjustments to linear actuator 26 and linear actuator 15 makes minute positioning adjustments to platform 2 in order to accurately position dispense head 6 over slide 40A4 at its first dispense position.

Dispense head 6 is then lowered via linear actuator 26 so that tips 7 are in contact with slide 40A4 at its first dispense position. In a fashion similar to that described regarding slide 40A1, slide 40A2 is completely spotted utilizing solution removed from removal positions 93–96.

After slides 40A1–40A4 have been spotted, microplate lid 27 is moved via lid lifter 44 over microplate 601 at position γ, as shown in FIG. 79. Microplate lid 27 is then lowered onto microplate 601, as shown in FIG. 54.

Repeat Spotting Sequence for the Remaining Microplates 602–620

Figure 57:
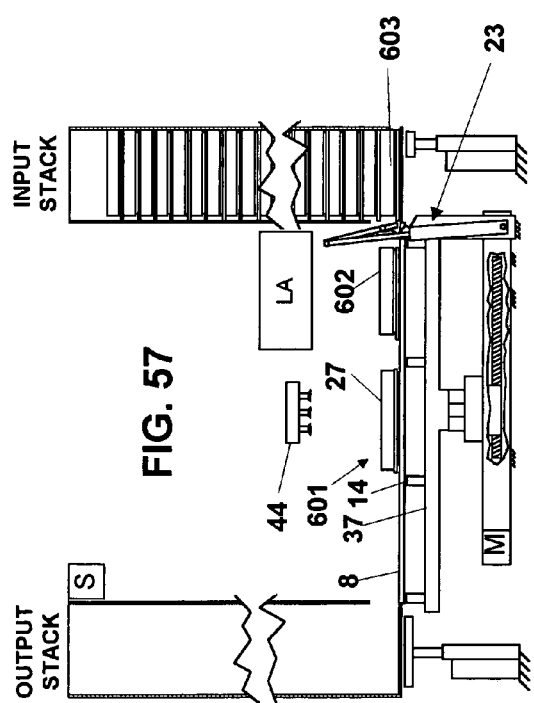

In FIG. 57, lid lifter 44 is raised, leaving behind microplate lid 27 on microplate 601. Input chamber singulator 23 and input chamber lifter 802 have has lowered input stack 603–620. Microplate 601 is at position γ (FIG. 44B), microplate 602 is at position β, and microplate 603 is at position α. Walking beam indexer 37 has been lowered so that dowel pins 14 are below the horizontal plane formed by the top surface of beam 8.

Figure 58:
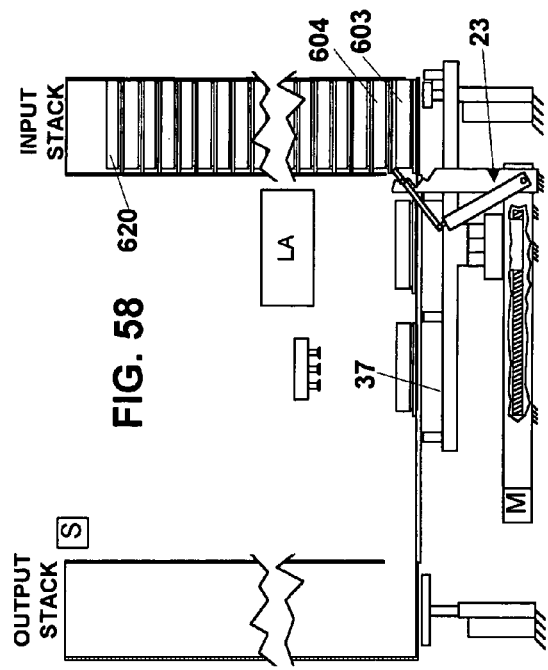

In FIG. 58, walking beam indexer 37 has moved to the right. Input chamber singulator 23 has lifted input stack 604–620, leaving behind microplate 603 at position α.

Figure 59:
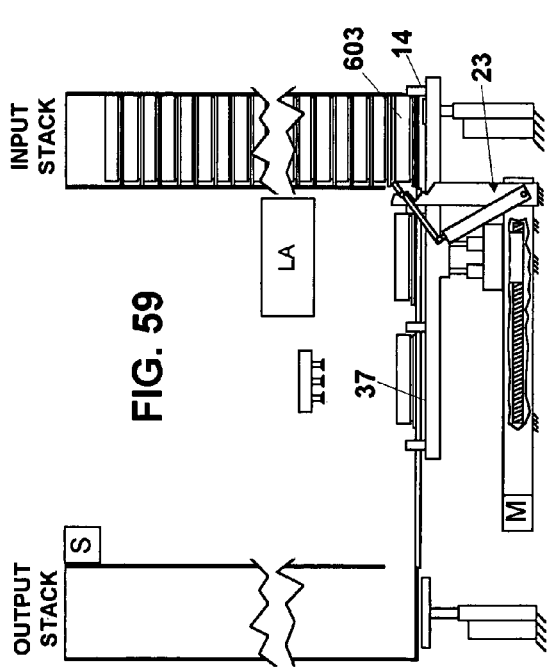

In FIGS. 59 and 79, walking beam indexer 37 is raised so that dowel pin 14 is located directly behind microplate 603.

Figure 60:
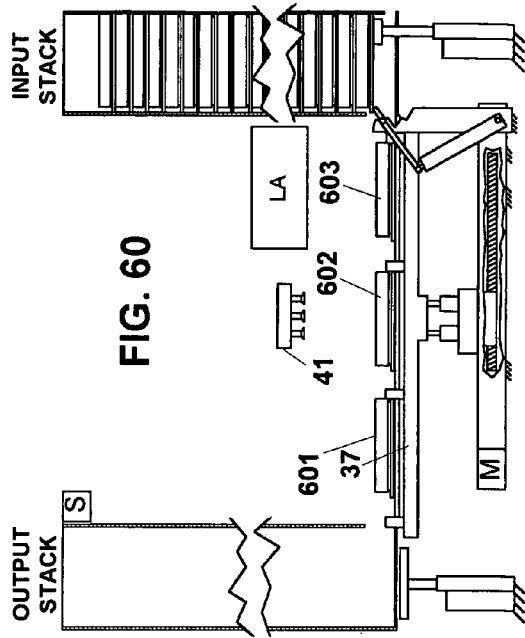

In FIGS. 60 and 80, walking beam indexer 37 has moved to the left. Microplate 601 is at position δ, microplate 602 is at position γ, microplate 603 is at position γ (FIG. 44B).

In FIG. 81, microplate lid 27 has been removed from microplate 602. Solution has been removed from the first removal position of microplate 602 and is being deposited at the first dispense position of slide 40A5. In a fashion similar to that described above, solution will continue to be removed from microplate 602 until slides 40A5–40A8 are completely spotted.

In FIG. 82, microplate 601 is at position ε inside output chamber 502, microplate 602 is at position δ, microplate 603 is at position γ, and microplate 604 is at position β (FIG. 44B). Dispense head 6 is positioned over slide 40A9. In a fashion similar to that describe above, solution will be removed from microplate 603 to spot slides 40A9–40B2.

Figure 83:
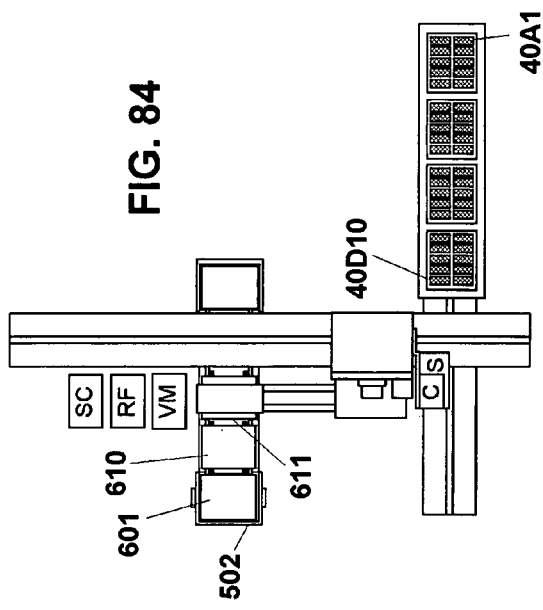

In FIG. 83, microplate 602 is at position ε inside output chamber 502 and underneath microplate 601, microplate 603 is at position δ, microplate 604 is at position γ, and microplate 605 is at position β (FIG. 44B). Output chamber lifter 63 is shown in FIG. 42 and it used for restacking the microplates inside output chamber 502. The procedure for restacking microplates inside output chamber 502 is described in detail later in this specification under the heading "Output Chamber Utilizing Output Chamber Lifter with Stack Support Pieces". Lid lifter 44 has removed microplate lid 27 from microplate 604 and has retracted microplate lid 27 so that it is not above microplate lid 604. In a fashion similar to that describe above, solution will be removed from microplate 604 to spot slides 40B3–40B6.

Figure 84:
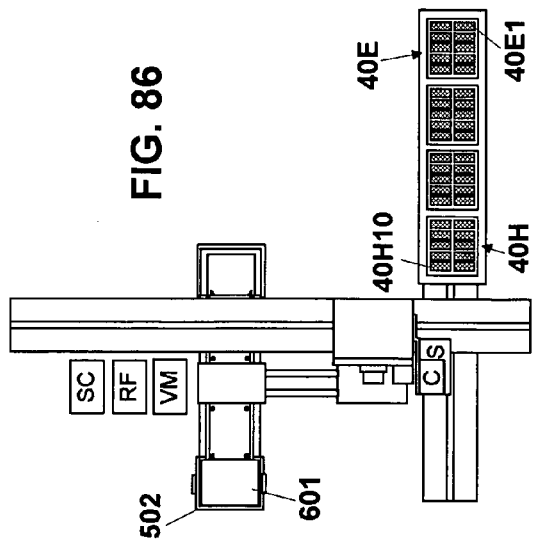

In FIG. 84, solution has been removed from microplates 601–610 and spotted on slides 40A1–40D10. Microplate 609 is at position ε inside output chamber 502 and directly underneath microplate 608, microplate 610 is at position δ, microplate 611 is at position γ, and microplate 612 is at position β (FIG. 44B).

Figure 85:
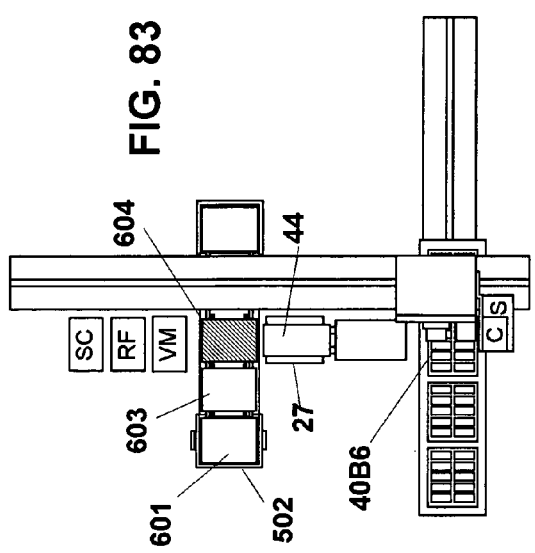

In FIG. 85, platform 2 has moved to the left via linear actuator 15. Locating plates 40E–40H containing forty slides 40E1–40H10 have been placed on platform 2. Microplate 609 is still at position ε inside output chamber 502 and directly underneath microplate 608, microplate 610 is at position δ, microplate 611 is at position γ, and microplate 612 is at position β (FIG. 44B). Lid lifter 44 has removed microplate lid 27 from microplate 611 and has retracted microplate lid 27 so that it is not above microplate lid 611.

Figure 86:
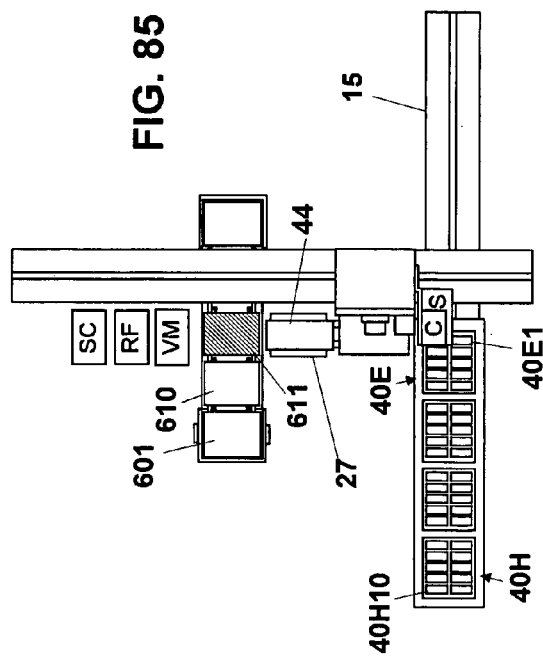

In FIG. 86, solution has been removed from microplates 611–620 and spotted on slides 40E1–40H10. Microplates 601–620 are restacked inside output chamber 502 with microplate 601 at the top of the stack and microplate 620 at the bottom of the stack. Locating plates 40E–40H have moved to the right and are ready to be removed.

Output Chamber Utilizing Output Chamber Lifter with Stack Support Pieces

Figure 90:
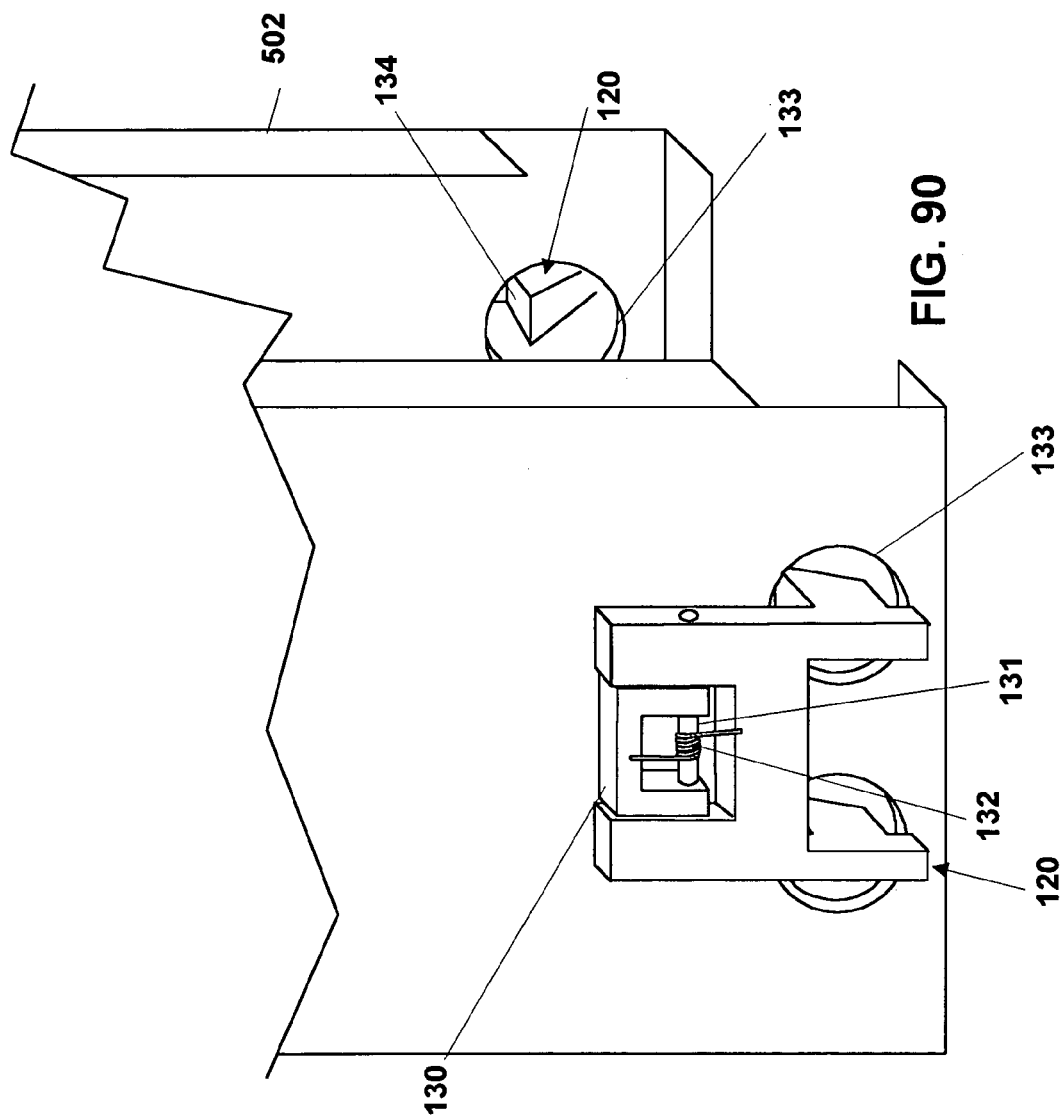
FIG. 90 shows a detailed perspective view of a preferred output chamber.

As shown in FIG. 42, output chamber 502 has two stack support pieces 120 mounted to its side. Output chamber lifter 63 is directly under output chamber 502. FIG. 90 shows a perspective view of output chamber 502 with stack support pieces 120 mounted to its side. As shown in FIG. 42, output chamber lifter 63 has a single large lifting pad 63A. Single large lifting pad 63A provides a more stable support for the output stack than does the two lifting pad output chamber lifter depicted in U.S. patent application Ser. No. 09/611,256.

Figure 91:
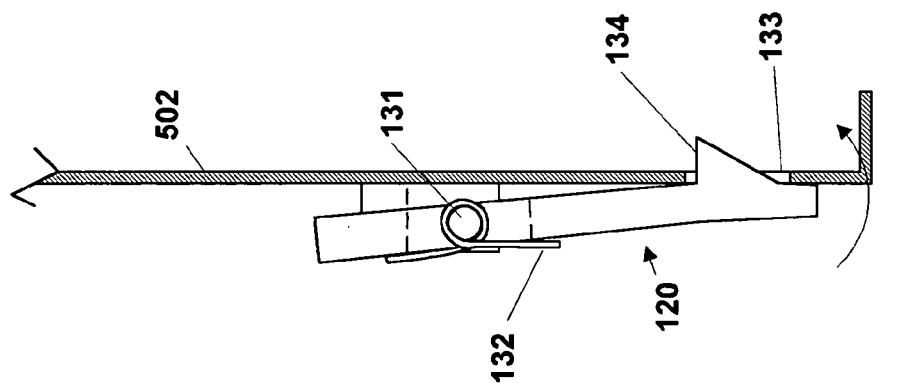

FIG. 90 shows a detailed perspective view of stack support piece 120 mounted to output chamber 502 and FIG. 91 shows a detailed side view of stack support piece 120 mounted to output chamber 502. Mount 130 is rigidly attached to output chamber 502. Axis 131 extends through mount 130 and stack support piece 120. Torsion spring 132 is wound around axis 131 and applies a force to mount 130 and stack support piece 120. This force tends to rotate stack support piece 120 in a counter-clockwise direction (FIG. 91) so that tapered support end 134 extends through hole 133 until stack support piece 120 is abutted by output chamber 502.

A sequence illustrating the operation of output chamber 502 with stack support pieces 120 is seen by reference to FIGS. 92–95.

In FIG. 92, output stack 601–606 is in output chamber 502. Microplate 606 is at the bottom of the output stack at position ε (FIG. 44B). Microplate 605 is above microplate 606 and is resting on stack support pieces 120.

In FIG. 93, output chamber lifter 63 is lifting output stack 601–606 by pressing upward on microplate 606. Tapered support end 134 of stack support piece 120 allows the upward movement of microplate 606.

Figure 94:
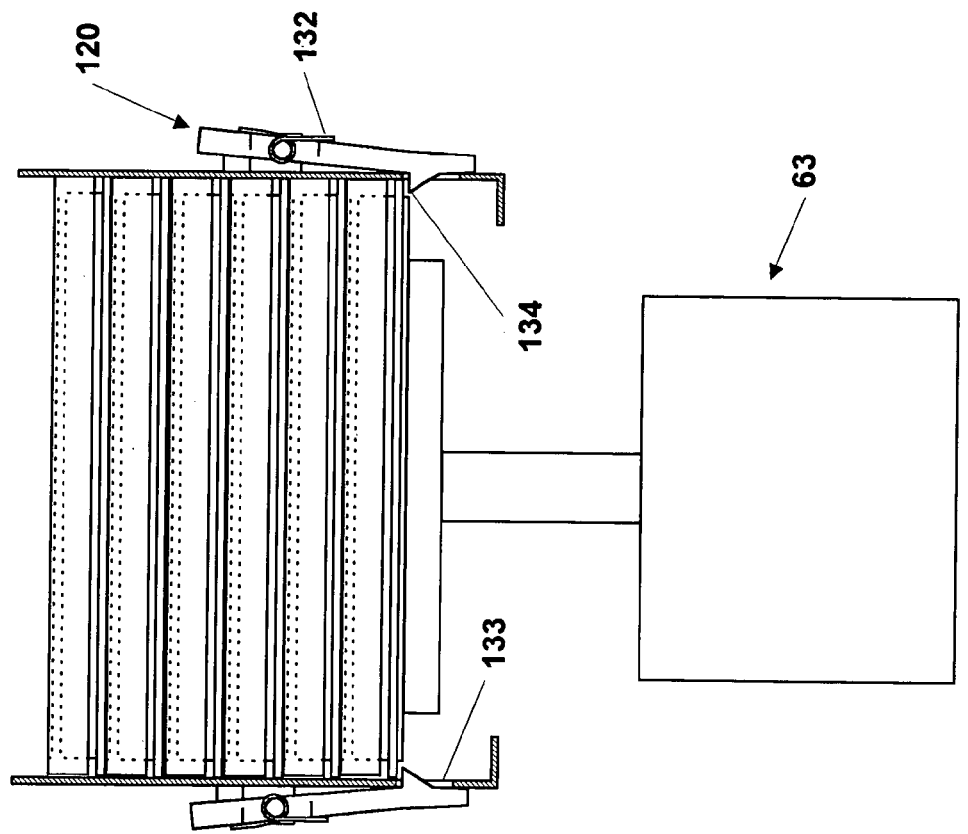

In FIG. 94, output chamber lifter 63 has lifted microplate 606 beyond tapered support ends 134. The force applied by torsion spring 132 against stack support piece 120 then moves tapered support end back through holes 133.

Figure 95:
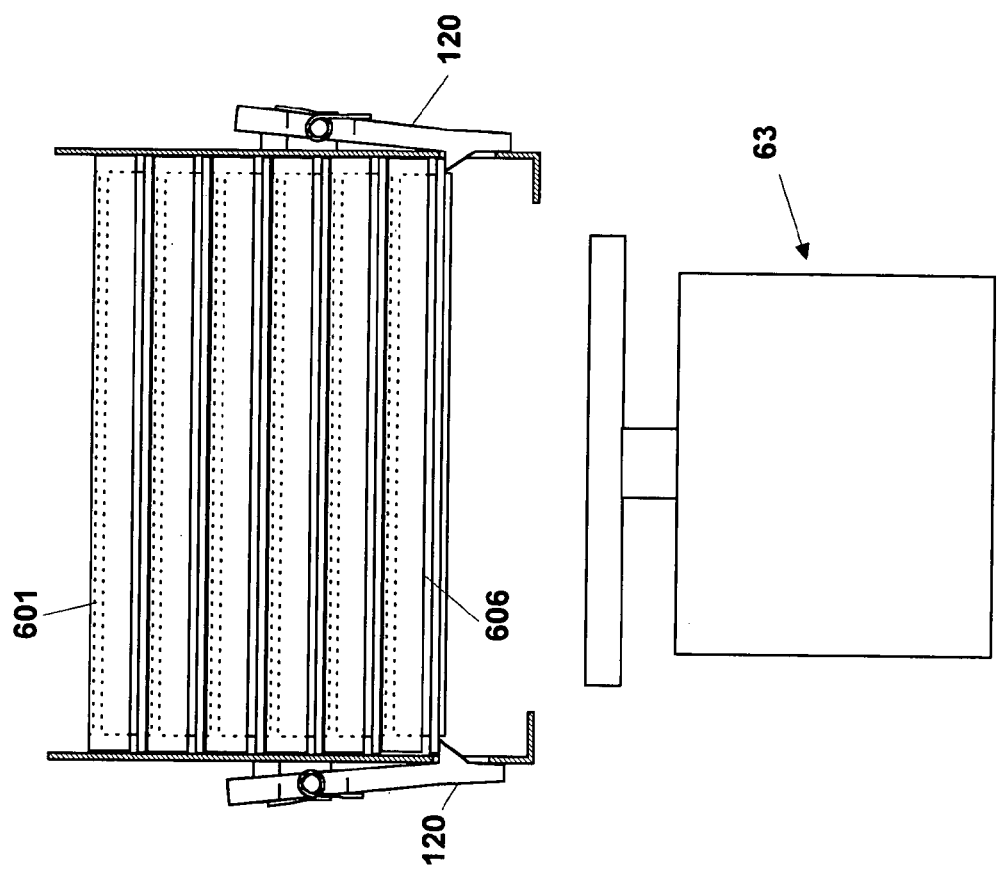

In FIG. 95, output chamber lifter 63 has lowered. Output stack 601–606 is resting on stack support pieces 120. The space at position ε (FIG. 4) is clear to make room for the next microplate in the stack.

In a fashion similar to that described by reference to FIGS. 92–95, microplates are continually stacked in the output chamber of this preferred embodiment. The embodiment utilizing output chamber lifter 63 in conjunction with stack support pieces 120 is a preferred method of stacking because a microplate can be moved into the output chamber without sliding against or contacting the microplate that is directly above it. As shown in FIGS. 92–95, there is essentially no tipping of microplates in this embodiment. As the microplates are stacked, the base of upper microplate fits snuggly into the lid of the microplate immediately below it. This helps prevent microplates from becoming askew within the output chamber and helps prevent spillage of any solution contained within the microplates.

Space Savings Advantage of the Third Preferred Embodiment

Like the second preferred embodiment, an advantage of the third preferred embodiment is that it enables a large number of slides to be automatically spotted from a large number of microplates. A further advantage of the third preferred embodiment is found by the utilization of microplate indexing station 700. The stacking and restacking capability of microplate indexing station 700 allows a large number of microplates to be indexed through position γ without wasting significant horizontal space.

Rework Capability with the Third Preferred Embodiment

As explained above, after each slide has been spotted, camera 12 and strobe 13 scans the slide and acquires images and inspects for spot quality. It is at this point that the control system identifies the slide as pass or fail. An operator monitoring the spotting process via a monitor has the option of correcting a slide that has failed.

For example, as described above with regards to earlier embodiments, an operator can scan a locating plate after the slides on it have been spotted. A good plate shows up green as in all slides pass. A plate with at least one bad spot on one of the slides shows up red. The user can then zoom in on the bad slide and the good and bad spots show up green and red respectively as pass or fail. From there, the user can decide whether or not to rework the bad spots. The procedure for reworking a failed spot was described above in reference to FIGS. 39A and 39B.

Automatic Rework Capability

The previous section described a preferred embodiment where an operator can decide whether or not to rework a spot based on a computer determination of pass or fail. As with the other preferred embodiments of the present invention, for the third preferred embodiment it is also possible for the computer to automatically rework a bad spot without operator input. In this preferred embodiment, the computer makes a determination whether or not a spot has passed or failed using the computer controlled pass-fail determination technique earlier described. If, based on its analysis, the computer determines that the spot has failed, the computer will automatically take steps to rework the spot. The procedure for automatically reworking a failed spot was also described above.

Use of the Camera and Strobe with Other Microarrayers

Although the camera 12 and strobe 13 were described as being used with the preferred microarrayers described above, those of ordinary skill in the art will recognize that it is possible to use camera 12, strobe 13 and a PC control system in conjunction with a variety of microarrayer designs. For example, in the background section of this application, several microarrayers were mentioned. It would be possible to one of ordinary skill in the art to modify a prior art automatic microarrayer to include camera 12 and strobe 13. Camera 12 and strobe 13 would then work in conjunction to provide sensory data to PC control system 300, as described above. Also, as explained above, the input would be used to accurately position the dispense heads over the slides to ensure optimum spotting and to verify the quality of the spotting as "pass" or "fail".

Modification of Rework Dispense Tips

Figure 40:
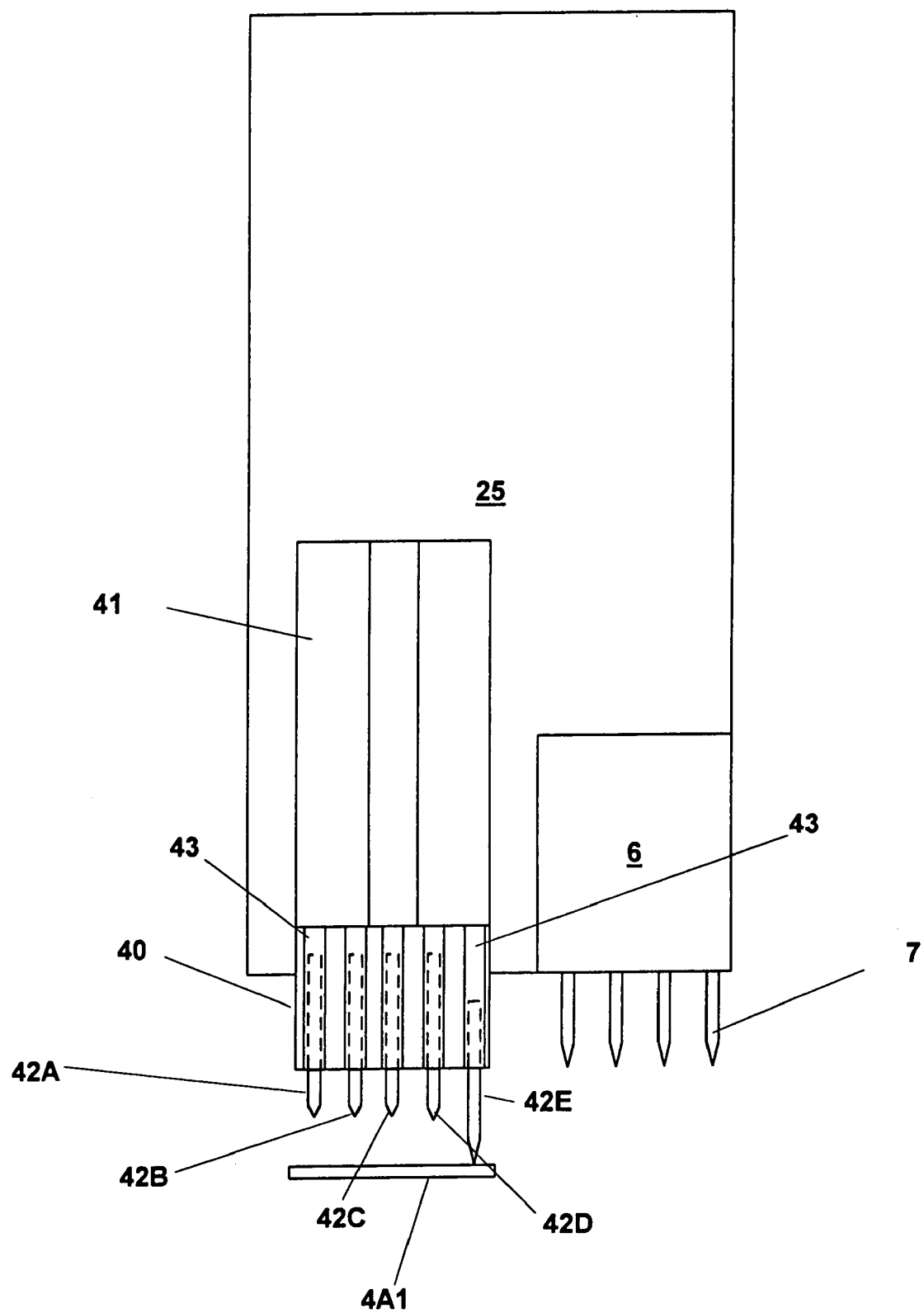
FIG. 40 shows another preferred embodiment of the present invention.

The previous embodiments showed one dispense tip 42 extending downward from dispense head 40. It was explained how the single dispense tip 42 is used for reworking (correcting) defective spots. It is possible, however, to modify dispense head 40 so that multiple dispense tips can extend downward from dispense head 40. A preferred embodiment is shown in FIG. 40 in which five dispense tips 42A–E extend down below dispense head 40. In this preferred embodiment, dispense tips 42A–E are retractably connected to dispense head 40. As shown in FIG. 40, dispense tips 42A–D are retracted inside dispense head 40. The rightmost dispense tip 42E is extended below the other dispense tips and is spotting slide 4A1. In a preferred embodiment, dispense tips 42A–E are mounted to a pneumatic slides 43.

An advantage of this embodiment is that each dispense tip 42 can be configured to dispense a different volume of solution. For example, in a preferred embodiment, dispense tip 42A would dispense 1 nL of solution, dispense tip 42B would dispense 2 nL of solution, dispense tip 42C would dispense 4 nL of solution, dispense tip 42D would dispense 8 nL of solution, and dispense tip 42E would dispense 16 nL of solution.

After initially spotting the slides as explained above, camera 12 and strobe 13 would work in conjunction to provide sensory data to PC control system 300 reporting the quality of the spots. The spots would then be classified as pass or fail. If a spot has failed, the software in conjunction with PC control system 300 would determine the amount of solution required to correct the failed spot. Then, during the reworking sequence, the dispense tip that dispenses the most correct volume would be extended down from dispense head 40 and the other dispense tips would be retracted upward inside dispense head 40, as shown in FIG. 40.

While the above description contains many specifications, the reader should not construe these as limitations on the scope of the invention, but merely as exemplifications of preferred embodiments thereof. Those skilled in the art will envision many other possible variations are within its scope. For example, although the above sequence described a dispensing process utilizing slides that have 96 dispense positions, those of ordinary skill in the art will recognize that it is possible to use other slides as well. For example, 384 or 1536 position slides could be used. It is also possible to use a blank microscope slide with no pre-etched dispense positions. Accordingly, the location of the different dispense positions will vary depending on the type of slide being used. The spacing and orientation of the slide can be selected by an operator through the maintenance menu on the computer interface. Also, the previous embodiments disclosed using a strobe light to illuminate the slide below the camera. One of ordinary skill in the art will recognize that it is possible to illuminate the slide with other light sources besides a strobe light. For example, the slide could be illuminated with a camera flash, a constant bright light, or a fluorescence device, such as a fluorescent LED. If a fluorescence device is used to illuminate the slide, those of ordinary skill in the art will recognize that it is possible to add a fluorescent dye to the solution being spotted to achieve more in depth characterizations. For example, by using a fluorescent LED and adding fluorescent dye to the solution, greater volume determination can be achieved based on fluorescent intensity of the spot. Also, although vibration isolated base 80 was shown in FIG. 36 as being utilized with a preferred embodiment, one of ordinary skill in the art would recognize that the present invention could function well without vibration isolated base 80. Also, although FIG. 37 showed touch screen monitor interface 305, other interfaces could also be utilized such as a keyboard interface. Also, one of ordinary skill in the art would recognize that PC control system 300 could be a laptop computer. This embodiment would achieve significant space savings. Also, in the preferred embodiment, it was mentioned that dispense tips 7 and 42 were quill type dispense tips, it would be obvious to substitute other types of dispense tips. For example, piezo type dispense tips could also be used. Also, in the third preferred embodiment, it was described how dispense tips 7 are cleaned after every two slides have been completely spotted. Those of ordinary skill in the art will recognize that it is possible to adjust the frequency in which dispense tips 7 are cleaned. For example, in an embodiment in which there is a different type of solution in each well of microplates 601–620, it would be preferable to clean dispense tips 7 immediately after solution has been spotted at each dispense position. Also, in the preferred embodiments it was described how each slide has its own unique 2D bar code 65 for identification purposes. However, one of ordinary skill in the art will recognize that there are other methods of marking the slide for identification purposes. In another preferred embodiment, an infrared camera, capable of emitting and receiving infrared signals, is mounted to the side of linear actuator 26. The camera is positioned so as to be able to observe reflected infrared energy off the slide being spotted underneath dispense head 6. In this preferred embodiment, each slide is made of a material that that is transparent to infrared energy, such as silicon. Each slide is then marked for identification purposes on its back with a marking that is reflective of infrared energy, such as a foil marking or paint marking. The infrared camera then identifies the slide by its infrared reflective marking after emitting the slide with infrared energy. Accordingly the reader is requested to determine the scope of the invention by the appended claims and their legal equivalents, and not by the examples which have been given.

We claim:

1. A high capacity microarrayer for spotting solution onto slides, comprising:
  A) a solution removal area,
  B) a microplate stacking device for stacking microplates,
  C) a microplate indexing device for sequentially indexing microplates containing solution from said microplate stacking device to said solution removal area and for sequentially indexing said microplates from said solution removal area to said microplate stacking device after at least some of said solution has been removed,
  D) a slide positioning station for positioning slides, and
  E) a dispense head for accessing said solution removal area and for removing solution from a solution filled microplate at said solution removal area to spot a slide at said slide positioning station,
  F) at least one light source capable of illuminating the slides,
  G) at least one camera operating in conjunction with said at least one light source, said at least one camera capable of acquiring and transmitting slide image data,
  H) a computer programmed to:
    1) receive said slide image data from said at least one camera,
    2) analyze said slide image data, and
    3) generate post analysis data based on said analysis of said slide image data, wherein said post analysis data comprises information relating to the success or failure of said microarrayer to successfully spot solution onto the slides, and
  I) an adjustment means for permitting adjustments to be made to said spotting of solution onto the slides wherein said adjustments are made based on said post analysis data,
  J) at least one cleaning station, comprising:
    1) a sonic cleaner,
    2) a rinsing fountain, and
    3) a vacuum manifold.

* * * * *